(12) United States Patent
Deslongchamps et al.

(10) Patent No.: US 7,452,862 B2
(45) Date of Patent: *Nov. 18, 2008

(54) CONFORMATIONALLY-CONTROLLED BIOLOGICALLY ACTIVE MACROCYCLIC SMALL MOLECULES AS MOTILIN ANTAGONISTS OR GHRELIN AGONISTS

(75) Inventors: Pierre Deslongchamps, Sherbrooke (CA); Yves Dory, Cookshire (CA); Mark Peterson, Rock Forest (CA); Kamel Benakli, Montreal (CA); Eric Marsault, Sherbrooke (CA); Luc Ouellet, Sherbrooke (CA); Mahesh Ramaseshan, Sunnyvale, CA (US); Martin Vézina, Rock Forest (CA); Daniel Fortin, Montreal (CA); Ruoxi Lan, Arlington, MA (US); Shigui Li, Arlington, MA (US); Gérald Villeneuve, Montreal (CA); Hamid Hoveyda, Sherbrooke (CA); Sylvie Beaubien, Sherbrooke (CA); Graeme L Fraser, Sherbrooke (CA)

(73) Assignee: Tranzyme Pharma, Inc. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/911,221

(22) Filed: Aug. 2, 2004

(65) Prior Publication Data

US 2005/0137127 A1    Jun. 23, 2005

Related U.S. Application Data

(60) Provisional application No. 60/491,248, filed on Jul. 31, 2003.

(51) Int. Cl.
*A61K 38/12* (2006.01)
*C07K 5/12* (2006.01)
*C07K 1/00* (2006.01)

(52) U.S. Cl. ............................. 514/11; 530/317; 530/333

(58) Field of Classification Search .................. None
See application file for complete search history.

(56) References Cited

U.S. PATENT DOCUMENTS

| | | | |
|---|---|---|---|
| 3,997,540 | A | 12/1976 | Mehta et al. |
| 6,011,155 | A | 1/2000 | Villhauer |
| 6,165,985 | A | 12/2000 | Jasserand et al. |
| 6,479,460 | B1 | 11/2002 | Bab et al. |
| 6,548,501 | B2 | 4/2003 | Hakkinen |
| 6,852,722 | B2 | 2/2005 | Hakkinen |
| 2005/0049234 | A1* | 3/2005 | Deslongchamps et al. .. 514/183 |
| 2005/0054562 | A1* | 3/2005 | Fraser et al. .................... 514/9 |
| 2005/0119169 | A1* | 6/2005 | Deslongchamps et al. .... 514/10 |

FOREIGN PATENT DOCUMENTS

| | | |
|---|---|---|
| DE | 2235377 | 2/1973 |
| GB | 1365201 | 8/1974 |
| WO | WO-96/22304 A1 | 7/1996 |
| WO | WO-97/48713 A1 | 12/1997 |
| WO | WO-98/46631 A1 | 10/1998 |
| WO | WO-98/54577 A1 | 12/1998 |
| WO | WO-01/25257 A2 | 4/2001 |
| WO | WO-02/08250 A2 | 1/2002 |

OTHER PUBLICATIONS

Siani, Michael A., et al., "Development and screening of a polyketide virtual library for drug leads against a motilide pharmacophore", Journal of Molecular Graphics and Modelling, vol. 18, 2000, pp. 497-511.

Sato, Takeo, et al., "Medium-sized Cyclophanes. Part XV. 10,15-Dihydro-5H-tribenzo-[a,d,g]cyclononene and Analogues", J. Chem. Soc. Perkin I, 1973, pp. 895-900.

Romanovaskis, et al., "Preparation of head-to-tail cyclic peptides via side-chain attachment: Implications for library synthesis", J. Peptide Res., vol. 52, 1998, pp. 356-374.

Horton, Douglas A., et al., "Exploring privileged structures: The combinatorial synthesis of cyclic peprides", Molecular Diversity, 2002, vol. 5, pp. 289-304.

Wenlock, Mark C., et al., "A Comparison of Physciochemical Property Profiles of Development and Marketed Oral Drugs", J. Med. Chem., 2003, vol. 46, pp. 1250-1256.

Veber, Daniel F., et al., "Molecular Properties That Influence the Oral Bioavailability o Drug Candidates", J. Med. Chem. 2002, vol. 45, pp. 2615-2623.

Mori, Kenji, et al., "Synthesis of Moncerin, an Antifungal, Insecticidal and Phytotoxic Heptaketide Metabolite of Excerohilum Monoceras", Tetrahedron, 1989, vol. 45, No. 6, pp. 1639-1646.

(Continued)

*Primary Examiner*—Andrew D Kosar
(74) *Attorney, Agent, or Firm*—Myers Bigel Sibley & Sajovec, PA

(57) ABSTRACT

Novel spatially-defined macrocyclic compounds containing specific conformational control elements are disclosed. Libraries of these macrocycles are then used to select one or more macrocycle species that exhibit a specific interaction with a particular biological target. In particular, compounds according to the invention are disclosed as agonists or antagonists of a mammalian motilin receptor and a mammalian ghrelin receptor.

4 Claims, 19 Drawing Sheets

OTHER PUBLICATIONS

Kogan, Timothy P., et al., "A Regio- and Stereocontrolled Total Synthesis of (-)-Indolactam-V", Tetrahedron, 1990, vol. 46, No. 19, pp. 6623-6632.

Knapp, Spencer, et al., "Synthesis of Hypusine and Other Polyamines Using Dibenzyltriazones for Amino Protection", J. Org. Chem., 1992, vol. 57, pp. 6239-6256.

Boger, Dale L., et al., "Total Synthesis of HUN-7293", J. Am. Chem. Soc., 1999, vol. 121, pp. 6197-6205.

Bednarek, Maria A., et al., "Structure-Function Studies on the New Growth Hormone- Releasing Peptide, Ghrelin: Minimal Sequence of Ghrelin Necessary for Activiation of Growth Hormone Secretagogue Receptor 1a", J. Med. Chem., 2000, vol. 43, pp. 4370-4376.

Palucki, Brenda L., et al., "Spiro(indoline-3,4'-piperidine) Growth Hormone Secretagogues as Ghrelin Mimetics", Bioorganic & Medicinal Chemistry Letters, 2001, vol. 11, pp. 1955-1957.

Davies, John S., "The Cyclization of Peptides and Depsipeptides", Journal of Peptide Science, vol. 9, 2003, pp. 471-501.

Suat Kee, et al., "Design of β-turn Based Therapeutic Agents", Current Pharmaceutical Design, 2003, vol. 9, pp. 1209-1224.

Eguchi, Masakatsu, et al., "Design, Synthesis, and Application of Peptide Secondary Structure Mimetics", Mini Reviews in Medicinal Chemistry, 2002, vol. 2, pp. 447-462.

Glenn, Matthew P., et al., "Mimetics of the Peptide β-Strand", Mini Reviews in Medicinal Chemistry, 2002, vol. 2, pp. 433-445.

Li, Peng et al., "Current Synthetic Approaches to Peptide and Peptidomimetic Cyclization", Current Organic Chemistry, 2002, vol. 6, pp. 411-440.

Souers, Andrew J., et al., "β-Turn mimetic library synthesis: scaffolds and applications", Tetrahedron 57, 2001, pp. 7431-7448.

Tyndall, Joel D.A., et al., "Macrocycles Mimic the Extended Peptide Conformation Recognized by Aspartic, Serine, Cysteine and Metallo Proteases", Current Medicinal Chemistry, 2001, vol. 8, pp. 893-907.

Burgess, Kevin, "Solid-Phase Syntheses of β-Turn Analogues to Mimic or Disrupt Protein—Protein Interactions", Acc. Chem. Res., 2001, vol. 34, pp. 826-835.

Lambert, John N., et al., "The synthesis of cyclic peptides", J. Chem. Soc., Perkin Trans. 1, 2001, pp. 471-484.

MacDonald, Mary, et al., "Approaches to Cyclic Peptide β-Turn Mimics", Current Organic Chemistry, 2001, vol. 5, pp. 417-438.

Kim, Hwa-Ok, et al., "A Merger of Rational Drug Design and Combinatorial Chemistry: Development and Application of Peptide Secondary Structure Mimetics", Combinatorial Chemistry & High Throughput Screening, 2000, vol. 3, pp. 167-183.

EPO Supplementary Partial European Search Report for EP 04 76 1605, Jul. 25, 2006.

Haramura, M, et al., Design and synthesis of N-terminal cyclic motilin partial peptides: a novel pure motilin antagonist, Chemical and Pharmaceutical Bulletin (Jan. 2001), pp. 40-43, 49:1.

Inge Depoortere, et al., Interaction of the growth hormone-releasing peptides ghrelin and growth-hormone releasing peptide-6 with motilin receptor in the rabbit gastric antrum, The Journal of Pharmacology and Experimental Therapeutics (2003), pp. 660-666, 305:2.

Khiat, A, et al., Identification of the motilide pharmacophores using quantitative structure activity relationships, Journal of Peptide Research (Oct. 1, 1998), pp. 321-328, 52:4.

Koga, H, et al., Macrolide-type motilin receptor agonists: assessment of the biological value of the 2'- and 4"-hydroxyl groups of acid-stable 8,9-anhydroerythromycin A 6,9- hemiacetals, Bioorganic & Medicinal Chemistry Letters (1994), pp. 1649-1654, 4:13.

Haramura, M, et al., Design and synthesis of motilin antagonists derived from the [1,4] fragment of porcine motilin, Journal of Medicinal Chemistry (Jan. 31, 2002), pp. 670-675, 45:3.

Takanashi, H, et al., Selective motilin receptor antagonist in the smooth muscle of the rabbit small intestine, Journal of Phamacology and Experimental Therapeutics (1995), pp. 624-628, 273:2.

Examination Report corresponding to European Application No. 04761605.7-1216 mailed Mar. 12, 2008.

* cited by examiner

Reagents: a) TMSCN, BF$_3$·Et$_2$O, 85%; b) NaBH$_3$(O$_2$CCF$_3$), $^{S22}$ THF, 28°C, 80%; c) pyr, Ac$_2$O, 90%; d) 1. Boc$_2$O, DMAP, THF, 88%; 2. NaOMe, MeOH, 95%; e) TBDPSCl, pyr, DMAP, 70%; f) MeI, Ag$_2$O, DMF-CH$_3$CN, 50°C, 90%; g) TBAF, THF, 90%.

Reagents: a) Ac$_2$O/pyr , b) CH$_2$=CH-CH$_2$TMS, BF$_3$·Et$_2$O, (85%); c) NIS, THF, 6 d, 80% (from α-anomer only, β-anomer used for T56 and T57); d) NaN$_3$, DMF, 70°C, 85%; e) flash chromatography separation of diastereomers; f) TFA/Ac$_2$O, 75%; g) 1. MeONa, MeOH, 90%; 2. PPh$_3$, 40°C, THF-H$_2$O, then Boc$_2$O, NaHCO$_3$, 90%.

a-TMSCN, BF$_3$.OEt$_2$, DCM, 67%; b-LAH, THF; c-Ddz-OPh, TEA, DMF, 50° C, 60%; d-TBDPSCl, DMAP, Py/DCM, 90%; e- I$_2$, Im, PPh$_3$, C$_6$H$_5$CH$_3$/THF, reflux, 80%; f- TBAF, THF, 90%.

Overall yield: 77.2% 4 steps    The (S) isomer is prepared dientically starting from the enantiomer of 33-1.

*Chiral versions of this tether are obtained starting from the enantiomers of 38-A.*

Reagents: a) TFA/ Ac₂O, 75%; b) MeONa, MeOH, 90%

CONFORMATIONALLY-CONTROLLED BIOLOGICALLY ACTIVE MACROCYCLIC SMALL MOLECULES AS MOTILIN ANTAGONISTS OR GHRELIN AGONISTS

FIELD OF THE INVENTION

This invention relates to spatially-defined macrocyclic compounds with specific conformational control elements. It also relates to the generation of libraries of these macrocycles. These libraries are then used to select one or more macrocycle species that exhibit a specific interaction with a particular biological target.

BACKGROUND OF THE INVENTION

Among the variety of compounds that have consistently been found to possess potent and selective biological activity are natural products and peptides. Indeed, members of these classes have become useful pharmaceutical agents. Unfortunately, each type has limitations that have restricted the wider utility of these structures.

In fact, natural products often have extremely complex structures that are difficult to synthesize, particularly in the combinatorial fashion that would provide access to a greater number of analogues with which to define pharmacophoric elements and best explore modulation of the biological properties of the parent compound. Nevertheless, some efforts have been successful at constructing natural product libraries containing a modest number of analogues.

Peptides, on the other hand, have been at the forefront of the development of combinatorial chemistry due to their ease of synthesis on solid support, the reproducible and high-yielding reactions involved, and the ready availability of starting materials. Peptides being the endogenous ligands for a number of enzymes and receptors, their modification can be performed to develop even more potent agonists or inhibitors of these same receptors and enzymes. In addition, combinatorial peptide libraries have been used to find a number of previously unknown active sequences for a wide array of enzyme and receptor systems.

However, peptidic compounds are plagued by the usual limitations associated with the direct use of peptides as pharmaceuticals, including rapid metabolic degradation by proteases, short pharmacokinetic half-life, difficulty in transport to site of action in tissues and organs, poor oral bioavailability and solubility, potential antigenicity, as well as high manufacturing costs.

Nevertheless, the densely functionalized and structurally diverse nature of peptides is advantageous when seeking new drug molecules. Hence, peptides are primarily used as the starting point or template for the development of new pharmaceutical leads that often results in structures that only partially resemble, if at all, the initial active peptide. In particular, the recognition potential of the amino acid side chains has resulted in attempts to incorporate these side chains into non-peptidic rigid scaffolds that attempt to duplicate the conformational display required for optimal interaction between the molecule and the target, as well as mimic standard protein and peptide secondary structural elements. For example, sugars and aromatic rings have been exploited as rigid scaffolds containing amino acids or analogues as pendant moieties at one or more positions. Compounds and combinatorial libraries utilizing 3- and 4-substituted pyrrolidines as a central template for display of interacting functionality have been disclosed in U.S. Pat. No. 5,646,285 and U.S. Pat. No. 5,891, 737.

In another approach, cyclic structures can greatly improve the pharmacological and pharmacokinetic profiles of peptides (*Molecular Diversity* 2000 (pub. 2002), 5, 289-304). Cyclic peptides analogues offer a number of benefits compared with the corresponding linear analogues, including restricted conformational mobility, defined topology, enhanced stability to proteolytic enzymes and modified polarity. Furthermore, cyclic peptides can enhance potency, selectivity, stability, bioavailability and membrane permeability. The stability to enzymatic degradation of the cyclic structure arises from the difficulty of such molecules to attain the extended conformation required to be recognized as a substrate for peptidases. Very large mixture libraries ($10^8$ members or more) of cyclic peptides have been described in WO 98/54577.

However, larger rings are often too flexible and can occupy too many conformations to be useful. Further, their molecular size and resulting physicochemical characteristics do not fit the typical requirements for being "drug-like." Small cyclic peptides containing the key interacting residues would provide the necessary conformational restriction, but may have other disadvantages, including synthetic difficulty, ease of dimerization, unfavorable ring strain caused by the presence of the preferred trans amide bonds, lack of stability towards metabolism and hydrolysis to release that strain and limited topological diversity.

Most attention in combinatorial chemistry has been devoted to producing diversity in terms of chemical composition. However, essentially no effort has been directed at integrating this with diversity in terms of the crucial three-dimensional structure.

The use of certain tether elements to control conformation was reported in WO 01/25257. However, although those tethers were successful in restricting the conformational display of the molecule, they only were able to duplicate a portion of the spatial region accessible to a linear molecule, which can contain hundreds if not thousands of possible conformations. To better cover the available conformational space, additional tether elements that define new conformations are required. In addition, the tethers in the previous report were generally hydrophobic in nature. This effects key properties of the macrocyclic molecules such as solubility and log P that are known to have an impact on the compound's pharmacological properties, in particular oral bioavailability. Further, variation of these physicochemical properties is often required in order to optimize the desired characteristic of a molecule as a therapeutic agent. As well, the early tethers were rather limited in their chemical functionality. Since this part of the molecule also could have interactions with a biological target in addition to its conformational control function, a greater diversity in the chemical functional groups could prove advantageous. The more chemically diverse tethers of the present invention therefore have been designed to address these limitations of the existing art and provide the following benefits:

Access to previously inaccessible conformations

Modification of physicochemical parameters

Improvement of pharmacokinetic profile

Additional interacting functionalities for modulation of biological activity

Growing evidence suggests that molecular rigidity confers favorable pharmacokinetic properties on molecules and leads to improved clinical success (*J. Med. Chem.* 2003, 46, 1250-1256; *J. Med. Chem.* 2002, 45, 2615-2623). The tethers of the present invention therefore will be extremely useful in utilizing these macrocyclic molecules in the search for new pharmaceuticals. Examples of the activity that have been exhibited by representative molecules of the invention are provided.

Therefore, there remains a need for specifically designed chemical entities built on a macrocyclic framework, which exploit the three-dimensional conformation changes triggered by peptidic modifications and/or by inserting specific tether-like portions, in their macrocyclic skeleton.

SUMMARY OF THE INVENTION

The present invention is directed towards spatially-defined macrocyclic compounds which incorporate conformational control elements in order to limit their three-dimensional structure to a small number of spatial orientations. These compounds are defined by general formula (1):

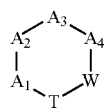

(I)

wherein $A_1$, $A_2$, $A_3$ and $A_4$ are natural amino acid residues or unnatural amino acid residues;

$A_3$ and $A_4$ are optionally present;

W is O or —$NR_1$—, wherein $R_1$ is selected from the group consisting of hydrogen, alkyl, substituted alkyl, acyl and sulfonyl;

T is a bivalent radical chosen from the group consisting of

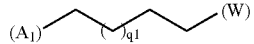

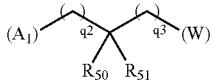

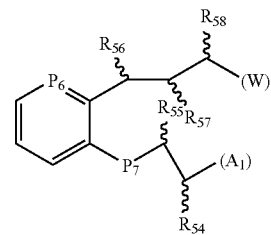

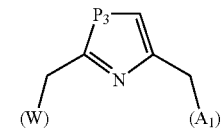

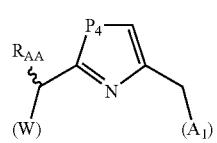

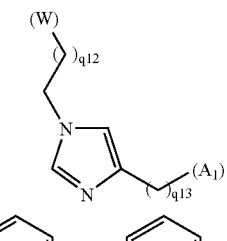

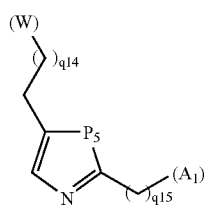

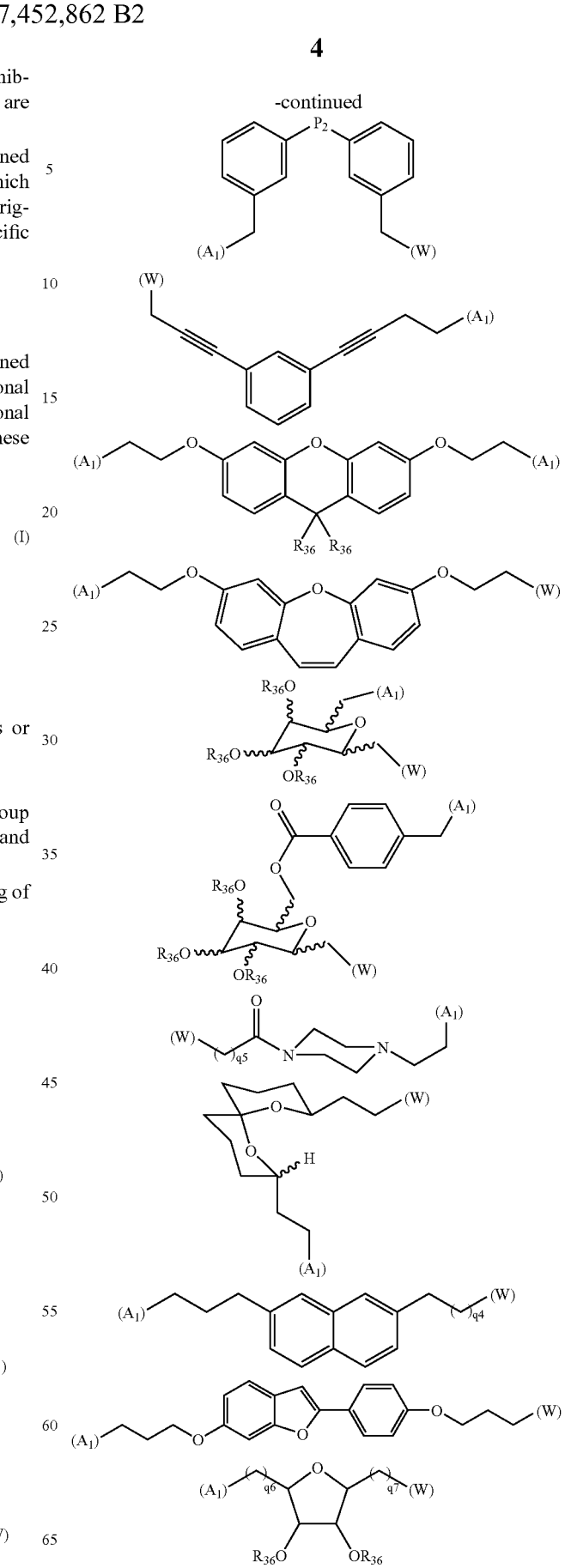

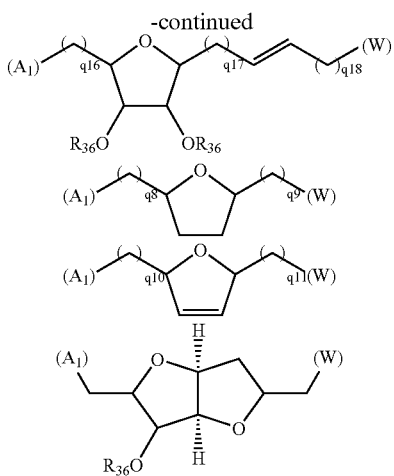

wherein $q_1$, $q_2$, $q_3$, $q_6$, $q_7$, $q_8$, $q_9$, $q_{10}$, $q_{11}$, $q_{13}$, $q_{15}$ and $q_{16}$ are each independently 1, 2, 3, 4 or 5;

$q_4$ and $q_{18}$ are independently 1 or 2;

$q_5$ is 2, 3 or 5;

$q_{12}$ and $q_{14}$ are each independently 0, 1, 2, 3 or 4;

$q_{17}$ is 0, 1, 2 or 3;

$P_1$, $P_2$, $P_3$ $P_4$ and $P_5$ are each independently O, S or NH;

$P_6$ is N or CH;

$P_7$ is O or $CR_{52}R_{53}$;

$R_{36}$ is hydrogen, $C_1$-$C_6$ alkyl, benzyl or acyl;

$R_{50}$ and $R_{51}$ are independently selected from the group consisting of hydrogen, alkyl, hydroxy, alkoxy, or amino with the proviso that if one of $R_{50}$ or $R_{51}$ is hydroxy, alkoxy or amino, the other is hydrogen or alkyl;

$R_{52}$ and $R_{53}$ are independently selected from the group consisting of hydrogen, alkyl, hydroxy, alkoxy, or amino with the proviso that if one of $R_{52}$ or $R_{53}$ is hydroxyl, alkoxy or amino, the other is hydrogen or alkyl;

$R_{54}$, $R_{55}$, $R_{56}$, $R_{57}$ and $R_{58}$ are independently selected from the group consisting of hydrogen, alkyl, hydroxy, alkoxy, or amino;

$R_{AA}$ is a side-chain of a natural amino acid or a side-chain of an unnatural amino acid;

(W) indicates the point of attachment of T to W;

and ($A_1$) indicates the point of attachment of T to $A_1$.

Libraries of these compounds are then used to select one or more macrocycle species that exhibit a specific interaction with a particular biological target. Such targets include, but are not limited to, enzymes and receptors. More particularly, the macrocyclic libraries of the invention serve as a readily accessible source of diverse macrocyclic compounds for use in identifying new biologically active macrocyclic compounds through pharmaceutical candidate screening assays, for use in studies defining structure/activity relationships, and/or for use in clinical investigation. In particular, compounds of formula (I) are disclosed as agonists or antagonists of a mammalian motilin receptor and a mammalian ghrelin receptor.

While the invention will be described in conjunction with an example embodiment, it will be understood that it is not intended to limit the scope of the invention to such embodiment. On the contrary, it is intended to cover all alternatives, modifications and equivalents as may be included as defined by the appended claims.

BRIEF DESCRIPTION OF THE DRAWINGS

FIG. (I) is a general scheme showing one approach to the solid phase synthesis of compounds of the invention.

FIG. (II) is a general scheme showing a second approach to the solid phase synthesis of compounds of the invention.

DETAILED DESCRIPTION OF THE INVENTION

Figure 1:
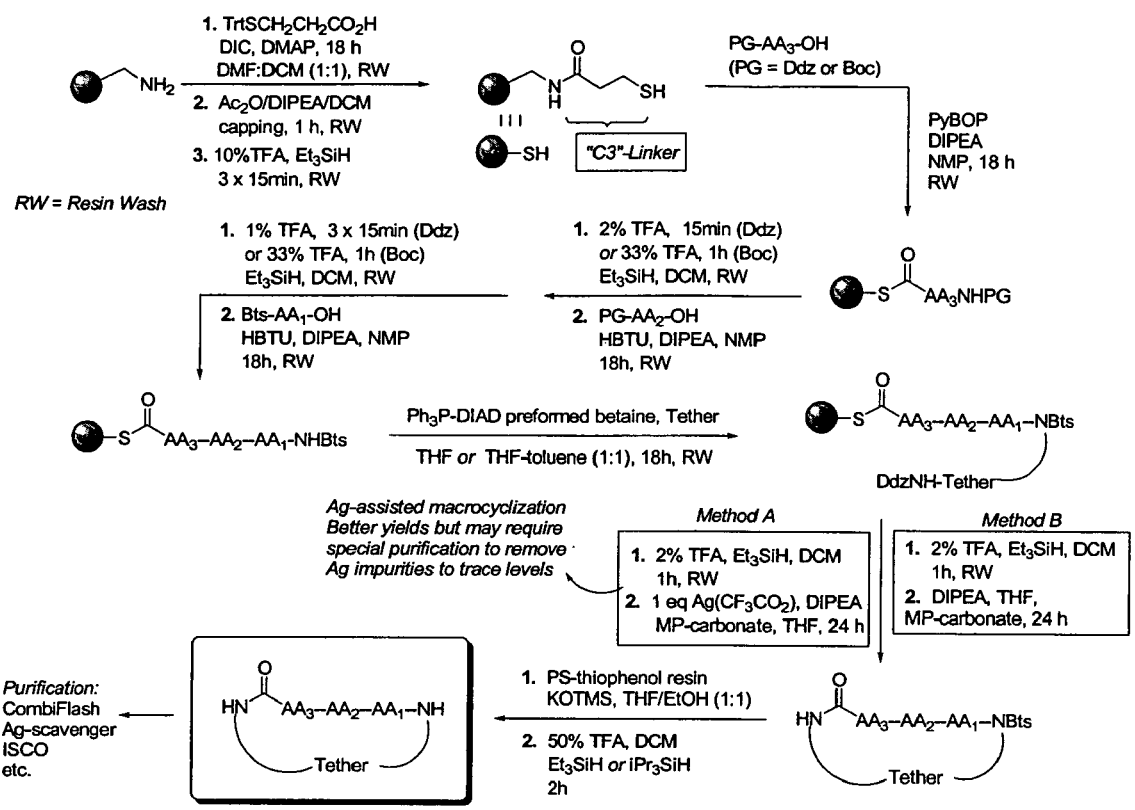

The macrocyclic compounds of the present invention incorporate a variety of tethers, thus allowing coverage of a specific section of conformational space. Furthermore, these tethers are selected on the basis of their ability to synthetically produce macrocycles in reasonable yield across a wide range of sequences. Accordingly, the compounds of the invention, which incorporate these tethers, represent a wide variety of different conformations, with some more rigid and others more flexible. In addition, some of the tethers are much more rigid in their conformation, sometimes displaying essentially only one low energy form. In these cases, improved biological results would provide excellent information on the specific, optimum bioactive conformation. Additionally, in contrast to many traditional approaches, the same synthetic routes and methods are employed in this optimization process. The ability to rapidly access such information transforms what is usually an extremely difficult and time intensive task into a much more straight forward undertaking.

As such, this invention permits the simultaneous investigation of chemical and conformational diversity within a single structural framework and therefore possesses great potential for use in increasing the speed and efficiency of research aimed at new pharmaceuticals.

Accordingly, the invention provides macrocyclic compounds of formula (I) wherein $A_1$, $A_2$, $A_3$, $A_4$, W and T are as defined previously.

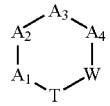

(I)

In a specific embodiment, there are provided compounds of formula (I), T is chosen from the following bivalent radicals:

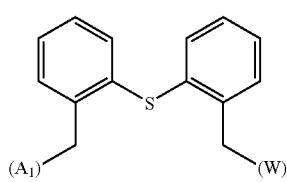

T12

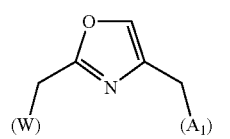

T13

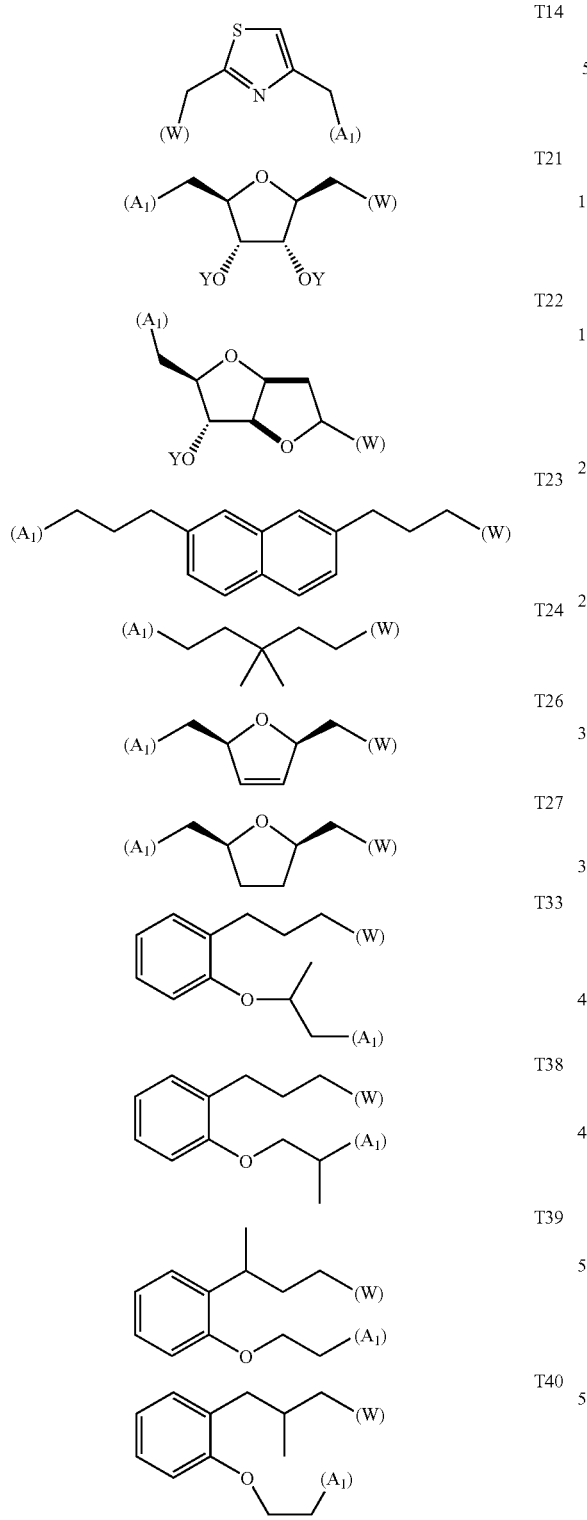
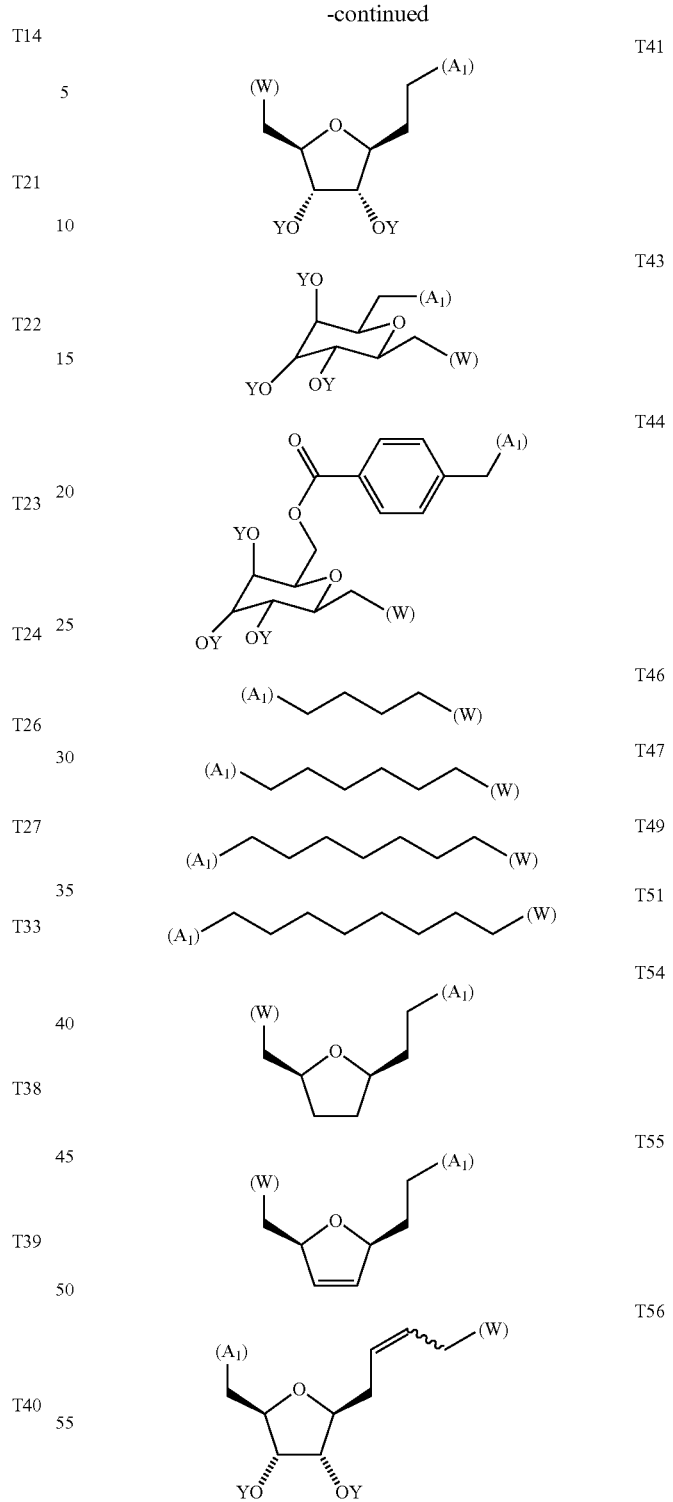

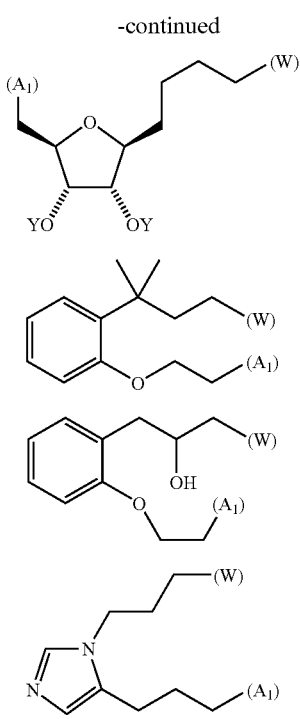

wherein Y is selected from hydrogen, alkyl, benzyl or acyl.

The invention also provides compounds of formula 1 wherein at least one of $A_1$, $A_2$, $A_3$ and $A_4$ can further be a protected natural or unnatural amino acid residue.

The present invention has applicability to a broad range of biological targets that likewise represent diverse therapeutic indications. Active compounds initially generated can be further optimized and refined to eventually provide lead clinical candidates. A further advantage of the invention is that these subsequent steps in the optimization process can be conducted utilizing the same basic chemical synthesis pathway, hence greatly simplifying and speeding up what is typically an extremely time-consuming phase of the overall drug discovery process.

In particular, the invention provides compounds of formula (I)) which are agonists or antagonists of a mammalian motilin receptor and/or a mammalian ghrelin receptor.

Motilin, a linear 22-amino acid peptide, plays a critical regulatory role in the GI physiological system through governing of fasting gastrointestinal motor activity. As such, the peptide is periodically released from the duodenal mucosa during fasting in mammals, including humans. More precisely, motilin exerts a powerful effect on gastric motility through the contraction of gastrointestinal smooth muscle to stimulate gastric emptying, decrease intestinal transit time and initiate phase III of the migrating motor complex in the small bowel. Due to the critical and direct involvement of motilin in control of gastric motility, agents that either diminish (hypomotility) or enhance (hypermotility) the activity at the motilin receptor, are a particularly attractive area for further investigation in the search for new effective pharmaceuticals towards these indications. Macrocyclic antagonists of the motilin receptor are disclosed in U.S. Prov. Pat. Appl. Ser. No. 60/479,223.

Likewise, ghrelin is a key peptide hormone involved in a number of important physiological functions including growth hormone secretion, maintenance of energy balance, appetite and gut motility. As such, antagonists of this receptor have been investigated for treatment of obesity, while ghrelin agonists have interest in treatment of a variety of diseases, including conditions caused by growth hormone deficiency, wasting syndrome, and GI disorders involving dysmotility.

```
motilin (human, porcine,SEQ ID NO:1)
Phe-Val-Pro-Ile-Phe-Thr-Tyr-Gly-Glu-Leu-Gln-Arg- Met-Gln-Glu-Lys-Glu-Arg-Asn-Lys-Gly-Gln ghrelin (human SEQ ID NO:2)
Gly-Ser-Ser(Oct)-Phe-Leu-Ser-Pro-Glu-His-Gln-Arg- Val-Gln-Gln-Arg-Lys-Glu-Ser-Lys-Lys-Pro-Pro-Ala- Lys-Leu-Gln-Pro-Arg
```

EXAMPLES

Synthesis Method

An assortment of synthetic strategies, involving both solution and solid phase techniques, can be used to access the macrocyclic compounds of the invention, several of which have already been disclosed in WO 01/25257.

An outline of a first approach to the solid phase synthesis of the compounds of the invention, using a thioester linker strategy is provided in FIG. (I). A second approach, called ring-closing metathesis (RCM), is also generally outlined in FIG. (II).

In both, the construction involves four phases: first is synthesis of the building blocks, comprising mainly recognition elements for interaction at biological targets, plus the key tether moiety, primarily for control and definition of conformation. These building blocks are assembled together, typically in a sequential fashion, in a second phase employing standard chemical transformations and those described in the Standard Procedures herein. The precursors from the assembly are then cyclized in the third stage, which could involve multiple steps, to provide the macrocyclic structures. Finally, a post-cyclization processing stage involving removal of protecting groups and optional purification then provides the desired final compounds.

General Information

Reagents and solvents were of reagent quality or better and were used as obtained from various commercial suppliers unless otherwise noted. DMF, DCM, DME and THF used are of DriSolv® (EM Science, now EMD Chemicals, Inc., part of Merck KGaA, Darmstadt, Germany) or synthesis grade quality except for (i) deprotection, (ii) resin capping reactions and (iii) washing. NMP used for the amino acid (AA) coupling reactions is of analytical grade. DMF was adequately degassed by placing under vacuum for a minimum of 30 min prior to use. Boc— and Fmoc—protected amino acids and side chain protected derivatives, including those of N-methyl and unnatural amino acids, were obtained from commercial suppliers or synthesized through standard methodologies known to those in the art. Ddz-amino acids were either synthesized by standard methods, or obtained commercially from Orpegen (Heidelberg, Germany) or Advanced ChemTech (Louisville, KY, USA). Bts-amino acids were synthesized by established procedures. Hydroxy acids were obtained from commercial suppliers or synthesized from the corresponding amino acids as described in the literature (*Tetrahedron* 1989, 45, 1639-1646; *Tetrahedron* 1990, 46, 6623-6632; *J.Org. Chem.* 1992, 57, 6239-6256.; J. Am. Chem. Soc.

1999, 121, 6197-6205). Analytical TLC was performed on pre-coated plates of silica gel 60F254 (0.25 mm thickness) containing a fluorescent indicator.

$^1$H and $^{13}$C NMR spectra were recorded on a Varian Mercury 300 MHz spectrometer (Varian, Inc., Palo Alto. CA) and are referenced internally with respect to the residual proton signals of the solvent. Information about the conformation of the molecules in solution can be determined utilizing appropriate two-dimensional NMR techniques known to those skilled in the art.

HPLC analyses are performed on a Waters Alliance® system 2695 running at 1 mL/min using an Xterra® MS C18 column (or comparable) 4.6 ×50 mm (3.5 µm). A Waters 996 PDA provided UV data for purity assessment (Waters Corporation, Milford, MA). An LCPackings (Dionex Corporation, Sunnyvale, CA) splitter (50:40:10) allowed the flow to be separated in three parts. The first part (50%) went to a mass spectrometer (Micromass® Platform II MS equipped with an APCI probe) for identity confirmation. The second part (40%) went to an evaporative light scattering detector (ELSD, Polymer Laboratories, now part of Varian, Inc., Palo Alto, CA, PL-ELS-1000™) for purity assessment and the last portion (10%) to a chemiluminescence detector (CLND, Antek® Model 8060, Antek Instruments, Houston, TX, part of Roper Industries, Inc., Duluth, GA) for quantitation and purity assessment. Data was captured and processed utilizing the most recent version of the Waters Millennium® software package (Milford, MA).

Preparative HPLC purifications were performed on final deprotected macrocycles using the Waters FractionLynx® system, on an Xterra® MS C18 column (or comparable) 19 ×100mm (5µm). The injections were done using an At-Column-Dilution configuration with a Waters 2767 injector/collector and a Waters 515 pump running at 2 mL/min. The mass spectrometer, HPLC, and mass-directed fraction collection are controlled via MassLynx® software version 3.5 with FractionLynx®. Fractions (13 ×125 mm tubes) shown by MS analysis to contain the product were evaporated under reduced pressure, most typically on a centrifugal evaporator system (Genevac® HT-4 (Genevac Inc, Valley Cottage, NY), ThermoSavant Discovery®, SpeedVac® or comparable (Thermo Electron Corporation, Waltham, MA) or, alternatively, lyophilized. Compounds were then thoroughly analyzed by LC-MS-UV-ELSD-CLND analysis for identity confirmation, purity and quantity assessment.

Automated medium pressure chromatographic purifications were performed on an Isco CombiFlash® 16× system with disposable silica or C18 cartridges that permitted up to sixteen (16) samples to be run simultaneously (Teledyne Isco, Inc., Lincoln, NE). MS spectra were recorded on a Waters Micromass® Platform II or ZQ™ system. HRMS spectra were recorded with a VG Micromass ZAB-ZF spectrometer. Chemical and biological information were stored and analyzed utilizing the ActivityBase® database software (ID Business Solutions Ltd., Guildford, Surrey, UK).

The term "concentrated/evaporated/removed under reduced pressure". indicates evaporation utilizing a rotary evaporator under either water aspirator pressure or the stronger vacuum provided by a mechanical oil vacuum pump as appropriate for the solvent being removed. "Dry pack" indicates chromatography on silica gel that has not been pre-treated with solvent, generally applied on larger scales for purifications where a large difference in $R_f$ exists between the desired product and any impurities. "Flash chromatography" refers to the method described as such in the literature and is applied to chromatography on silica gel (230-400 mesh, EM Science) used to remove impurities some of which may be close in $R_f$ to the desired material. Methods specific for solid phase chemistry are detailed separately.

General Methods for Solid Phase Chemistry

These methods can be equally well applied for the synthesis of single compounds or small numbers of compounds, as well as for the synthesis of libraries of compounds of the present invention.

For solid phase chemistry, the solvent choice is important not just to solubilize reactants as in solution chemistry, but also to swell the resin. Certain solvents interact differently with the polymer matrix depending on its nature and can affect this swelling property. As an example, polystyrene (with DVB cross-links) swells best in nonpolar solvents such as DCM and toluene, while shrinking when exposed to polar solvents like alcohols. In contrast, other resins such as PEG-grafted ones like TentaGel®, Rapp Polymere GmbH, Tübinaen, Germany), maintain their swelling even in polar solvents. For the reactions of the present invention, appropriate choices can be made by one skilled in the art. In general, polystyrene-DVB resins are employed with DMF and DCM common solvents. The volume of the reaction solvent required is generally 1-1.5 mL per 100 mg resin. When the term "appropriate amount of solvent" is used in the synthesis methods, it refers to this quantity. The recommended quantity of solvent roughly amounts to a 0.2 M solution of building blocks (linkers, amino acids, hydroxy acids, and tethers, used at 5 eq relative to the initial loading of the resin). Reaction stoichiometry was determined based upon the "loading" (represents the number of active functional sites, given as mmol / g) of the starting resin.

The reaction can be conducted in any appropriate vessel, for example round bottom flask, solid phase reaction vessel equipped with a fritted filter and stopcock, or Teflon® (DuPont, Wilmington, DE)-capped jar. The vessel size should be such that there is adequate space for the solvent, and that there is sufficient room for the resin to be effectively agitated taking into account that certain resins can swell significantly when treated with organic solvents. The solvent/resin mixture should fill about 60% of the vessel. Take note that all agitations for solid phase chemistry are best conducted with an orbital shaker (for example Forma® Scientific, model 430, 160-180 rpm) (Thermo Electron Corporation, Waltham, MA), except for those where scale makes use of gentle mechanical stirring more suitable, to ensure adequate mixing which is generally accepted to be important for a successful reaction.

The volume of solvent used for the resin wash is a minimum of the same volume as used for the reaction, although more is generally used to ensure complete removal of excess reagents and other soluble residual by-products. Each of the resin washes specified in the Examples should be performed for a duration of at least 5 min with agitation (unless otherwise specified) in the order listed. The number of washings is denoted by "nx" together with the solvent or solution, where n is an integer. In the case of mixed solvent washing systems, both are listed together and denoted solvent 1/solvent 2. The ratio of the solvent mixtures DCM/MeOH and THF/MeOH used in the washing steps is (3:1) in all cases. Other mixed solvents are as listed. After washing, drying in the "standard manner" means that the resin is dried first in air (1 h), and subsequently under vacuum (oil pump usually) until full dryness is attained (minimum 30 min, to O/N).

For representative examples of the new tether moieties disclosed herein, the synthetic routes presented jn FIGS. 3-19 are employed with additional information on selected examples presented further below. Although the routes described represent a specific protection strategy, other suitable protecting groups known in the art can also be employed.

Example T12

Standard Procedure for the Synthesis of Tether T12

Figure 3:
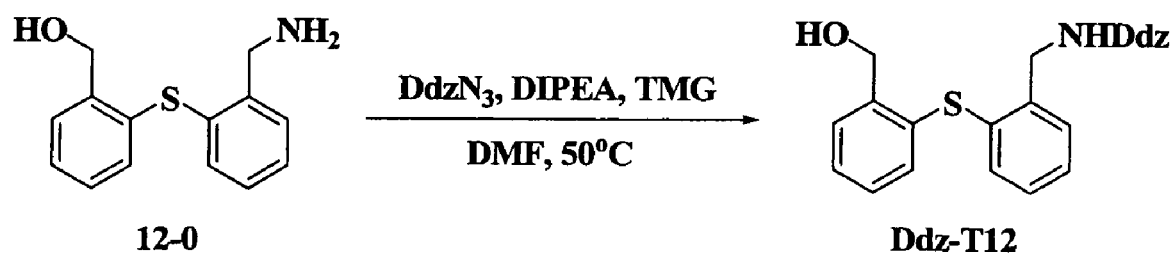
FIGS. 3-16, 17a, 17b, 17c and 18-19 are synthetic schemes that show routes to specific tethers (T) used for the synthesis of compounds of the invention.
Figure 4:
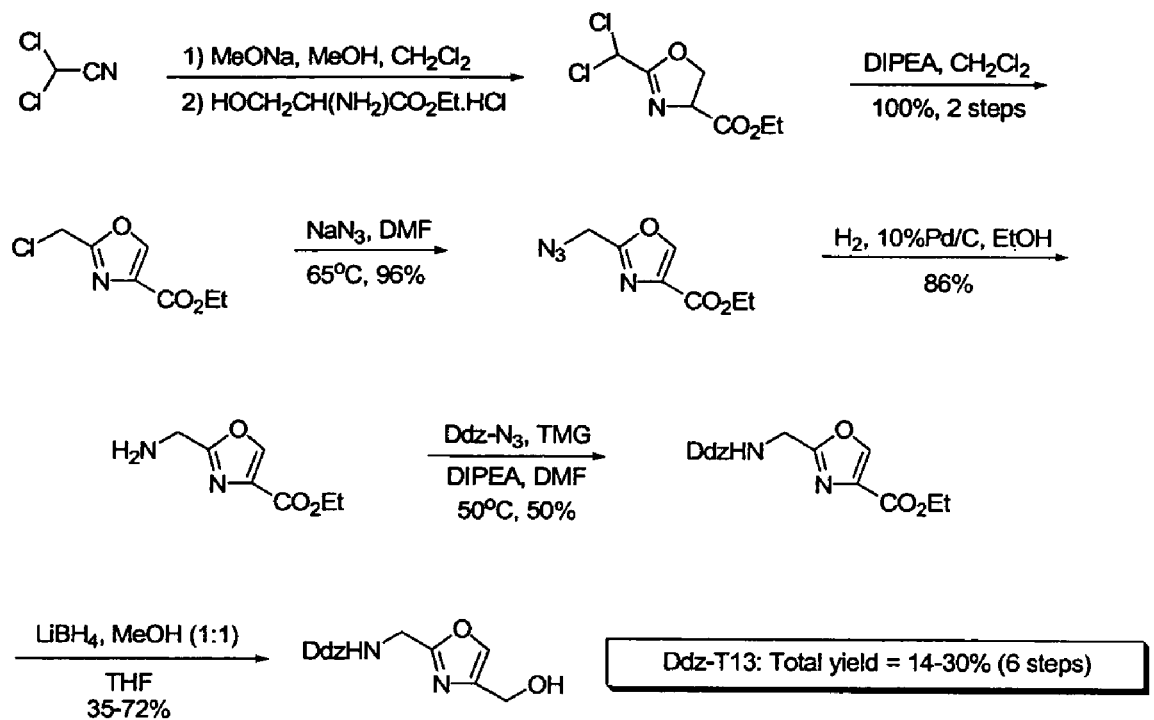

For an outline of this route, see FIG. 3. In a 3-L flame-dried three-neck flask, a solution of (aminomethyl)phenylthiobenzyl alcohol (12-0, 96 g, 0.39 mol) in degassed DMF (1 L, 0.4 M) was prepared. To this was added Ddz-$N_3$ (0.95 eq), followed by 5 TMG (0.39 mol, 49 mL). The reaction was stirred for 10 min, then DIPEA (68 mL, 0.39 mol) added. The mixture was heated at 50° C. under $N_2$ until TLC indicated no Ddz-$N_3$ remained (48 h typically). (TLC eluent: EtOAc:Hex 50:50; detection: ninhydrin). Upon completion, to the reaction mixture was added 3 L citrate buffer and the separated aqueous layer extracted with $Et_2O$ (3×1500 mL). The combined organic phase was washed sequentially with citrate buffer (2×200 mL), water (2×200 mL) and brine (2×200 mL). The organic layer was dried over $MgSO_4$, filtered and the filtrate evaporated under reduced pressure. A dark orange oil was obtained, which was purified by dry-pack. For this procedure, the oil was first dissolved in EtOAc:Hex:DCM:TEA (20:80:1:0.5, v/v/v/v). At this point, a little extra DCM was sometimes required to ensure complete dissolution. The solution was loaded onto the column, then the column eluted with EtOAc:Hex:DCM:$Et_3N$ (20:80:1:0.5) until all the impurities were separated out as indicated by TLC, paying particular attention to that closest to the desired product. The elution was then continued with EtOAc:hexanes:$Et_3N$ 30:70:0.5 (v/v/v) and finally with EtOAc:hexanes:$Et_3N$ (50:50:0.5) to elute the desired product. After removal of the solvent from the fractions containing the product under reduced pressure, the residue was dissolved in the minimum amount of DCM, a three-fold larger volume of hexanes added, then the solvents again evaporated under reduced pressure. This treatment was repeated until an off-white foam was obtained. The latter solidified while drying under vacuum (oil pump). Alternatively, the material yielded a solid after sequential concentration with DCM (1×) and hexanes (2×). Tether T12 was obtained as an off-white solid (85-90% yield).

Example T13

Standard Procedure for the Synthesis of Tether T13

Protected versions of tether T13 are accessed through a route (see FIG. 4) analogous to that described below in more detail for T14, except starting from H-Ser-OEt.HCl, in an overall yield of 14-30% for the 6 step sequence.

$^1$H NMR (CDCl$_3$): δ 7.53 (1H, s, RR'C=C$\underline{H}$—O), 6.42-6.58 (2H, m, Ph), 6.30-6.38 (1H, m, Ph), 5.40-5.50 (1H, m, N$\underline{H}$), 4.57 (2H, s, C$\underline{H}_2$OH), 4.40 (2H, d, C$\underline{H}_2$NHDdz), 3.78 (6H, s, 2X(C$\underline{H}_3$OPh)), 2.23-2.00 (1H, broad, O$\underline{H}$), 1.76 (6H, s, RR'C(C$\underline{H}_3$)$_2$). $^{13}$C NMR (CDCl$_3$): δ 162, 161, 155, 149, 141, 136, 103, 99, 82, 57, 56, 39, 29.

Example T14

Standard Procedure for the Synthesis of Tether T14

Figure 5:
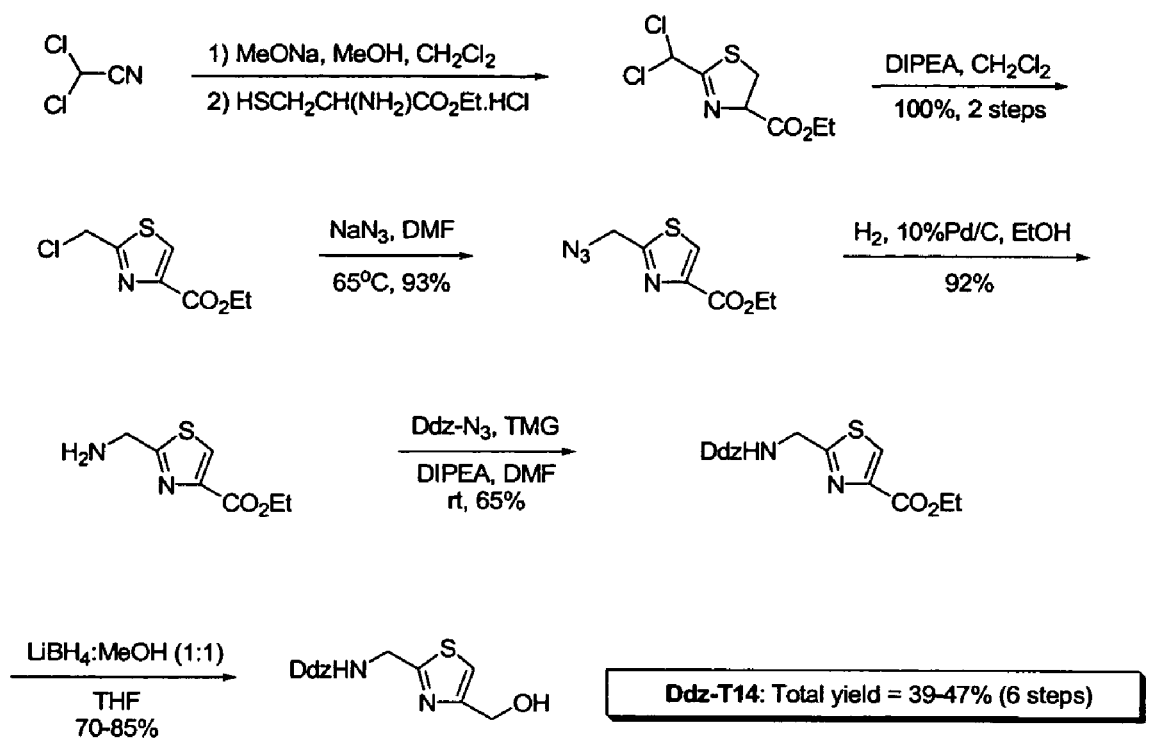

See FIG. 5 for an outline of the synthetic scheme.

Step T14-1: A solution of 4.4 M sodium methoxide in MeOH (1.0 mL, 4.6 mmol, 0.01 eq) in DCM (300 mL) at 0° C. was diluted with MeOH (35 mL). Dichloroacetonitrile (50 g, 455 mmol, 1.0 eq) was added over 45 min and the resulting mixture stirred at 0° C. for 1 h. L-Cysteine ethyl ester hydrochloride (84.5 g, 455 mmol, 1.0 eq) was added and the reaction stirred O/N at rt. The reaction mixture was diluted with DCM and water. The separated aqueous phase was extracted with DCM (2×). The combined organic phase was dried over $MgSO_4$, filtered and the filtrate concentrated under reduced pressure. The crude product obtained was acceptable for use in the next step without further purification.

Step T14-2: To a solution of the crude product from step T14-1 (455 mmol based on the theoretical yield) in DCM (500 mL) was added DIPEA (119 mL, 652.5 mmol, 1.5 eq). The resulting mixture was stirred at 50° C. for 5 h, then at rt O/N. The reaction was monitored by TLC (30% EtOAc: 70% Hex; detection: UV and CMA, $R_f$=0.29). Upon completion, the reaction mixture was diluted with DCM and water. The separated aqueous phase was extracted with DCM (2×). The combined organic phase was dried over $MgSO_4$, filtered and the filtrate concentrated under reduced pressure. $^1$H NMR was used to verify the purity and identity of the intermediate compound. The crude product obtained was acceptable for use in the next step without further purification (yield: 100%).

Step T14-3: To a solution of the crude product from step T14-2 (77 g, 375 mmol, 1.0 eq) in DMF (500 mL) was added sodium azide (122 g, 1874 mmol, 5.0 eq). The resulting mixture was mechanically stirred at 65° C. O/N. The reaction was monitored by $^1$H NMR because the starting material and product co-eluted on TLC. After completion and cooling to rt, the reaction mixture was diluted with $Et_2O$ and an aqueous solution of saturated $NH_4Cl$. The separated aqueous phase was extracted with $Et_2O$ (2×). The combined organic phase was washed with brine, dried over $MgSO_4$, filtered and the filtrate concentrated under reduced pressure. $^1$H NMR was used to verify the purity and identity of the intermediate compound. The crude product obtained was acceptable for use in the next step without further purification (yield: 93%).

Step T14-4: To a solution of the crude azide from step T14-3 (73.1 g, 345 mmol, 1.0 eq) in 95% EtOH (700 mL) was added 10% Pd/C (18.3 g, 17.3 mmol, 0.05 eq). Hydrogen gas was bubbled into the suspension for 1h, then the resulting mixture stirred O/N with a balloon of hydrogen. The reaction was monitored by TLC (30% EtOAc: 70% Hex; detection: UV and ninhydrin.). The final product remained at the baseline and was positive to ninhydrin. If the reaction was not complete as indicated by TLC, another portion of 10% Pd/C (25% of that originally used) was added, hydrogen bubbled through the solution and the resulting suspension was stirred at rt again O/N. The reaction solution was filtered through a Celite® (World Minerals Inc., Santa Barbara, CA) pad and the pad rinsed thoroughly with EtOAc (until no further product was being recovered as indicated by TLC). $^1$H NMR was used to verify the purity and identity of the intermediate compound. The crude product obtained was acceptable for use in the next step without further purification (yield: 93%).

Step T14-5: To a solution of the crude amine from step T14-4 (59.5 g, 320 mmol, 1.0 eq) in degassed (maintained on vacuum pump for 1 h) DMF (200 mL) were sequentially added Ddz-$N_3$ (93.3 g, 352 mmol, 1.1 eq), TMG (40.1 mL, 320 mmol, 1.0 eq) and DIPEA (55.8 mL, 320 mmol, 1.0 eq). The resulting solution was stirred at rt for 2 d. The reaction was monitored by TLC (100% EtOAc; detection: UV and ninhydrin, $R_f$=0.52). Upon completion, the reaction mixture was diluted with $Et_2O$ and an aqueous solution of citrate buffer (1 M). The separated aqueous phase was extracted with $Et_2O$ (2×). The combined organic phase was washed with citrate buffer (1 M, 2×), water (2×), and brine (2×), then dried over $MgSO_4$, filtered and the filtrate concentrated under reduced pressure. The crude product was purified by dry-pack (20% EtOAc: 80% Hex to 50% EtOAc: 50% Hex) to give the protected amino ester as a yellow solid. $^1$H NMR was used to verify the identity of the intermediate compound (yield: 65%).

Step T14-6: To a solution of the protected amino ester from step T14-5 (10.5 g, 25.7 mmol, 1.0 eq) in THF (150 mL) at 0° C. were added lithium borohydride (1.68 g, 77.1 mmol, 3.0 eq) and MeOH (3.1 mL, 77.1 mmol, 3.0 eq). The resulting mixture was stirred for 1 h, then identical portions of lithium borohydride and MeOH were added. The resulting mixture was stirred at rt for 3 h. The reaction was monitored by TLC (5% MeOH, 95% EtOAc; detection: UV and ninhydrin, $R_f$=0.27. Note that the boronate co-eluted with the starting material, but after quenching, this spot disappeared). The reaction mixture was cooled to 0° C. and water was added very slowly (100-150 mL) to quench the reaction. On larger scales, the salts generated in the reaction were not completely soluble in the aqueous phase at this stage which complicated the extraction and led to lower yields. The resulting mixture was then stirred O/N. The aqueous phase was extracted with EtOAc (4×). The organic phase was dried over MgSO$_4$, filtered and the filtrate concentrated under reduced pressure. The compound was purified by flash chromatography (3% MeOH, 97% EtOAc) to give tether Ddz-T14 as a pale yellow solid (yield: 67%).

$^1$H NMR (CDCl$_3$, ppm): 7.53 (1H, s, RR'C=C$\underline{H}$—S), 6.42-6.58 (2H, m, Ph), 6.35 (1H, t, Ph), 5.60-5.50 (1H, m, N$\underline{H}$), 4.75 (2H, s, C$\underline{H}_2$OH), 4.60 (2H, d, C$\underline{H}_2$NHDdz), 3.78 (6H, s, 2x(C$\underline{H}_3$OPh)), 2.70-2.50 (1 H, broad, O$\underline{H}$), 1.76 (6H, s, RR'C(C$\underline{H}_3$)$_2$). $^{13}$C NMR (CDCl$_3$, ppm): 170, 161, 157,156, 149,116, 103, 99, 82, 61, 56, 42, 29.

Example T21

Standard Procedure for the Synthesis of Tether T21

Figure 6:
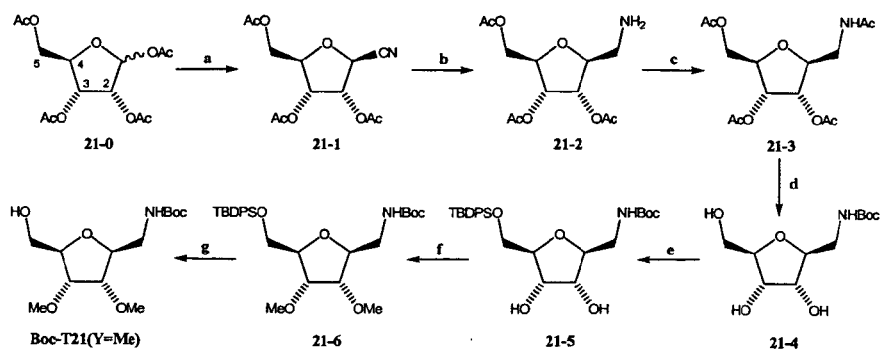

See FIG. 6 for an outline of the synthetic scheme that provides the multi-step protocol for this tether containing methyl ether protection for its secondary hydroxyl groups. Alternative protection that is easier to remove, such as the acetonide, is also possible via this route.

Example T22

Standard Procedure for the Synthesis of Tether T22

Figure 7:
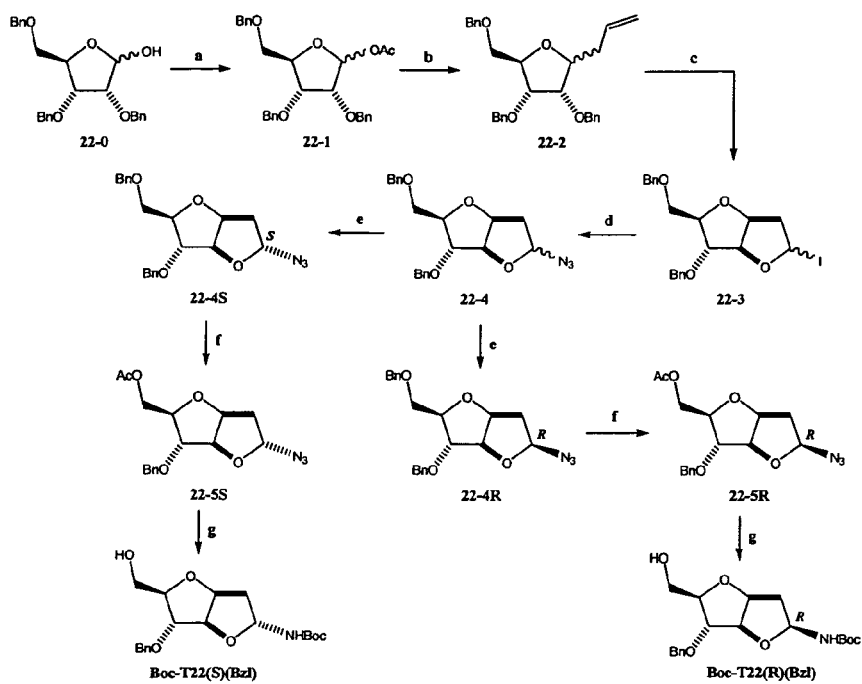

An outline of the synthetic scheme that provides efficient routes to the diastereomeric forms of this tether is shown in FIG. 7.

Example T23

Standard Procedure for the Synthesis of Tether T23

Figure 8:
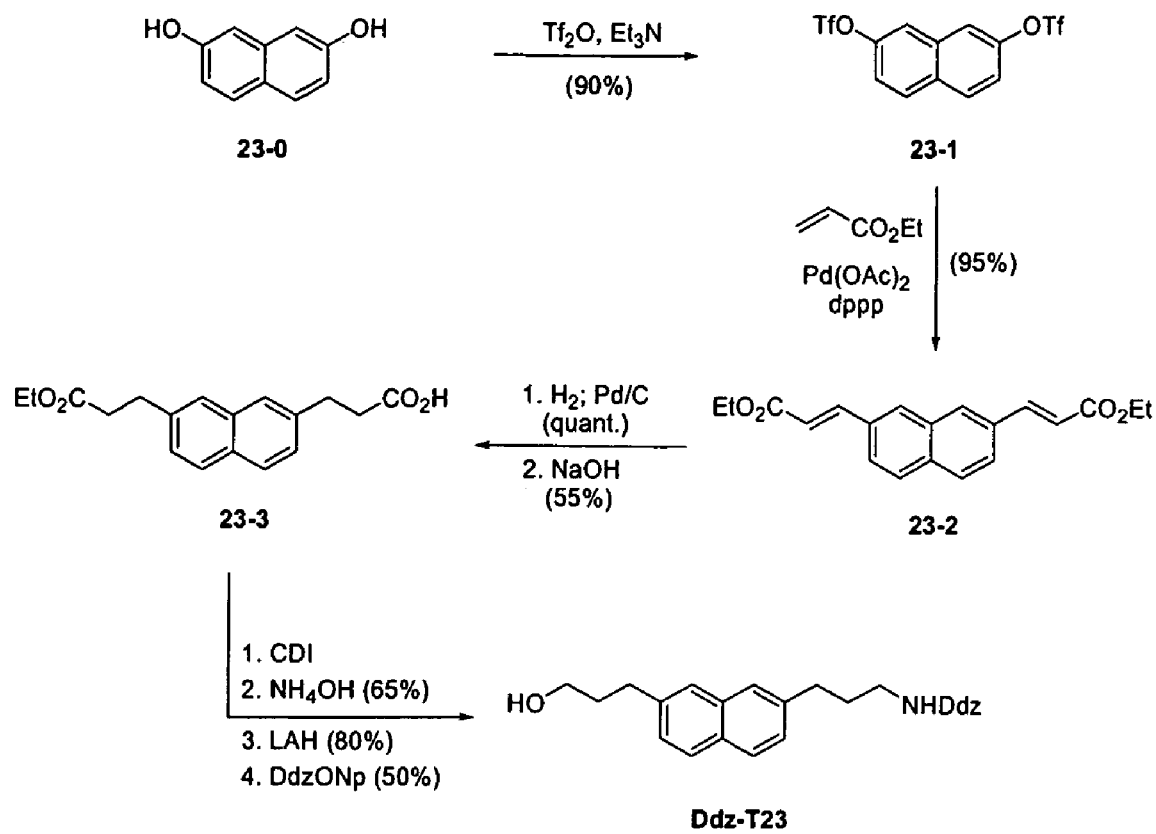

The synthetic scheme that provides routes to this tether tether in shown is FIG. 8. Modifications can be used for homologous tethers.

Example T24

Standard Procedure for the Synthesis of Tether T24

Figure 9:
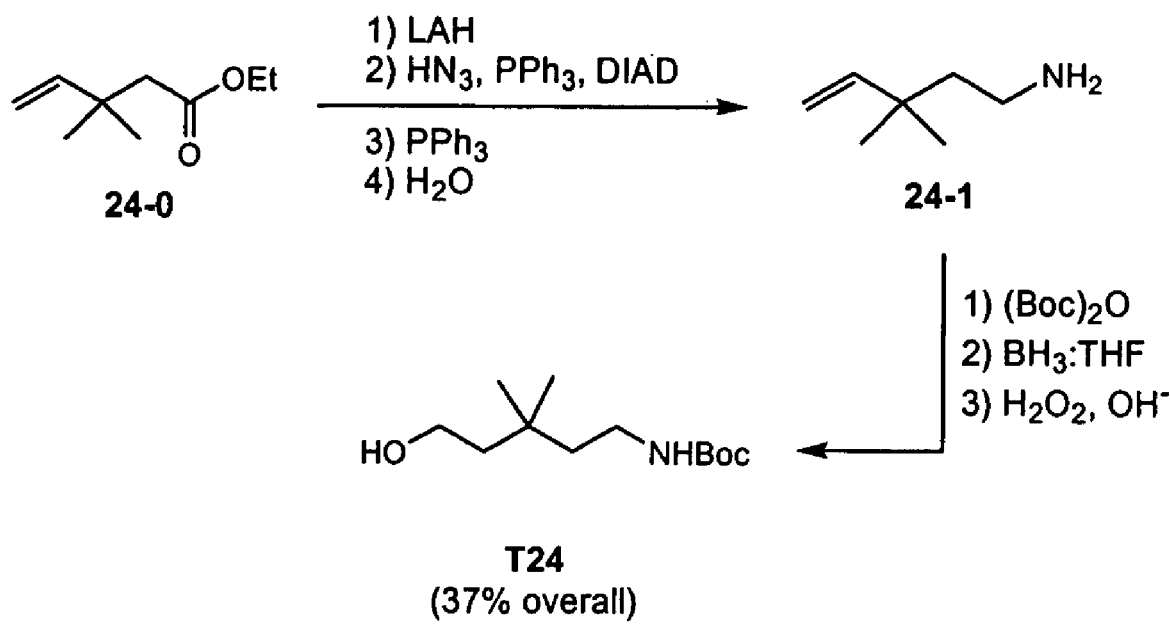

The synthetic approach to this tether is shown in FIG. 9.

Example T24

Standard Procedure for the Synthesis of Tether T26

Figure 10:
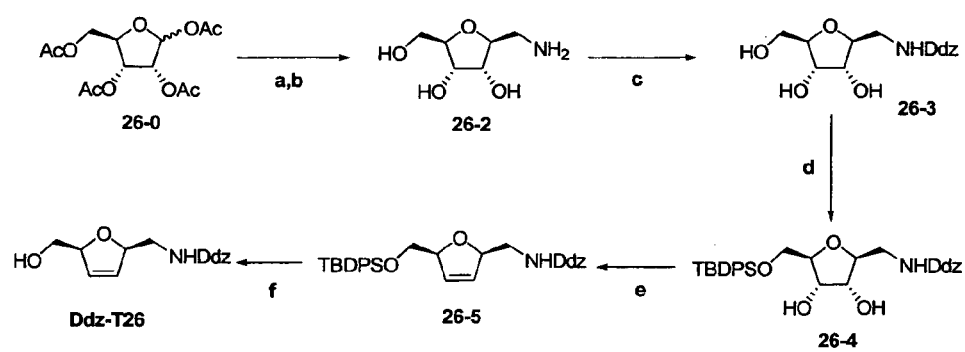

The synthetic scheme that provides this tether is shown in FIG. 10.

MW Calc. for C$_{18}$H$_{25}$NO$_6$, 351.39; MS found (M+H)$^+$ 352

Example T27

Standard Procedure for the Synthesis of Tether T27

Figure 11:
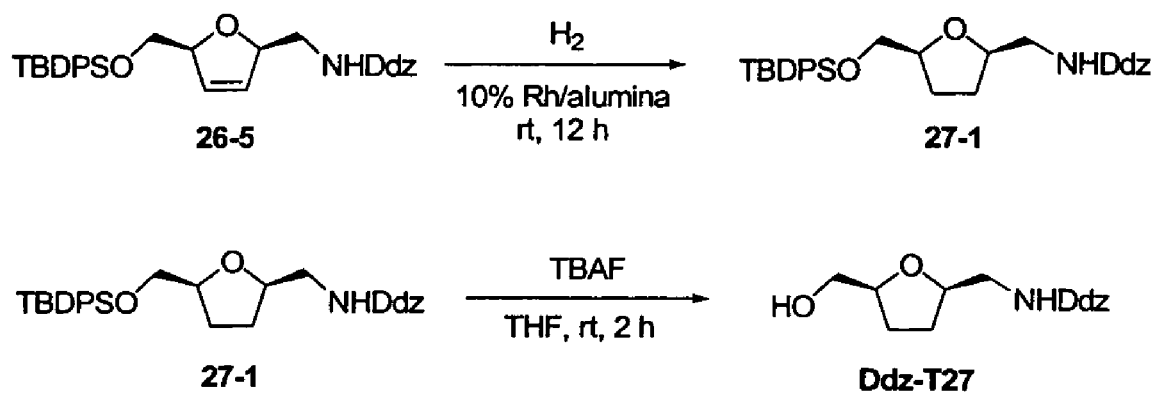

An outline of the synthetic scheme is shown in FIG. 11.

Step T27-1: Ddz-N-(6-O-TBDPS, 2,3-deoxy-β-D-ribofuranosyl)methylamine (27-1). To a solution of 26-5 (20 g, 0.03mmol) in EtOAc (40 mL) was added 10% rhodium on alumina (200 mg). The mixture was hydrogenated under atmospheric pressure using balloon of H$_2$ gas. (CAUTION! Hydrogen gas is flammable.) After 12 h, the reaction mixture was filtered through a short pad of Celite® (World Minerals Inc., Santa Barbara, CA) and the filter cake washed with MeOH. The reaction had to be monitored by NMR since the starting material and product had the same $R_f$ on TLC. The filtrate and washings were combined and concentrated under reduced pressure. The residue was azeotroped with dry toluene to afford a 98% yield of 27-1, which was used directly in the next step without further purification. MW Calc. for C$_{34}$H$_{45}$NO$_6$Si, 591.8097; MS found (M+H)$^+$592.

Step T27-2: Ddz-N-(2,3-deoxy-β-D-ribofuranosyl)methylamine (Ddz-T27). The crude product, 27-1, from the previous step (100 g, 0.17 mol) was dissolved in anhydrous THF (500 mL). To the resulting clear solution was added TBAF (0.25 mol, 250 mL) and the reaction stirred for 2 h at rt. The reaction was monitored by TLC [(EtOAc/hexanes, 1:1,) detection: ninhydrin, $R_f$=0.5]. When the reaction was complete, the solution was poured into ice water and the aqueous solution was extracted with DCM (3×400 mL). The combined organic extract was washed with saturated citrate buffer (1×300 mL), H$_2$O (200 mL) and brine (200 mL). The washed organic extract was dried over anhydrous Na$_2$SO$_4$, filtered and evaporated under reduced pressure to give an oily residue. This residue was purified by flash chromatography (EtOAc/ hexanes, 1:1, $R_f$=0.5) to give the protected tether (Ddz-T27) as a syrup (yield 90%). δ

$^1$H NMR (CDCl$_3$, 300 MHz): δ 1.61 (m, 1H), 1.74 (s, 6H); 1.80-1.88 (m, 3H); 2.66 (s$_b$, 1H); 3.21 (m, 2H); 3.26 (m, 1H), 3.67 (m,1 H); 3.75 (s, 6H); 4.05 (m, 2H);5.25 (m, 1H); 6.32 (m,1H); 6.51 (m, 2H). HPLC (Standard Gradient): Retention time (t$_r$): 6.43 min MW Calc. for C$_{18}$H$_{27}$NO$_6$, 353.4101; MS found (M+H)$^+$ 354.

Example T33

Standard Procedure for the Synthesis of Tether T33

Figure 12:
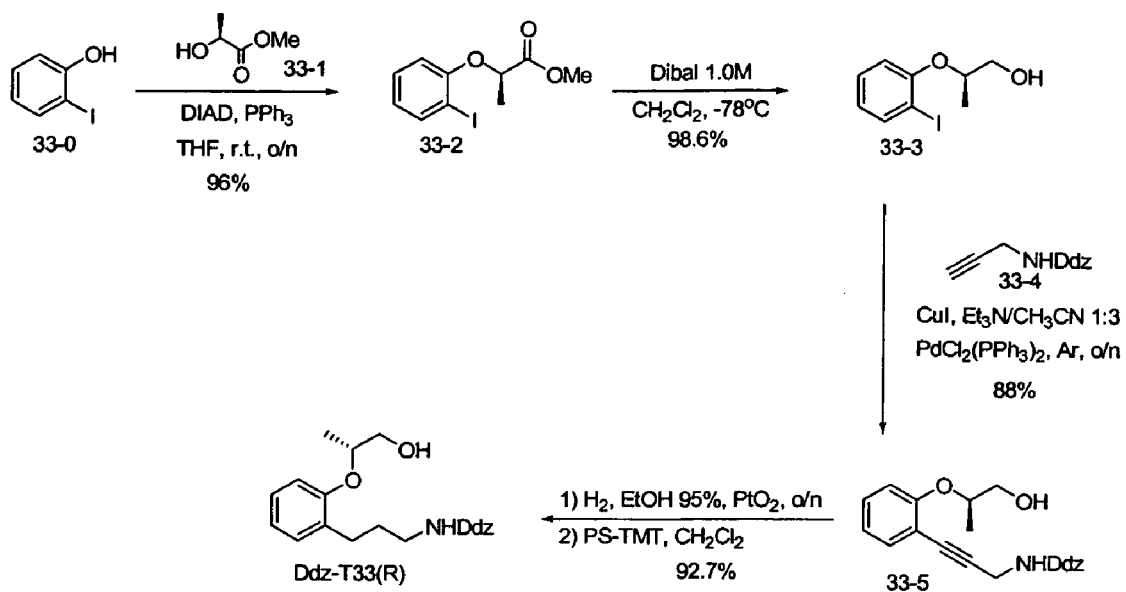

An outline of the synthetic scheme towards this chiral tether is shown in FIG. 12. The enantiomers are accessed depending on the configuration of the starting lactic acid derivative with the (R)-isomer coming from (S)-methyl lactate and the (S)-isomer of T33 resulting from (R)-methyl lactate $^1$H NMR (CDCl$_3$): δ 7.18-7.11 (m, 2H), 6.90 (m, 2H), 6.52 (m, 2H), 6.33(m, 1H), 5.09 (bt, 1H), 4.52 (m, 1H), 3.77 (s, 6H), 3.08 (bq, 2H), 2.64 (bt, 2H), 1.75 (m, 8H); 1.27 (bd, 3H)
$^{13}$C NMR (CDCl$_3$): δ 160.8, 155.5, 149.5, 131.2, 130.6, 127.4, 121.2, 113.3, 103.2, 98,4, 80.7, 74.8, 66.5, 55,4, 40.2, 30.6, 29.3, 29.2, 27.4, 16.1

Example T38

Standard Procedure for the Synthesis of Tether T38

Figure 13:
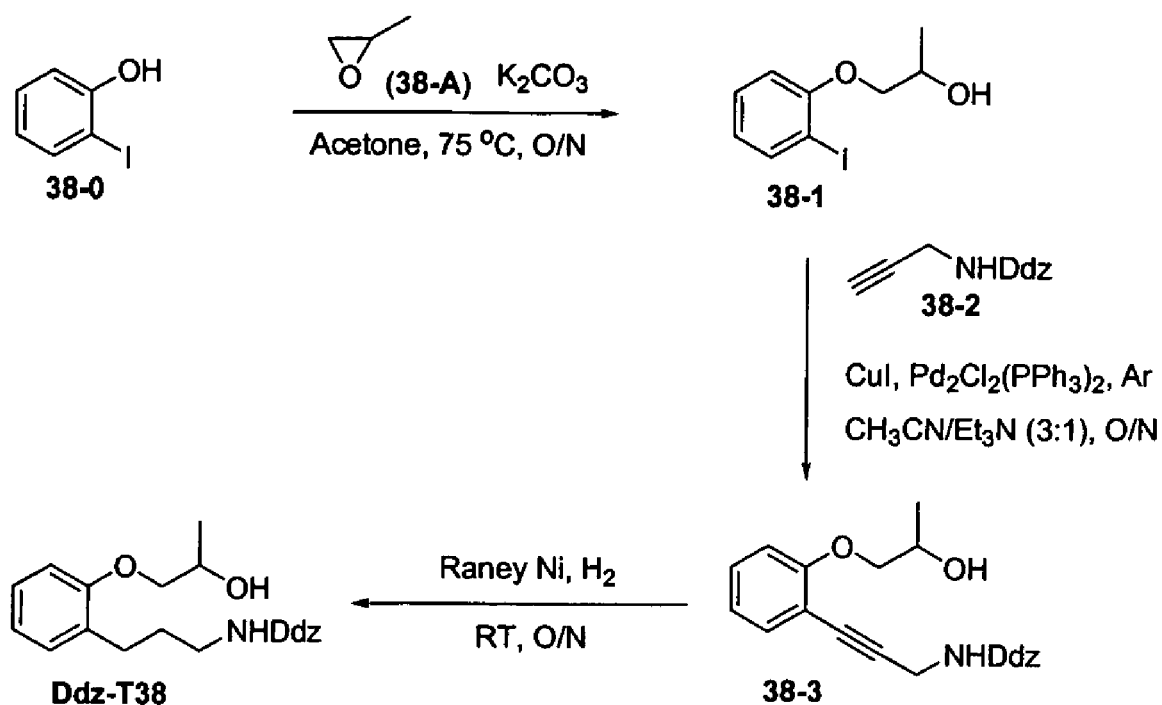

An outline of the synthetic scheme for racemic material is shown in FIG. 13. The enatiomers are accessed through the use of the optically pure propylene oxide enantiomers. Since the center of the epoxide is inverted during the protocol, the (R)-epoxide provides T38(S), while the (S)-epoxide provides T38(R).

$^1$H NMR (CDCl$_3$): δ 7.20-7.10, (m, 2H), 6.95-9.80 (m, 2H), 6.55 (bs, 2H), 6.35 (s, 1H), 5.18 (bt, 1H), 4.12 (m, 1H), 3.98 (m, 2H), 3.80 (s, 6H), 3.15 (bq, 2H), 2.65 (t, 2H), 1.98 (bs, 2H), 1.65 (bs, 6H), 1.25 (m, 3H).

Example T39

Standard Procedure for the Synthesis of Tether T39

Figure 14:
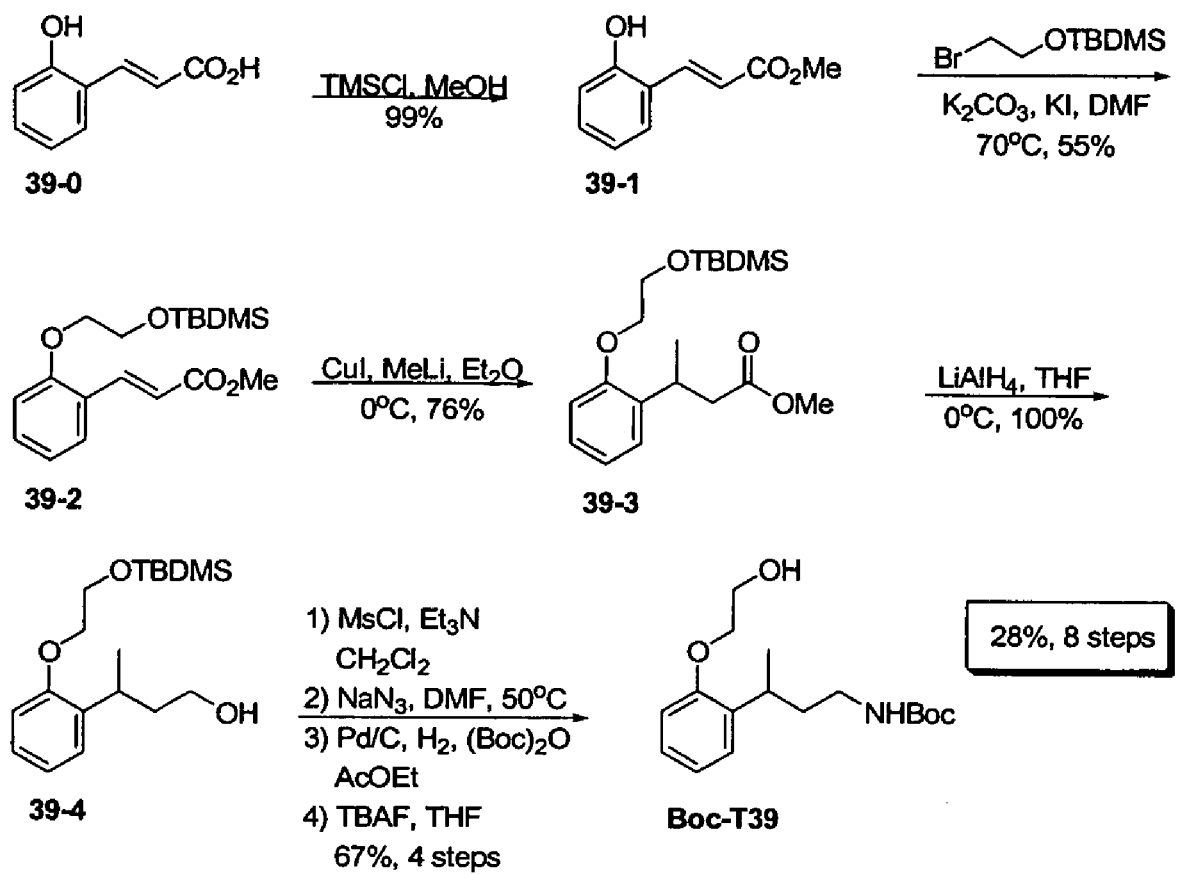

See FIG. 14 for an outline of the synthetic scheme for racemic product. Enantiomeric versions can be accessed via resolution methodologies or use of an asymmetric Michael addition in the third step.

$^1$H NMR (CDCl$_3$): δ 7.11-7.08 (2H, m), 6.86 (1H, t), 6.76 (1H, d), 5.05 (1H, broad), 4.26-3.85 (4H, m), 3.22-3.07 (2H, m), 2.71 (1 H, broad), 1.66-1.60 (2H, m),1.33 (9H, s), 1.17 (3H, d). 13C NMR (CDCl$_3$): δ 156.1, 135.0, 127.1, 127.0, 121.4, 111.7, 69.9, 61.5, 39.8, 38.4, 28.7, 20.7.

Example T40

Standard Procedure for the Synthesis of Tether T40

Figure 15:
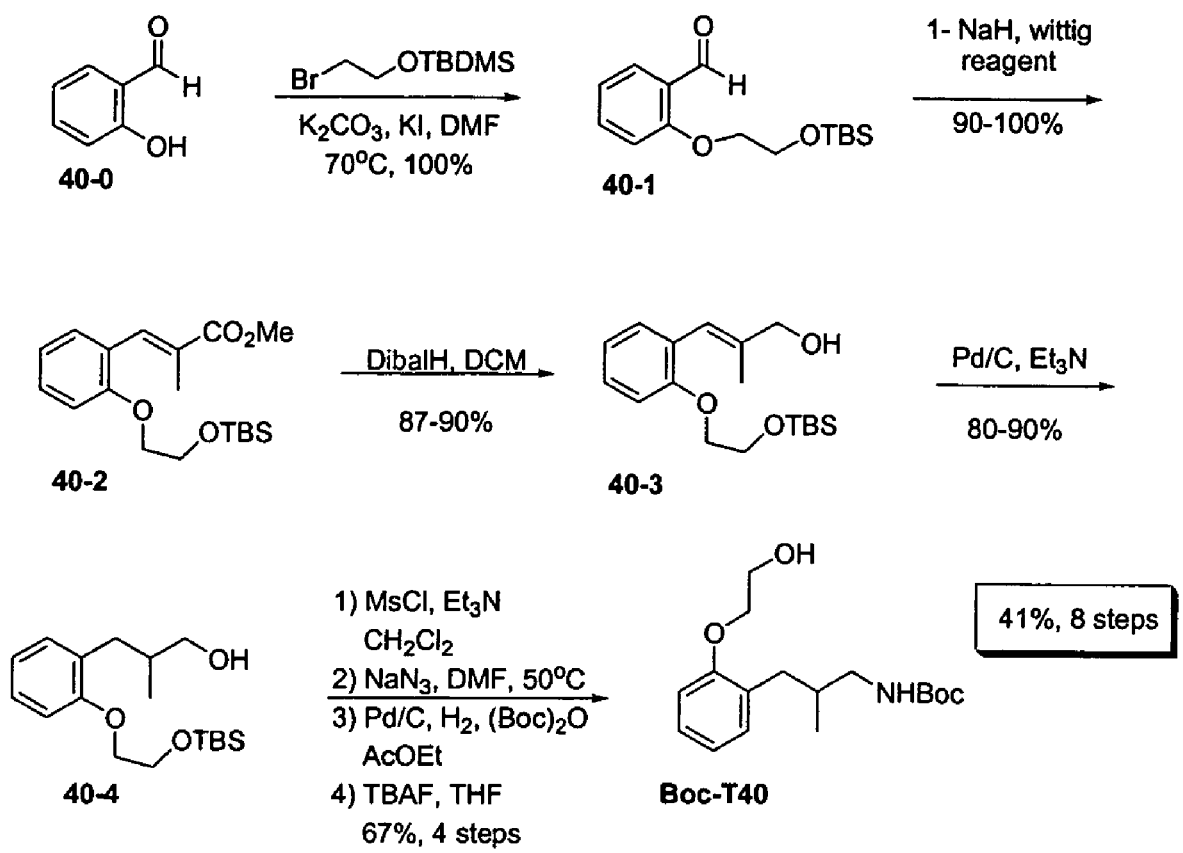
Figure 16:
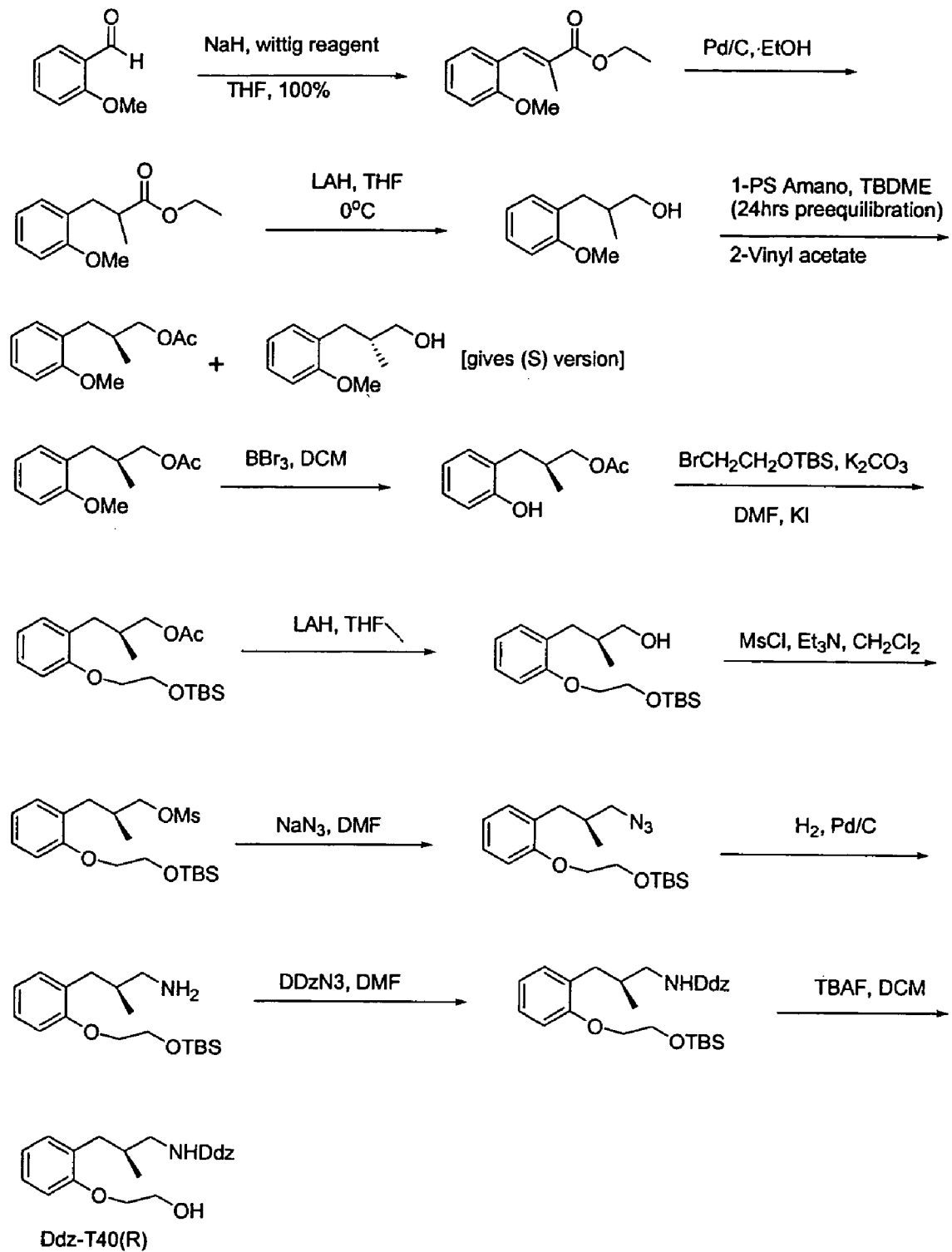

An outline of the synthetic scheme for racemic material is shown in FIG. 15, while FIG. 16 outlines the route to both enantiomers involving an enzymatic resolution as the key step.

$^1$H NMR (CDCl$_3$): δ 7.11-7.08 (2H, m), 6.86 (1H, t), 6.76 (1H, d), 5.05 (1H, broad), 4.26-3.85 (4H, m), 3.22-3.07 (2H, m), 2.71 (1H, broad), 1.66-1.60 (2H, m), 1.33 (9H, s), 1.17 (3H, d). $^{13}$C NMR (CDCl$_3$): δ 156.1, 135.0, 127.1, 127.0, 121.4, 111.7, 69.9, 61.5, 39.8, 38.4, 28.7, 20.7.

Example T41

Standard Procedure for the Synthesis of Tether T41

Figure 17A:
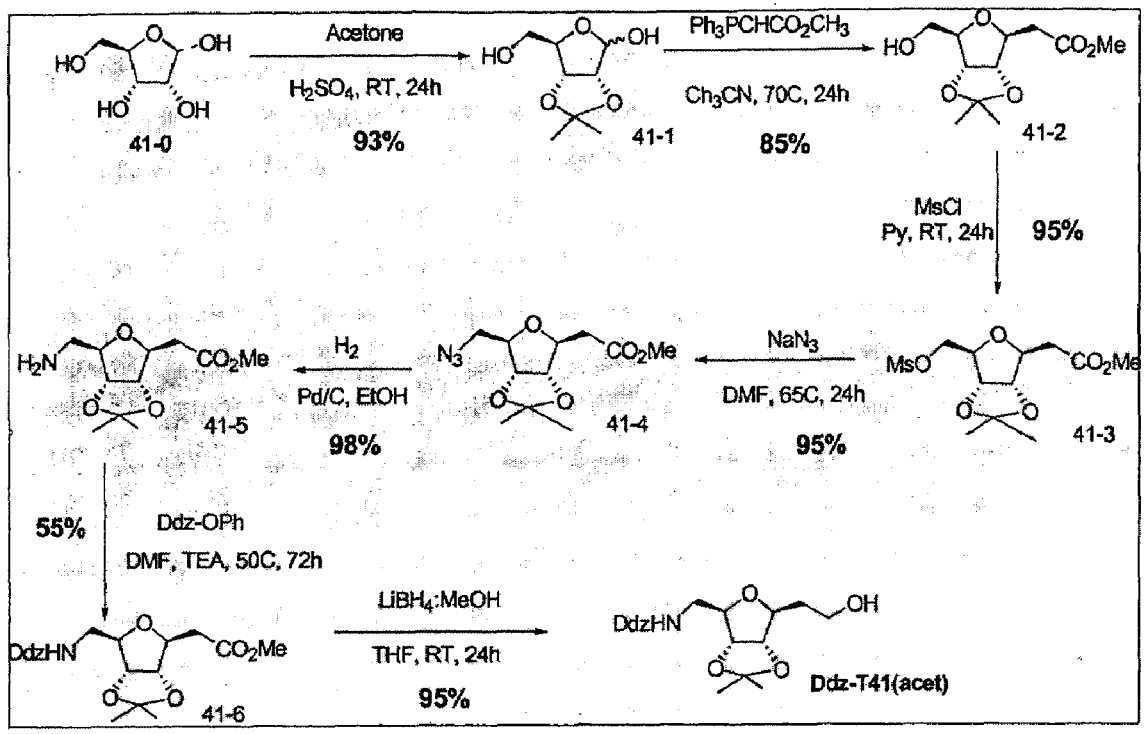
Figure 17B:
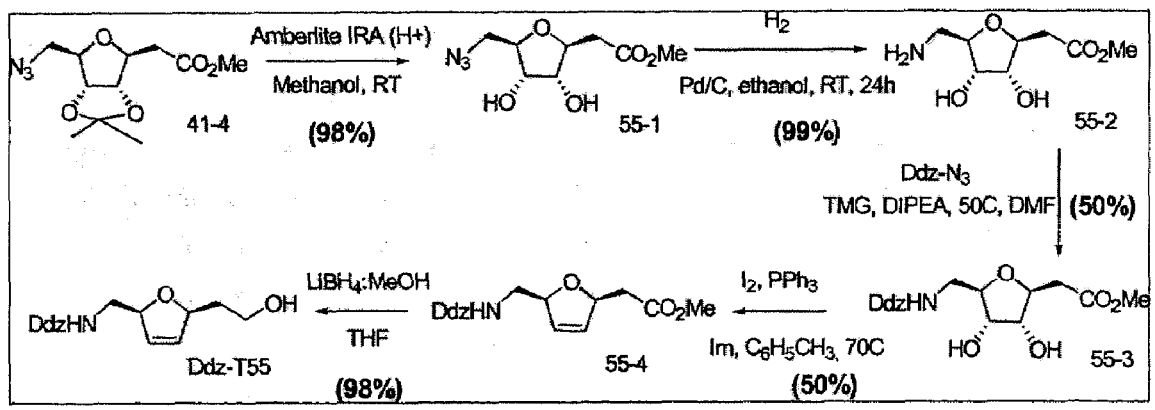
Figure 17C:
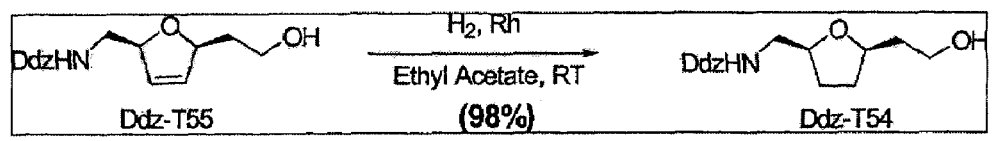
Figure 18:
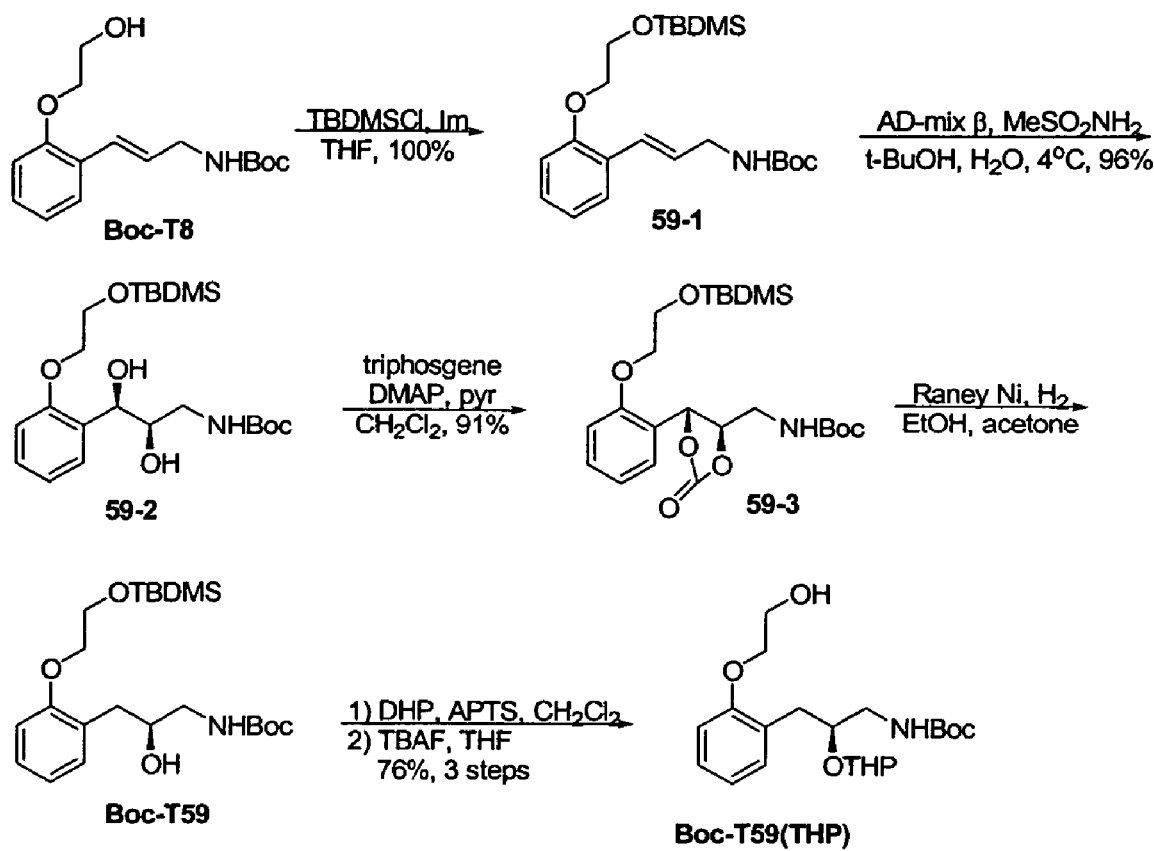
Figure 19:
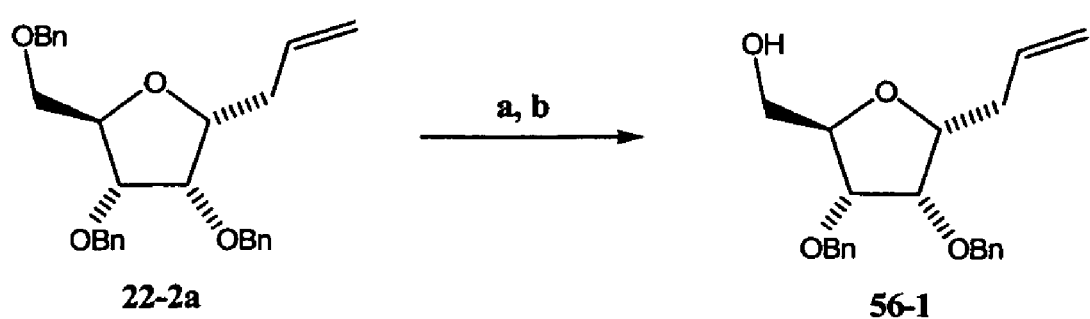

See FIG. 17(*a*) for an outline of the synthetic scheme that provides an appropriately protected derivative for use in macrocycle construction via FIG. 1.

$^1$H NMR (CDCl$_3$): δ 1.23 (s, 3H), 1.49 (s, 3H), 1.69 (s, 3H), 1.74 (s, 3H), 1.90 (m, 2H), 2.35 (m, 1H), 3.35 (m, 2H), 3.76 (s, 6H), 3.92 (m, 2H), 4.40 (m, 2H), 5.10 (m, 1H), 6.15 (s, 1H), 6.25 (s, 2H). $^{13}$C NMR (CDCl$_3$): δ 25.52 (CH$_3$), 27.53 (CH$_3$), 28.88 (CH$_3$), 29.61 (CH$_3$), 35.92 (CH$_2$), 42.62 (CH$_2$), 55.43 (CH$_3$), 60.60 (CH$_2$), 82.38 (CH), 83.33 (CH), 83.68 (CH), 84.96 (CH), 98.26 (CH), 103.23 (CH), 118.3 (Cq), 149.50 (Cq), 156.20 (Cq), 160, 02 (Cq) MW Calcd. for C$_{22}$H$_{33}$NO$_8$: 439.50; MS Found: (M+H)$^+$ 440

Example T54

Standard Procedure for the Synthesis of Tether T54

See FIG. 17(*c*) for an outline of the synthetic scheme from a T55 derivative.

$^1$H NMR (CDCl$_3$): δ 1.55 (m, 2H), 1.72 (s, 6H), 1.8-2.01 (m, 4H), 2.75 (s$_b$, 1H), 3.10 (m, 1H), 3.32 (m, 1H), 3.65 (s, 6H), 3.66 (m, 2H), 3.90-4.01 (m, 2H), 5.30 (m, 1H), 6.30 (s, 1H), 6.50 (s, 2H). $^{13}$C NMR (CDCl$_3$): δ 28.04 (CH$_2$), 29.18 (CH$_3$), 29.34 (CH$_3$), 31.69 (CH$_2$), 38.08 (CH$_2$), 44.94 (CH$_2$), 55.41 (CH$_3$), 61.28 (CH$_2$), 78.84 (CH), 79.41 (CH), 80.75 (Cq), 98.44 (CH), 103.15 (CH), 149.44 (Cq), 155.64 (Cq), 160.81 (Cq). MW Calcd. for C$_{19}$H$_{29}$NO$_6$: 367.44; MS Found: (M+H)$^+$ 368

Example T55

Standard Procedure for the Synthesis of Tether T55

See FIG. 17(*b*) for an outline of the synthetic scheme.

$^1$H NMR (CDCl$_3$): δ 1.66 (s, 3H), 1.71 (s, 3H), 1.82 (m, 1H), 1.89 (m, 1H), 3.26 (m, 2H), 3.77 (s, 6H), 3.80 (m, 2H), 4.84 (m, 1 H), 4.95 (m, 1 H), 5.20 (m, 1 H), 5.70 (m, 1H), 5.85 (m,1H), 6.32 (s, 1H), 6.49 (s, 2H). $^{13}$C NMR (CDCl$_3$): δ 29.06 (CH$_3$), 29.42 (CH$_3$), 38.73 (CH$_2$), 44.87 (CH$_2$), 55.45 (CH$_3$), 61.01 (CH$_2$), 80.77 (Cq), 85.84 (CH), 86.25 (CH), 98.28 (CH), 103.28 (CH), 127.84 (CH), 131.95 (CH), 149.42 (Cq), 155.59 (Cq), 160.79 (Cq). MW Calcd. for C$_{19}$H$_{27}$NO$_6$: 365.42; MS Found: (M+H)$^+$ 366

Example T56

Standard Procedure for the Synthesis of Precursor (56-1) for Tethers T56 and T57

Figure 2:
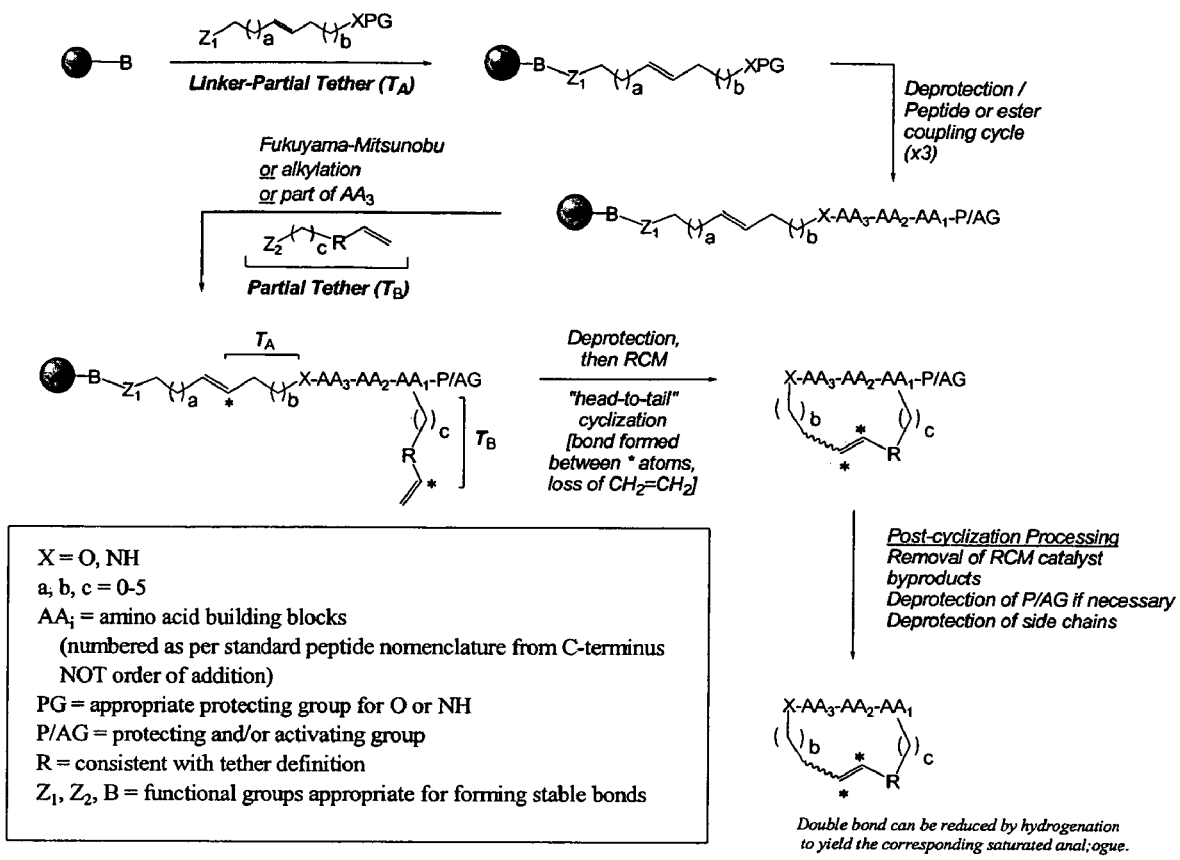

For some of the tether structures, specifically those arising from the ring-closing metathesis methodology (RCM, FIG. 2), the tether is not added as an already assembled unit, but is constructed during the macrocyclization reaction from appropriate precursor pieces. One such example id shown in FIG. 19 in which 56-1, containing a pendant alkene moiety, will be subjected to RCM whereby the alkene will join with an alkene in another part of the substrate to form the macrocyclic ring and, hence, construct tether T56 (or homologues). Reduction of the double bond in macrocycles containing T56 leads to macrocycles containing T57. Other tethers that were constructed in this manner include T46, T47, T49, and T51.

Table 1 lists the structural features for 60 preferred embodiments of compounds of formula (I).

Table 2 gives the Mass Spectrum analytical data for these compounds.

TABLE 1

Representative Compounds of formula (I)

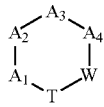

(I)

W is NH except for compounds 229 to 232 where W is O.

| Cmpd | A₁ | A₂ | A₃ | T* |
|---|---|---|---|---|
| 201 | 3-CF₃-benzyl (S) | Val | Arg | T40(S) |
| 202 | 3-F-benzyl (S) | Val | N,N-dimethyl-Dap | T40(S) |
| 203 | 3-Cl-benzyl (S) | Val | Arg | T38(S) |
| 204 | 3-CF₃-benzyl (S) | Val | Arg | T40(R) |
| 205 | 3-F-benzyl (S) | Val | N,N-dimethyl-Dap | T40(R) |
| 206 | 3-Cl-benzyl (S) | Val | Arg | T38(R) |

| | 21 | 22 | |
|---|---|---|---|
| 207 | 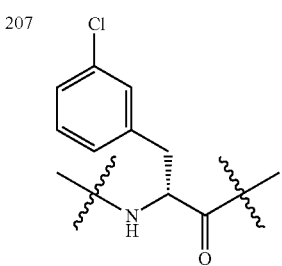 | 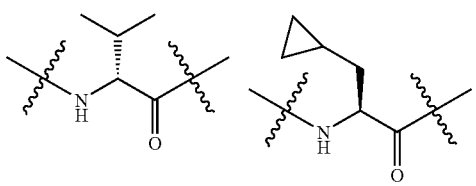 | T40(S) |
| 208 | 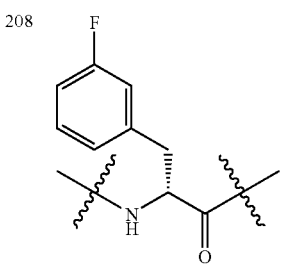 | 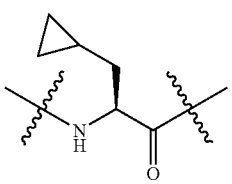 | T38(S) |
| 209 | 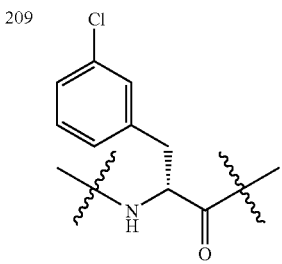 | 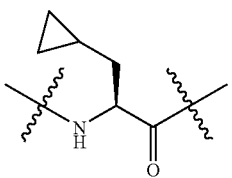 | T40 |
| 210 | 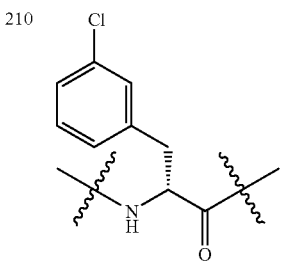 | 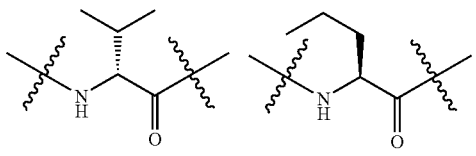 | T39 |
| 211 | 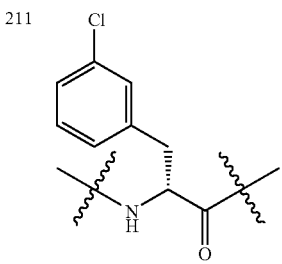 | 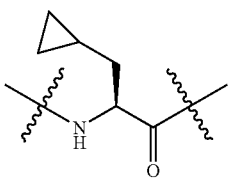 | T40(R) |
| 212 | 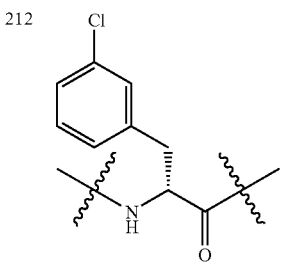 | 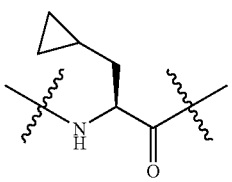 | T58 |

| | | | |
|---|---|---|---|
| 213 | 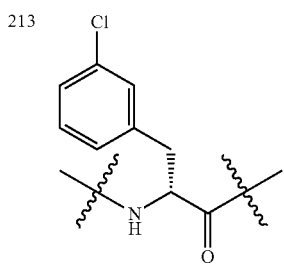 | 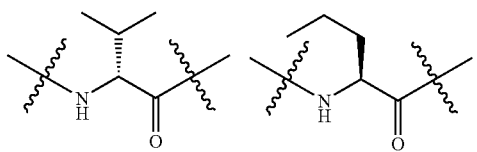 | T39 |
| 214 | 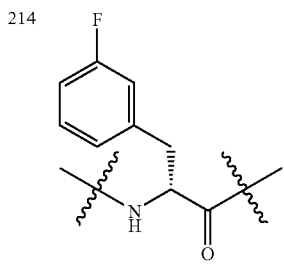 | 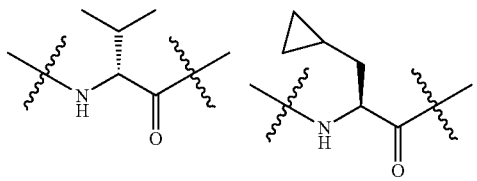 | T40(R) |
| 215 | 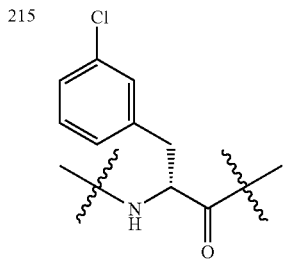 | 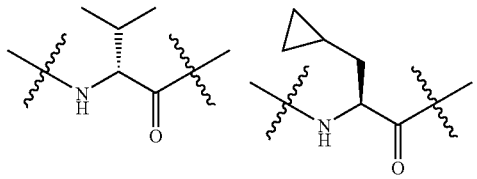 | T59(S) |
| 216 | 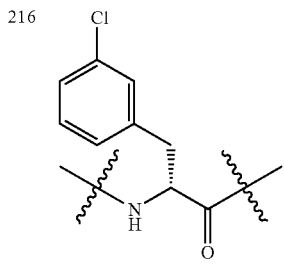 | 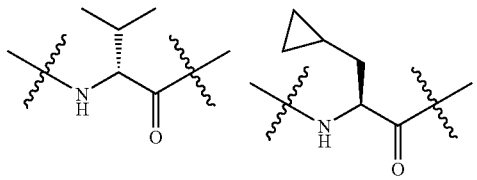 | T59(R) |
| 217 | 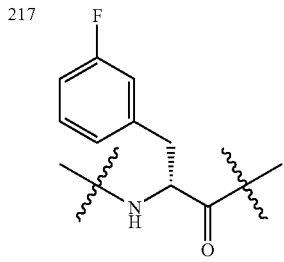 | 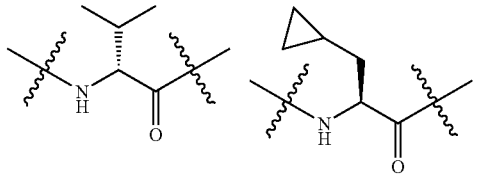 | T38(R) |
| 218 | 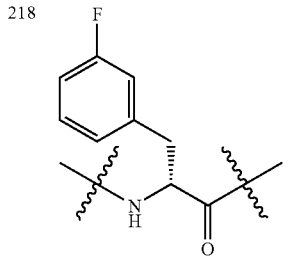 | 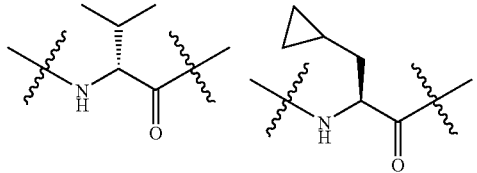 | T59(S) |

| | 25 | 26 | |
|---|---|---|---|
| 219 | 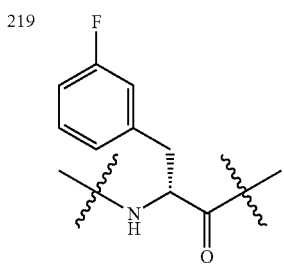 | 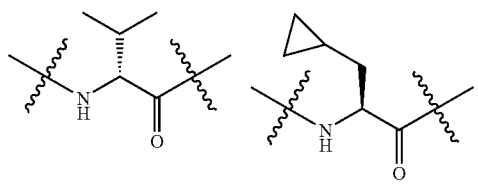 | T59(R) |
| 220 | 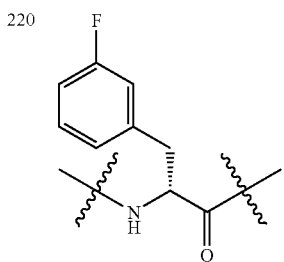 | 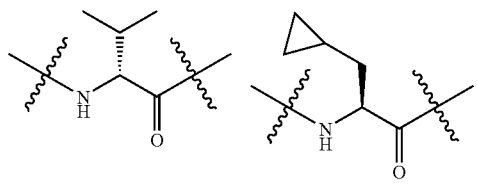 | T33(R) |
| 222 | 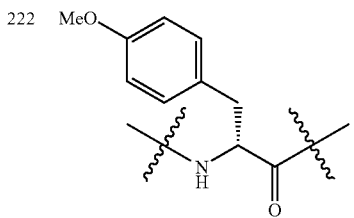 | 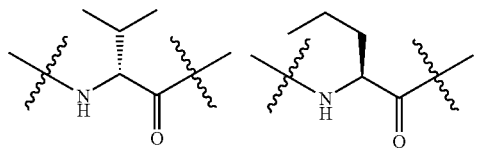 | T38 |
| 223 | 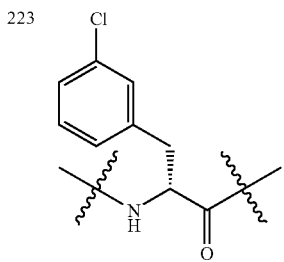 | 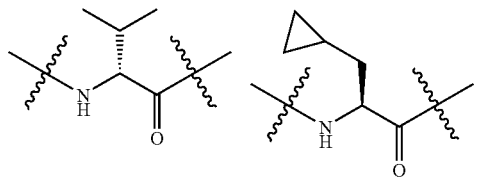 | T38 |
| 224 | 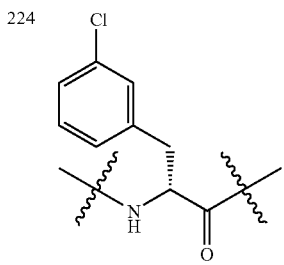 | 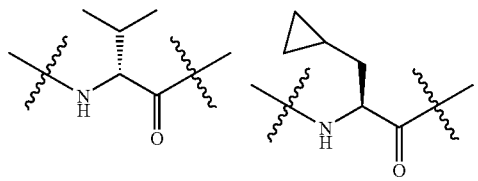 | T41 |
| 225 | 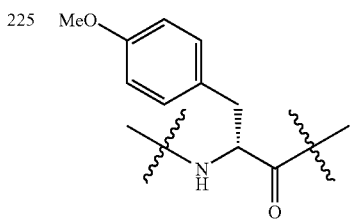 | 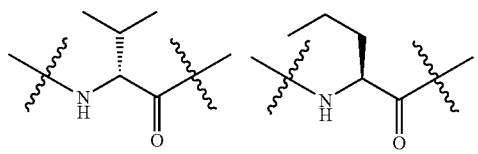 | T41 |

| | | | |
|---|---|---|---|
| 226 | 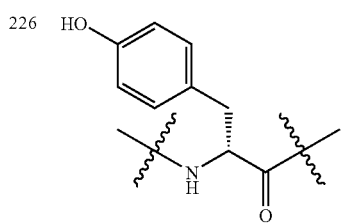 | 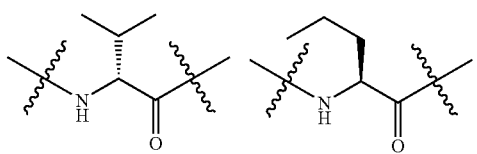 | T33(S) |
| 227 | 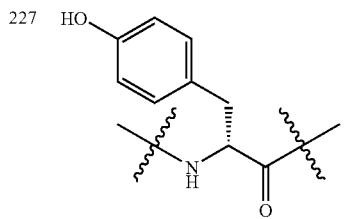 | 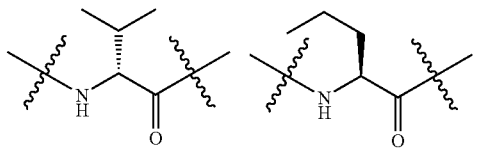 | T33(R) |
| 228 | 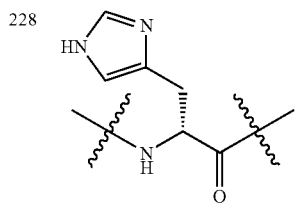 | 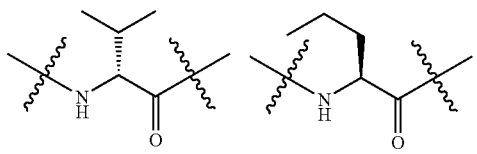 | T12 |
| 229 | 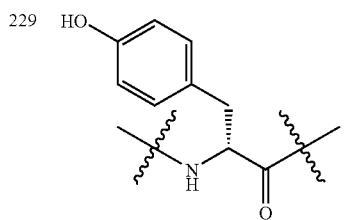 | 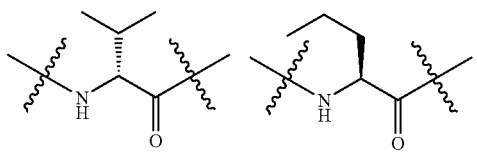 | T56(Y = H) |
| 230 | 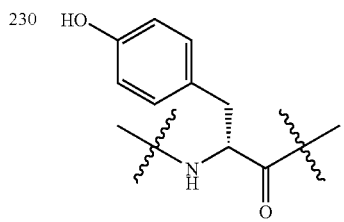 | 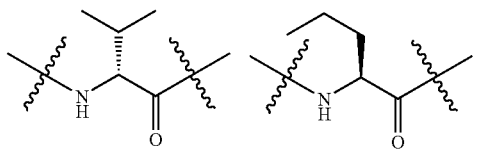 | T57(Y = H) |
| 231 | 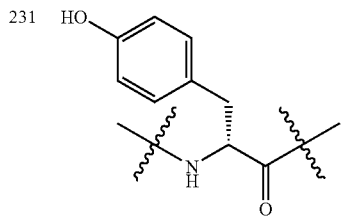 | 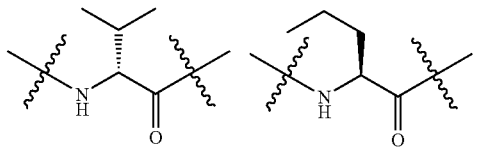 | T56(Y = Me) |
| 232 | 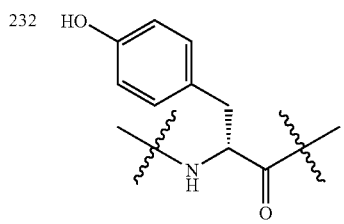 | 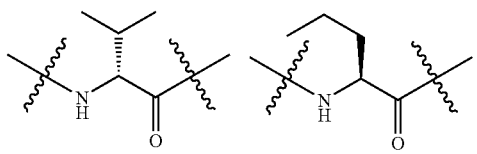 | T57(Y = Me) |

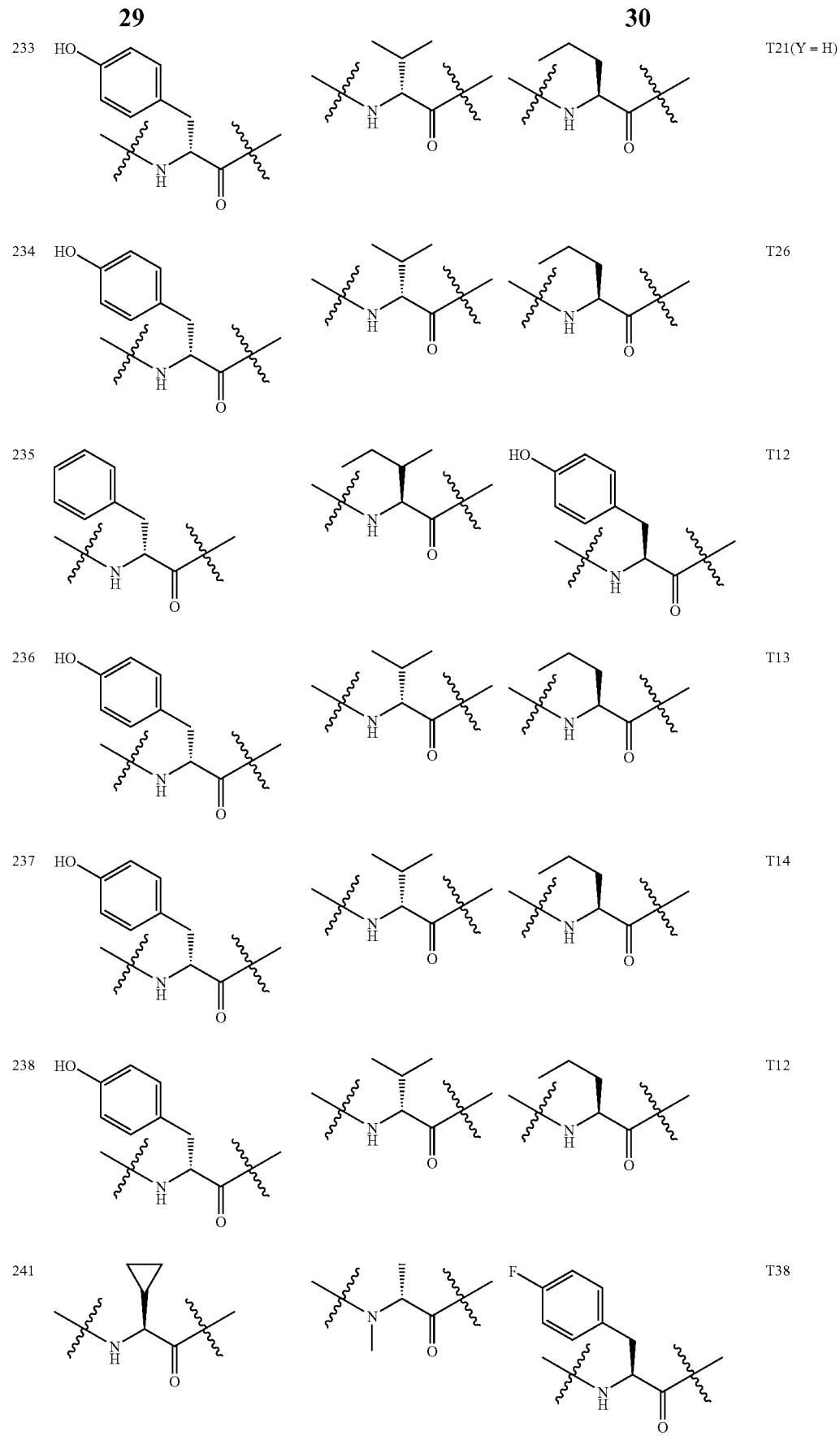

| | | | |
|---|---|---|---|
| 242 | 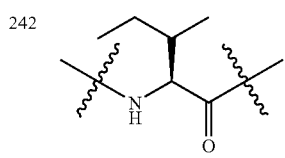 | 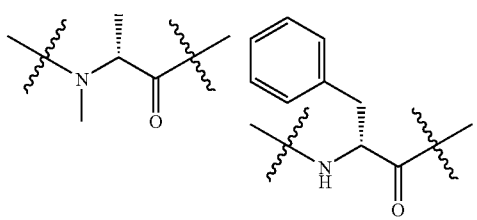 | T33(R) |
| 243 | 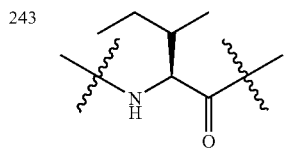 | 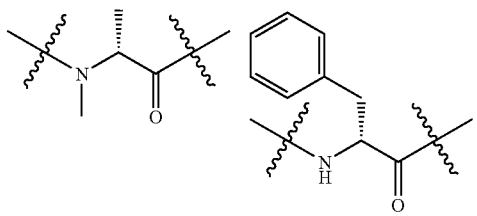 | T33(S) |
| 244 | 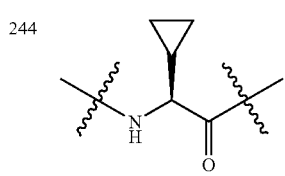 | 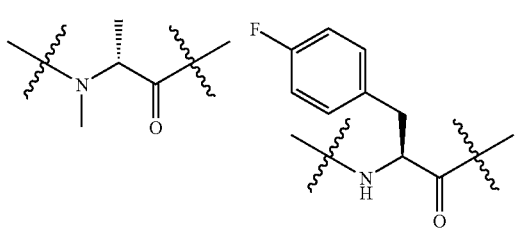 | T33(R) |
| 245 | 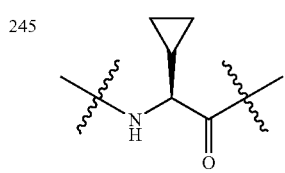 | 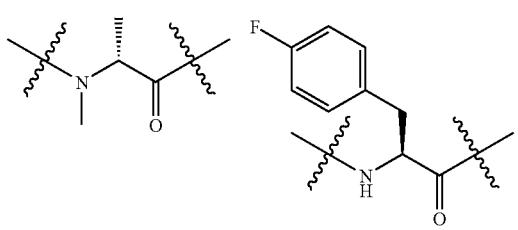 | T33(S) |
| 246 | 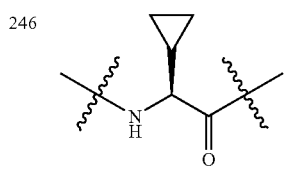 | 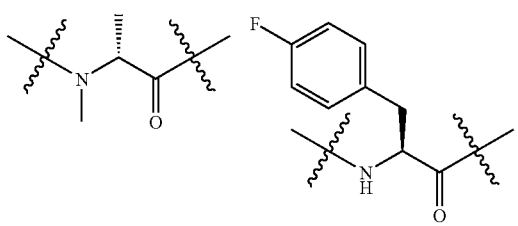 | T39 |
| 247 | 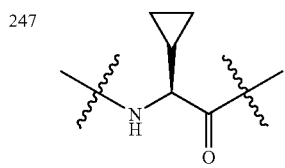 | 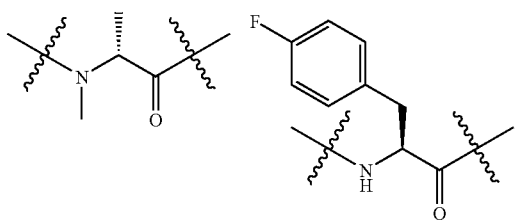 | T58 |
| 248 | 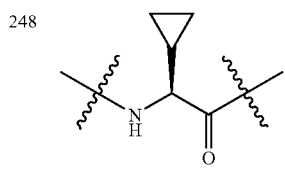 | 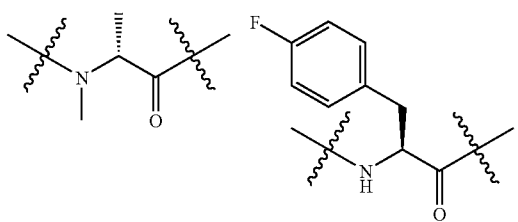 | T40 |

| | 33 | 34 | |
|---|---|---|---|
| 249 | 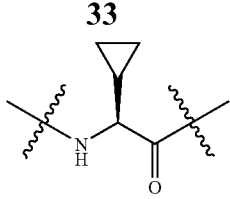 | 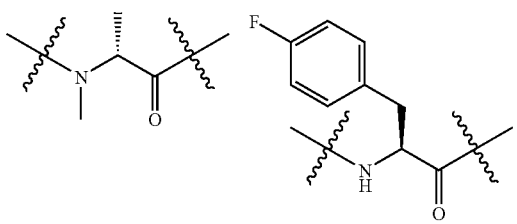 | T21(Y = H) |
| 250 | 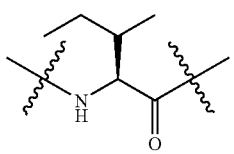 | 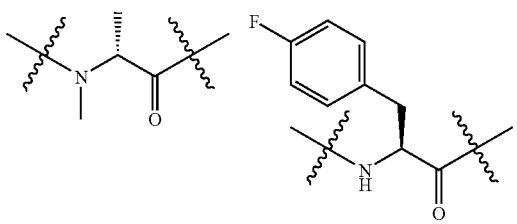 | T24 |
| 251 | 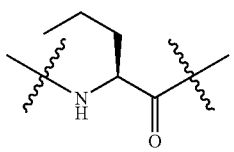 | 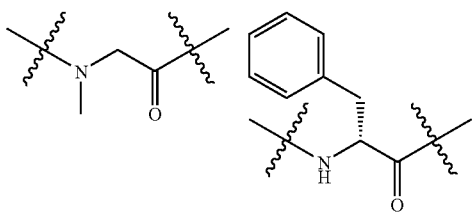 | T12 |
| 252 | 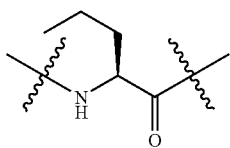 | 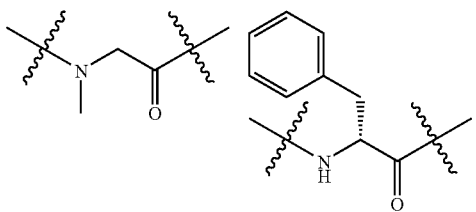 | T27 |
| 253 | 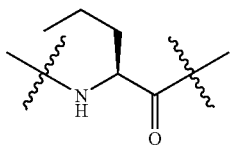 | 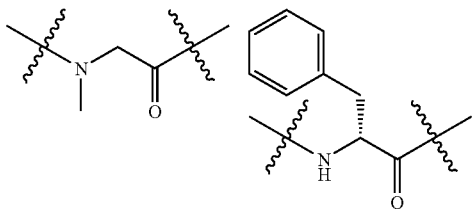 | T14 |
| 254 | 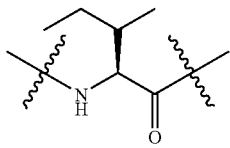 | 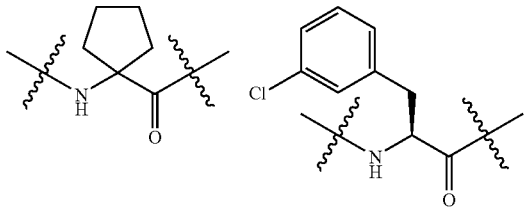 | T33(R) |
| 255 | 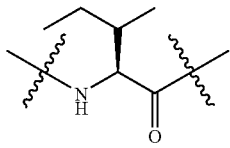 | 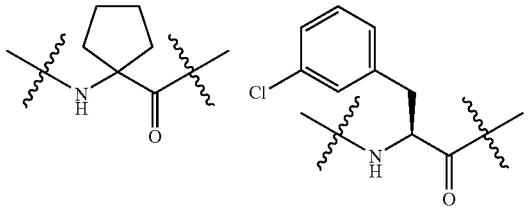 | T33(S) |

| | | | |
|---|---|---|---|
| 256 | 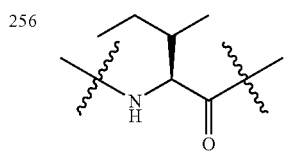 | 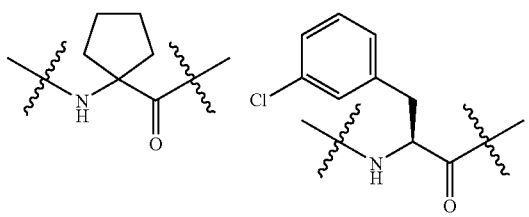 | T39 |
| 257 | 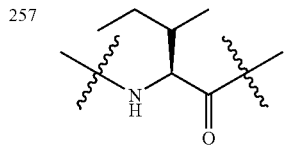 | 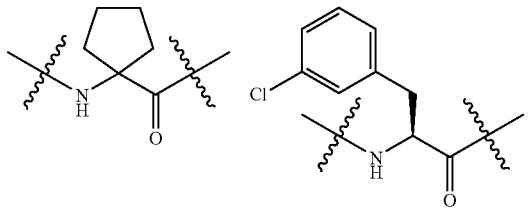 | T40 |
| 258 | 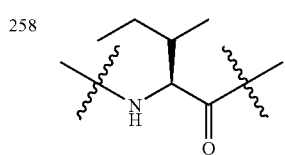 | 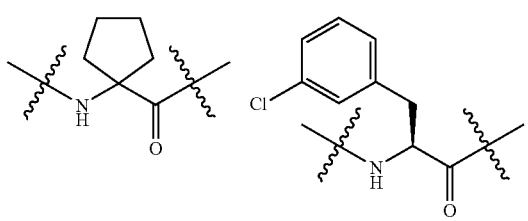 | T58 |
| 259 | 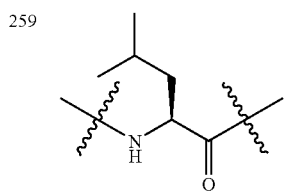 | 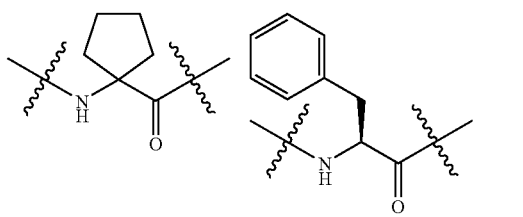 | T12 |
| 260 | 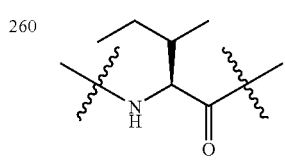 | 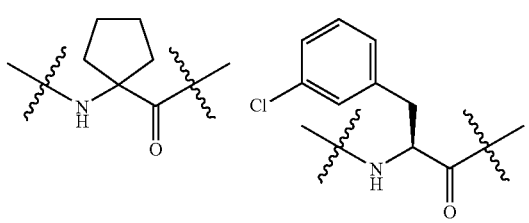 | T46 |
| 261 | 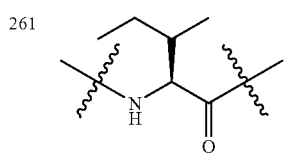 | 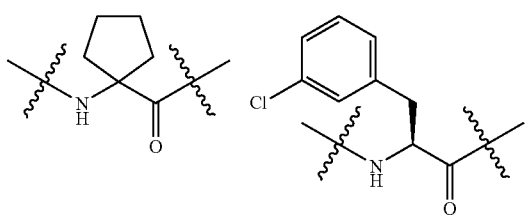 | T47 |
| 262 | 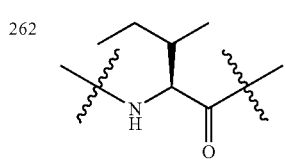 | 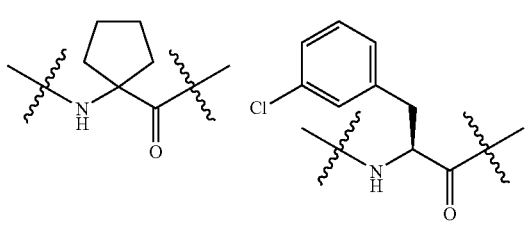 | T49 |

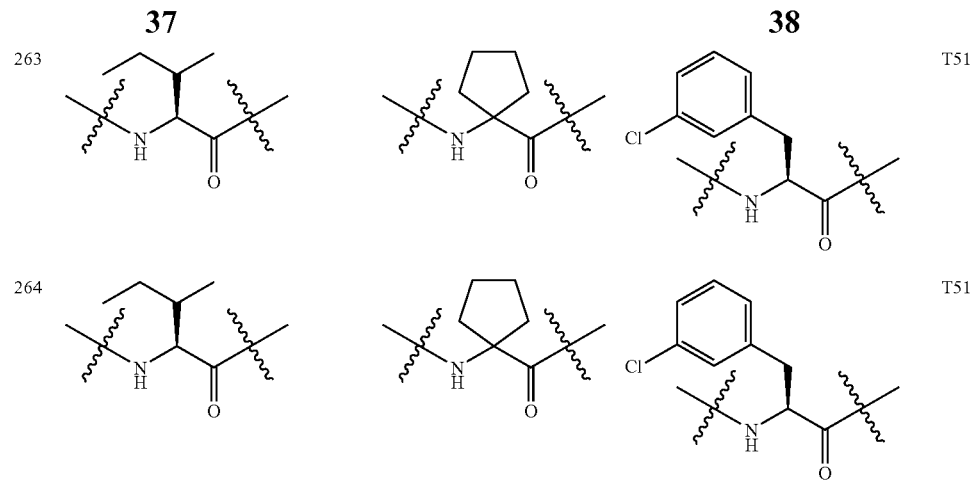

*Designation in parentheses indicates the absolute configuration (R or S) of the chiral center on the tether. If no configuration is so designated, the center is racemic. Other designations indicate the identity of a variable substituent.

TABLE 2

Mass Spectral Analyses for Representative Compounds of formula I

| Cmpd | Molecular Formula | Molecular Weight | Monoisotopic Mass | MS Found (M + H)+ |
|---|---|---|---|---|
| 201 | C31H42N7O4F3 | 633.7 | 633 | 634 |
| 202 | C31H44N5O4F | 569.7 | 569 | 570 |
| 203 | C30H42N7O4Cl | 600.2 | 599 | 600 |
| 204 | C31H42N7O4F3 | 633.7 | 633 | 634 |
| 205 | C31H44N5O4F | 569.7 | 569 | 570 |
| 206 | C30H42N7O4Cl | 600.2 | 599 | 600 |
| 207 | C32H43N4O4Cl | 583.2 | 582 | 583 |
| 208 | C32H43N4O4F | 566.7 | 566 | 567 |
| 209 | C32H43N4O4Cl | 583.2 | 582 | 583 |
| 210 | C31H43N4O4Cl | 571.2 | 570 | 571 |
| 211 | C32H43N4O4Cl | 583.2 | 582 | 583 |
| 212 | C33H45N4O4Cl | 597.2 | 596 | 597 |
| 213 | C31H43N4O4F | 554.7 | 554 | 555 |
| 214 | C32H43N4O4F | 566.7 | 566 | 567 |
| 215 | C31H41N4O5Cl | 585.1 | 584 | 585 |
| 216 | C31H41N4O5Cl | 585.1 | 584 | 585 |
| 217 | C32H43N4O4F | 566.7 | 566 | 567 |
| 218 | C31H41N4O5F | 568.7 | 568 | 569 |
| 219 | C31H41N4O5F | 568.7 | 568 | 569 |
| 220 | C32H43N4O4F | 566.7 | 566 | 567 |
| 222 | C32H46N4O5 | 566.7 | 566 | 567 |
| 223 | C32H43N4O4Cl | 583.2 | 582 | 583 |
| 224 | C27H39N4O6Cl | 551.1 | 550 | 551 |
| 225 | C27H42N4O7 | 534.6 | 534 | 535 |
| 226 | C31H44N4O5 | 552.7 | 552 | 553 |
| 227 | C31H44N4O5 | 552.7 | 552 | 553 |
| 228 | C30H38N6O3S | 562.7 | 562 | 563 |
| 229 | C28H41N3O8 | 547.6 | 547 | 548 |
| 230 | C28H43N3O8 | 549.7 | 549 | 550 |
| 231 | C30H45N3O8 | 575.7 | 575 | 576 |
| 232 | C30H47N3O8 | 577.7 | 577 | 578 |
| 233 | C25H38N4O7 | 506.6 | 506 | 507 |
| 234 | C25H36N4O5 | 472.6 | 472 | 473 |
| 235 | C38H42N4O4S | 650.8 | 650 | 651 |
| 236 | C24H33N5O5 | 471.5 | 471 | 472 |
| 237 | C24H33N5O4S | 487.6 | 487 | 488 |
| 238 | C33H40N4O4S | 588.8 | 588 | 589 |
| 241 | C30H39N4O4F | 538.7 | 538 | 539 |
| 242 | C31H44N4O4 | 536.7 | 536 | 537 |
| 243 | C31H44N4O4 | 536.7 | 536 | 537 |
| 244 | C30H39N4O4F | 538.7 | 538 | 539 |
| 245 | C30H39N4O4F | 538.7 | 538 | 539 |
| 246 | C30H39N4O4F | 538.7 | 538 | 539 |
| 247 | C31H41N4O4F | 552.7 | 552 | 553 |
| 248 | C30H39N4O4F | 538.7 | 538 | 539 |
| 249 | C24H33N4O6F | 492.5 | 492 | 493 |
| 250 | C26H41N4O3F | 476.6 | 476 | 477 |
| 251 | C31H36N4O3S | 544.7 | 544 | 545 |

TABLE 2-continued

Mass Spectral Analyses for Representative Compounds of formula I

| Cmpd | Molecular Formula | Molecular Weight | Monoisotopic Mass | MS Found (M + H)+ |
|---|---|---|---|---|
| 252 | C23H34N4O4 | 430.5 | 430 | 431 |
| 253 | C22H29N5O3S | 443.6 | 443 | 444 |
| 254 | C33H45N4O4Cl | 597.2 | 596 | 597 |
| 255 | C33H45N4O4Cl | 597.2 | 596 | 597 |
| 256 | C33H45N4O4Cl | 597.2 | 596 | 597 |
| 257 | C33H45N4O4Cl | 597.2 | 596 | 597 |
| 258 | C34H47N4O4Cl | 611.2 | 611 | 612 |
| 259 | C35H42N4O3S | 598.8 | 598 | 599 |
| 260 | C23H35N4O3F | 434.5 | 434 | 435 |
| 261 | C26H39N4O3Cl | 491.1 | 490 | 491 |
| 262 | C27H41N4O3Cl | 505.1 | 504 | 505 |
| 263 | C28H43N4O3Cl | 519.1 | 518 | 519 |
| 264 | C29H45N4O3Cl | 533.1 | 532 | 533 |

Notes
1. Molecular formulas and molecular weights (MW) are calculated automatically from the structure via ActivityBase ® software (ID Business Solution, Ltd., Guildford, Surrey, UK) or, for MW only, from the freeware program Molecular Weight Calculator v. 6.32
2. M + H obtained from LC-MS analysis
3. All analyses conducted on material after preparative purification Biological Evaluation for Compounds of the Invention The compounds of the present invention were evaluated for their ability to interact at the human motilin receptor and the human ghrelin receptor utilizing competitive redioligand binding assays as described in Method B1 and B2, respectively. Further characterization of the interaction can be performed utilizing the functional assays described in Methods B3 and B4 for the motilin and ghrelin receptors, respectively. All of these methods can be conducted, if so desired, in a high throughput manner to permit the simultaneous evaluation of many compounds.

Results for the examination of representative compounds of the present invention using Methods B1 and B2 are presented in Table 3.

Example Method B1

Competitive Radioligand Binding Assay (Motilin Receptor)

Materials:

Membranes were prepared from CHO cells stably transfected with the human motilin receptor and utilized at a quantity of 1.5 µg/assay point. [PerkinElmer™ SignalScreen® Product #6110544, PerkinElmer, Inc. Wellesley, MA]

[$^{125}$I]-Motilin (PerkinElmer, #NEX-378); final concentration: 0.04-0.06 nM

Motilin (Bachem™, #H-4385, Bachem Bioscience Inc., King of Prussia, PA.); final concentration: 1 µM Multiscreen® Harvest plates-GF/B (Millipore™, #MAHFB1H60, Billerica, MA)

Deep-well polypropylene titer plate (Beckman Coulter™, #267006, Fullerton, CA)

TopSeal-A™ (PerkinElmer, #6005185, Wellesley, MA)

Bottom seal (Millipore, #MATAH0P00)

MicroScint-0™(PerkinElmer,#6013611, Wellesley, MA)

Binding Buffer: 50 mM Tris-HCl (pH 7.4), 10 mM MgCl$_2$, 1 mM EDTA, 0.1% BSA

Assay Volumes:
  150 µL of membranes diluted in binding buffer
  10 µL of compound diluted in binding buffer
  10 µL of radioligand ([$^{125}$I]-Motilin) diluted in binding buffer Final Test Concentrations (N=11) for Compounds:
  10, 5, 2, 1, 0.5, 0.2, 0.1, 0.05, 0.02, 0.01, 0.005 µM.

Compound Handling:
  Compounds were provided frozen on dry ice at a stock concentration of 10 mM diluted in 100% DMSO and stored at −20° C. until the day of testing. On the test day, compounds were allowed to thaw at room temperature and than diluted in assay buffer according to the desired test concentrations. Under these conditions, the maximum final DMSO concentration in the assay was 0.5%.

Assay Protocol:
  In deep-well plates, diluted cell membranes (1.5 µg/mL) are combined with 10 µL of either binding buffer (total binding, N=5), 1 µM motilin (non-specific binding, N=3) or the appropriate concentration of test compound. The reaction is initiated by addition of 10 µl of [$^{125}$I]-motilin (final conc. 0.04-0.06 nM) to each well. Plates are sealed with TopSeal-A™, vortexed gently and incubated at room temperature for 2 hours. The reaction is arrested by filtering samples through pre-soaked (0.3% polyethyleneimine, 2 h) Multiscreen®Harvest plates using a Tomtec® Harvester (Tomtec, Hamden, CT), washed 9 times with 500 µL of cold 50 mM Tris-HCl (pH 7.4), and than plates are air-dried in a fumehood for 30 minutes. A bottom seal is applied to the plates prior to the addition of 25 µL of MicroScint-0 ® to each well. Plates are then sealed with TopSeal-A™ and counted for 30 sec per well on a TopCount® Microplate Scintillation and Luminescence Counter (PerkinElmer, Wellesley, MA) where results are expressed as counts per minute (cpm).

Data are analyzed by GrapbPad™ Prism® (GraphPad Software, San Diego, CA) using a variable slope non-linear regression analysis. K$_i$ values were calculated using a K$_d$ value of 0.16 nM for [$^{125}$I]-motilin (previously determined during membrane characterization).

$$D_{\max} = 1 - \frac{\text{test concentration with maximal displacement} - \text{non-specific binding}}{\text{total binding} - \text{non-specific binding}} \times 100$$

where total and non-specific binding represent the cpm obtained in the absence or presence of 1 µM motilin, respectively.

Example Method B2

Competitive Radioligand Binding Assay (Ghrelin Receptor)

The competitive binding assay at the human growth hormone secretagogue receptor (hGHS-R1a) was carried out analogously to assays described in the literature. (Bednarek M A et al. (2000), Structure-function studies on the new growth hormone-releasing peptide ghrelin: minimal sequence of ghrelin necessary for activation of growth hormone secretagogue receptor 1 a; J Med Chem 43:43704376. Palucki B L et al. (2001), Spiro(indoline-3,4'-piperidine) growth hormone secretagogues as ghrelin mimetics; Bioorg Med Chem Lett 11:1955-1957.)

Materials
  Membranes (GHS-R/HEK 293) were prepared from HEK-293 cells stably transfected with the human ghrelin receptor (hGHS-R1a). These membranes were provided by PerkinElmer BioSignal® (#RBHGHSM, lot#1887, PerkinlElmer, Wellesley, MA) and utilized at a quantity of 0.71 µg/assay point.
  [$^{125}$I]-Ghrelin (PerkinElmer, #NEX-388); final concentration: 0.0070-0.0085 nM
  Ghrelin(Bachem, #H-4864, Bachem Bioscience Inc., King of Prussia, PA); final concentration: 1 µM
  Multiscreen® Harvest plates-GF/C (Millipore, #MAHFC1H60, Billerica, MA)
  Deep-well polypropylene titer plate (Beckman Coulter, #267006, Fullerton, CA)
  TopSeal-A™ (PerkinElmer, #6005185, Wellesley, MA)
  Bottom seal (Millipore, #MATAH0P00)
  MicroScint-0™ (PerkinElmer, #6013611, Wellesley, MA)
  Binding Buffer: 25 mM Hepes (pH 7.4), 1 mM CaCl$_2$, 5 mM MgCl$_2$, 2.5 mM EDTA, 0.4% BSA Assay Volumes
  Competition experiments were performed in a 300 µL filtration assay format.
  220 µL of membranes diluted in binding buffer
  40 µL of compound diluted in binding buffer
  40 µL of radioligand ([$^{125}$I]-Ghrelin) diluted in binding buffer Final test concentrations (N=1) for compounds of the present invention:
  10, 1, 0.5, 0.2, 0.1, 0.05, 0.02, 0.01, 0.005, 0.002, 0.001 µM.

Compound Handling
  Compounds were provided frozen on dry ice at a stock concentration of 10 mM diluted in 100% DMSO and stored at −80° C. until the day of testing. On the test day, compounds were allowed to thaw at rt overnight and then diluted in assay buffer according to the desired test concentrations. Under these conditions, the maximal final DMSO concentration in the assay was 0.1%.

Assay Protocol
  In deep-well plates, 220 µL of diluted cell membranes (final concentration: 0.71 µg/well) were combined with 40 µL of either binding buffer (total binding, N =5), 1 µM ghrelin (non-specific binding, N =3) or the appropriate concentration of test compound (N =2 for each test concentration). The reaction was initiated by addition of 40 µL of [$^{125}$I]-ghrelin (final conc. 0.0070-0.0085 nM) to each well. Plates were sealed with TopSeal-A™, vortexed gently and incubated at rt for 30 min. The reaction was arrested by filtering samples through Multiscreen® Harvest plates (pre-soaked in 0.5% polyethyleneimine) using a Tomtec®Harvester (Tomtec, Hamden, CT), washed 9 times with 500 µL of cold 50 mM Tris-HCl (pH 7.4, 4° C), and then plates were air-dried in a fumehood for 30 min. A bottom seal was applied to the plates prior to the addition of 25 µL of MicroScint-0™ to each well. Plates were than sealed with TopSeal-A™ and counted for 30 sec per well on a TopCount® Microplate Scintillation and Luminescence Counter (PerkinElmer, Wellesley, MA) using a count delay of 60 sec. Results were expressed as counts per minute (cpm).

Data were analyzed by GraphPad™ Prism® (GraphPad Software, San Diego, CA) using a variable slope non-linear regression analysis. $K_i$ values were calculated using a $K_d$ value of 0.01 nM for [$^{125}$I]-ghrelin (previously determined during membrane characterization).

$D_{max}$ values were calculated using the following formula:

$$D_{max} = 1 - \frac{\text{test concentration with maximal displacement} - \text{non-specific binding}}{\text{total binding} - \text{non-specific binding}} \times 100$$

where total and non-specific binding represent the cpm obtained in the absence or presence of 1 µM ghrelin, respectively.

Example Method B3

Aequorin Functional Assay (Motilin Receptor)

Materials:
Membranes were prepared using AequoScreen™ (EURO-SCREEN, Belgium) cell lines expressing the human motilin receptor (cell line ES-380-A; receptor accession #AF034632). This cell line is constructed by transfection of the human motilin receptor into CHO-K1 cells co-expressing $G_{\alpha16}$ and the mitochondrially targeted Aequorin (Ref #ES-WT-A5).
Motilin (Bachem, #H-4385, Bachem Bioscience Inc., King of Prussia, PA)
Assay buffer: DMEM-F12 (Dulbeccoe's Modified Eagles Medium) with 15 mM HEPES and 0.1% BSA (pH 7.0)
Coelenterazine (Molecular Probes™, Leiden, The Netherlands)
Final Test Concentrations (N=5) for Compounds:
10, 3.16,1, 0.316, 0.1 µM.

Compound Handling:
Compounds were provided as dry films at a quantity of approximately 1.2 µmol in pre-formatted 96-well plates. Compounds were dissolved in 100% DMSO at a concentration of 10 mM and stored at −20° C. until further use. Daughter plates were prepared at a concentration of 500 µM in 30% DMSO with 0.1 % BSA and stored at −20° C. until testing. On the test day, compounds were allowed to thaw at room temperature and than diluted in assay buffer according to the desired test concentrations. Under these conditions, the maximum final DMSO concentration in the assay was 0.6%.

Cell Preparation:
Cells are collected from culture plates with $Ca^{2+}$ and $Mg^{2+}$-free phosphate buffered saline (PBS) supplemented with 5 mM EDTA, pelleted for 2 minutes at 1000× g, resuspended in assay buffer (see above) at a density of 5×10$^6$ cells/mL and incubated overnight in the presence of 5 µM coelenterazine. After loading, cells were diluted with assay buffer to a concentration of 5×10$^5$ cells/mL.

Assay Protocol:
For agonist testing, 50 µl of the cell suspension was mixed with 50 µl of the appropriate concentration of test compound or motilin (reference agonist) in 96-well plates (duplicate samples). The emission of light resulting from receptor activation was recorded using the Functional Drug Screening System 6000 'FDSS 6000' (Hamamatsu Photonics K.K., Japan).

For antagonist testing, an approximate EC80 concentration of motilin (i.e. 0.5 nM; 100 µL) was injected onto the cell suspension containing the test compounds (duplicate samples) 15-30 minutes after the end of agonist testing and the consequent emission of light resulting from receptor activation was measured as described in the paragraph above.

Results are expressed as Relative Light Units (RLU). Concentration response curves were analyzed using GraphPad™Prism® (GraphPad Software, San Diego, CA) by non-linear regression analysis (sigmoidal dose-response) based on the equation $E=E_{max}/(1+EC_{50}/C)n$ where E is the measured RLU value at a given agonist concentration (C), $E_{max}$ is the maximal response, $EC_{50}$ is the concentration producing 50% stimulation and n is the slope index. For agonist testing, results for each concentration of test compound were expressed as percent activation relative to the signal induced by motilin at a concentration equal to the $EC_{80}$ (i.e. 0.5 nM). For antagonist testing, results for each concentration of test compound were expressed as percent inhibition relative to the signal induced by motilin at a concentration equal to the $EC_{80}$ (i.e. 0.5 nM).

Example Method B4

Aequorin Functional Assay (Ghrelin Receptor)

Materials
Membranes were prepared using AequoScreen™ (EURO-SCREEN, Belgium) cell lines expressing the human ghrelin receptor (cell line ES-410-A; receptor accession #60179). This cell line is constructed by transfection of the human ghrelin receptor into CHO-KL cells co-expressing $G_{\square16}$ and the mitochondrially targeted Aequorin (Ref #ES-WT-A5).
Ghrelin (reference agonist; Bachem, #H-4864,Bachem Bioscience Inc., King of Prussia,PA)
Assay buffer: DMEM (Dulbecco's Modified Eagles Medium) containing 0.1% BSA (bovine serum albumin; pH 7.0.
Coelenterazine (Molecular Probes, Leiden, The Netherlands)
Final test concentrations (N=8) for compounds of the invention:
10, 1, 0.3, 0.1, 0.03, 0.01, 0.003, 0.001 µM.

Compound Handling
Stock solutions of compounds (10 mM in 100% DMSO) were provided frozen on dry ice and stored at −20° C. prior to use. From the stock solution, mother solutions were made at a concentration of 500 µM by 20-fold dilution in 26% DMSO. Assay plates were then prepared by appropriate dilution in DMEM medium containing 0.1% BSA. Under these conditions, the maximal final DMSO concentration in the assay was <0.6%.

Cell Preparation

AequoScreen™ cells were collected from culture plates with $Ca^{2+}$ and $Mg^{2+}$-free phosphate buffered saline (PBS) supplemented with 5 mM EDTA, pelleted for 2 min at 1000× g, re-suspended in DMEM—Ham's F12 containing 0.1% BSA at a density of $5×10^6$ cells/mL, and incubated overnight at rt in the presence of 5 µM coelenterazine. After loading, cells were diluted with assay buffer to a concentration of $5×10^5$ cells/mL.

Assay Protocol

For agonist testing, 50 µL of the cell suspension was mixed with 50 µL of the appropriate concentration of test compound or ghrelin (reference agonist) in 96-well plates (duplicate samples). Ghrelin (reference agonist) was tested at several concentrations concurrently with the test compounds in order to validate the experiment. The emission of light resulting from receptor activation in response to ghrelin or test compounds was recorded using the Hamamatsu FDSS 6000 reader (Hamamatsu Photonics K.K., Japan).

Analysis and Expression of Results

Results were expressed as Relative Light Units (RLU). Concentration response curves were analyzed using Graph-Pad Prism (GraphPad Software, San Diego, Calif.) by non-linear regression analysis (sigmoidal dose-response) based on the equation $E=E_{max}/(1+EC_{50}/C)n$ where E was the measured RLU value at a given agonist concentration (C), $E_{max}$ was the maximal response, $EC_{50}$ was the concentration producing 50% stimulation and n was the slope index. For agonist testing, results for each concentration of test compound are expressed as percent activation relative to the signal induced by ghrelin at a concentration equal to the $EC_{80}$ (i.e. 3.7 nM). $EC_{50}$, Hill slope and % $E_{max}$ values are reported.

TABLE 3

Biological Activity of Representative Compounds of formula I

| Compound | Binding Affinity [$K_i$ (µM)][1] | Receptor[2] |
| --- | --- | --- |
| 201 | A | motilin (human) |
| 202 | A | motilin (human) |
| 203 | A | motilin (human) |
| 204 | A | motilin (human) |
| 205 | B | motilin (human) |
| 206 | B | motilin (human) |
| 207 | A | motilin (human) |

TABLE 3-continued

Biological Activity of Representative Compounds of formula I

| Compound | Binding Affinity [$K_i$ (µM)][1] | Receptor[2] |
| --- | --- | --- |
| 208 | A | motilin (human) |
| 209 | A | motilin (human) |
| 210 | A | motilin (human) |
| 211 | A | motilin (human) |
| 212 | A | motilin (human) |
| 213 | A | motilin (human) |
| 214 | A | motilin (human) |
| 215 | A | motilin (human) |
| 216 | A | motilin (human) |
| 217 | B | motilin (human) |
| 218 | B | motilin (human) |
| 219 | B | motilin (human) |
| 220 | B | motilin (human) |
| 221 | B | motilin (human) |
| 222 | A | motilin (human) |
| 223 | A | motilin (human) |
| 224 | B | motilin (human) |
| 226 | B | motilin (human) |
| 227 | B | motilin (human) |
| 228 | B | motilin (human) |
| 235 | C | motilin (human) |
| 236 | B | motilin (human) |
| 237 | B | motilin (human) |
| 241 | A | ghrelin (human) |
| 242 | A | ghrelin (human) |
| 243 | A | ghrelin (human) |
| 244 | A | ghrelin (human) |
| 245 | A | ghrelin (human) |
| 246 | B | ghrelin (human) |
| 247 | B | ghrelin (human) |
| 248 | B | ghrelin (human) |
| 251 | B | ghrelin (human) |
| 254 | A | ghrelin (human) |
| 255 | A | ghrelin (human) |
| 256 | B | ghrelin (human) |
| 257 | A | ghrelin (human) |
| 258 | B | ghrelin (human) |
| 259 | C | ghrelin (human) |
| 260 | C | ghrelin (human) |
| 261 | C | ghrelin (human) |
| 262 | B | ghrelin (human) |
| 263 | B | ghrelin (human) |
| 264 | B | ghrelin (human) |

[1]Activity presented indicated in the following ranges: A = 0.001–0.10 µM, B = 0.1–1.0 µM, C = 1.0–10.0 µM
[2]Binding conducted using the Standard Methods described in the Examples Although preferred embodiments of the present invention have been described in detail herein, it is to be understood that the invention is not limited to these precise embodiments and that various changes and modifications may be effected therein without departing from the scope or spirit of the present invention.

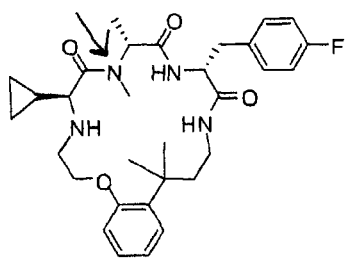

What is claimed is:

1. A compound having the structure of formula II:

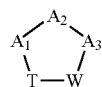

(II)

wherein W, $A_1$, $A_2$, $A_3$ and T are defined as below with the NH of $A_1$ bonded to T, the C=O of $A_1$ bonded to the NH of A2, the C=O of A2 bonded to the NH of $A_3$, the C=O of $A_3$ bonded to W, and (W) and ($A_1$) indicate the site of bonding of T to W and $A_1$, respectively:

| W | $A_1$ |
|---|---|
| NH | CF$_3$ 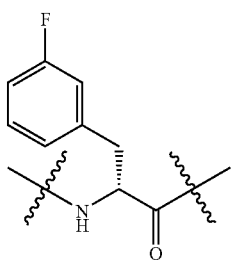 |
| NH | F 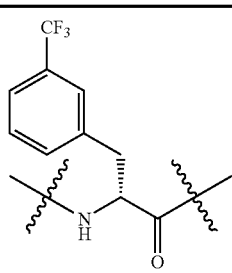 |
| NH | Cl 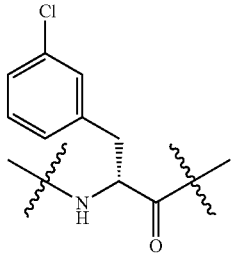 |

| NH | 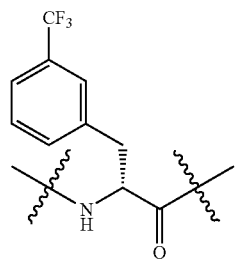 | | NH | 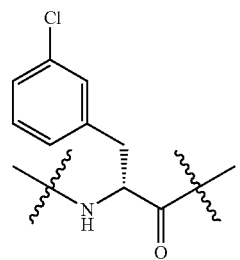 |
|---|---|---|---|---|
| NH | 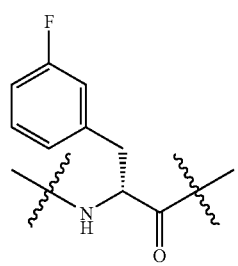 | | NH | 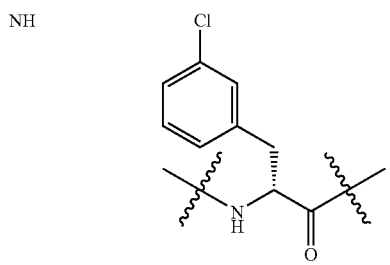 |
| NH | 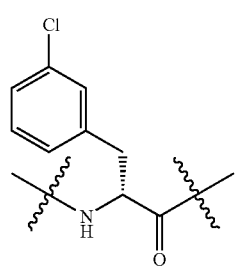 | | NH | 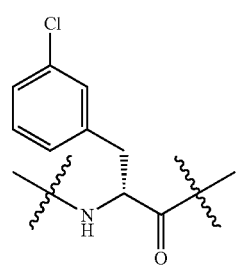 |
| NH | 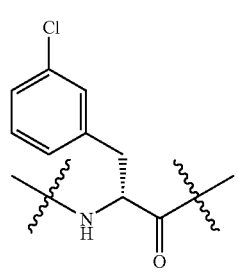 | | NH | 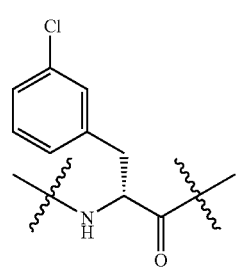 |
| NH | 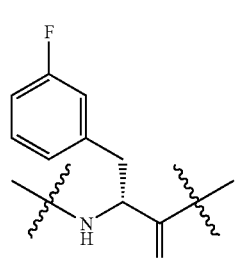 | | NH | 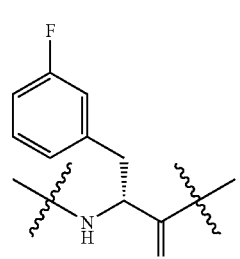 |
| NH | 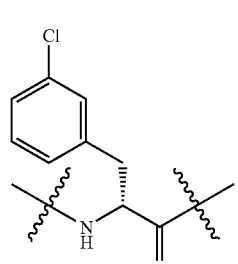 | | NH | 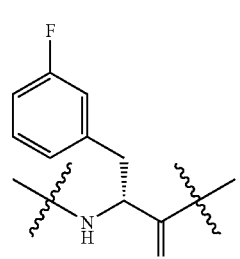 |

-continued
| | |
|---|---|
| NH | 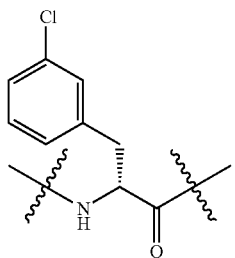 |
| NH | 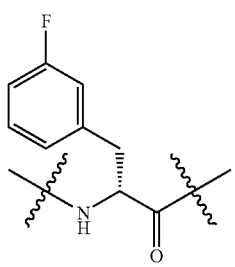 |
| NH | 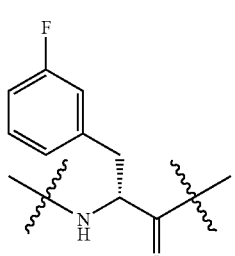 |
| NH | 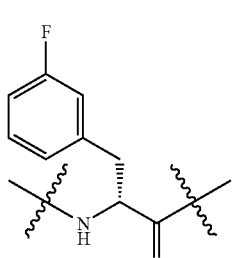 |
| NH | 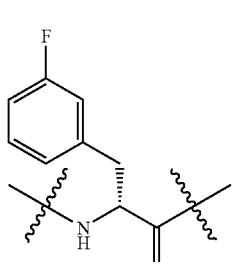 |
| NH | 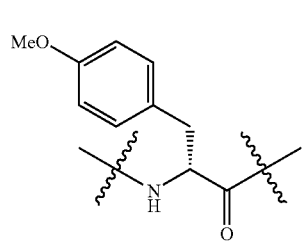 |
-continued
| | |
|---|---|
| NH | 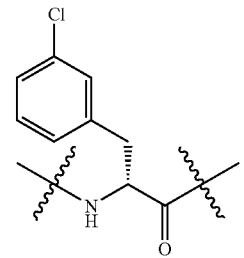 |
| NH | 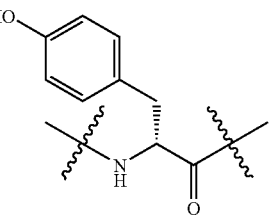 |
| NH | 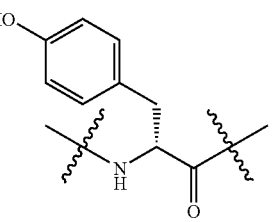 |
| NH | 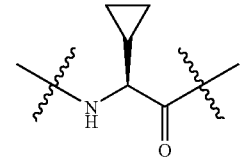 |
| NH | 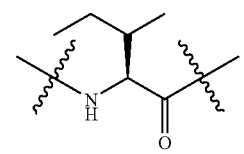 |
| NH | 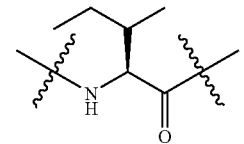 |
| NH | 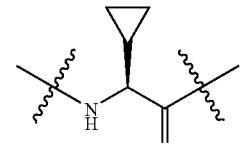 |
| NH | 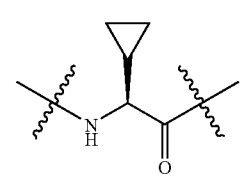 |

-continued
| W | A₂ |
|---|---|
| NH | 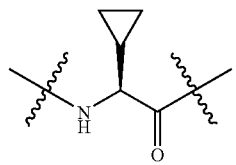 |
| NH | 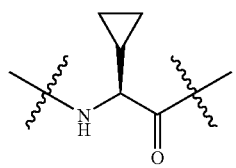 |
| NH | 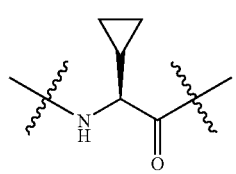 |
| NH | 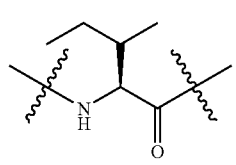 |
| NH | 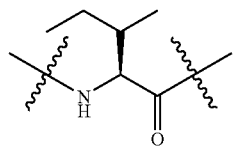 |
| NH | 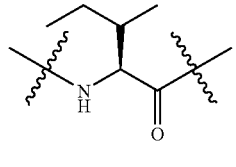 |
| NH | 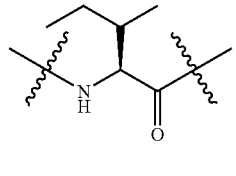 |
| NH | 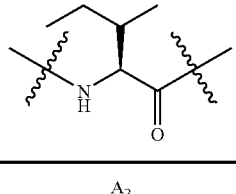 |
| W | A₂ |
|---|---|
| NH | 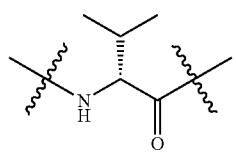 |
-continued
| | |
|---|---|
| NH | 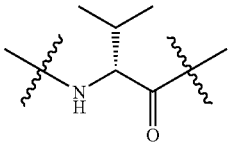 |
| NH | 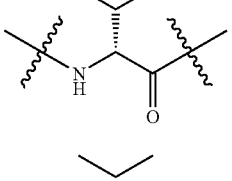 |
| NH | 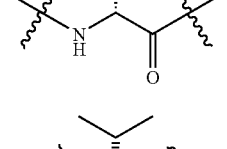 |
| NH | 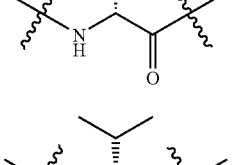 |
| NH | 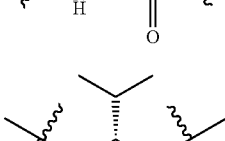 |
| NH | 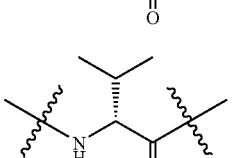 |
| NH | 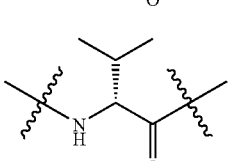 |
| NH | 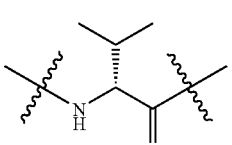 |
| NH | 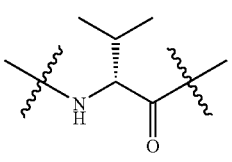 |

| | | |
|---|---|---|
| NH | 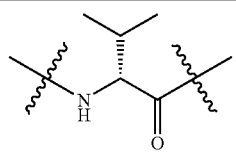 | |
| NH | 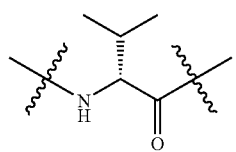 | |
| NH | 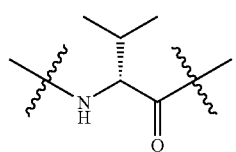 | |
| NH | 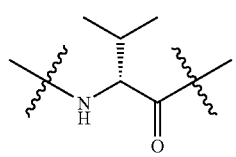 | |
| NH | 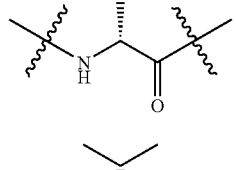 | |
| NH | 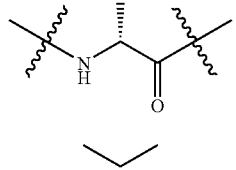 | |
| NH | 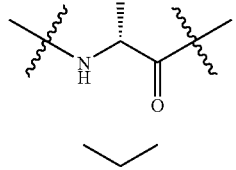 | |
| NH | 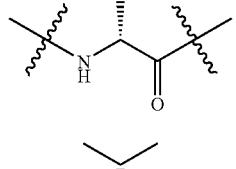 | |
| NH | 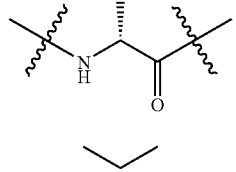 | |
| NH | 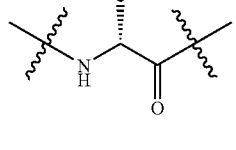 | |
| | |
|---|---|
| NH | 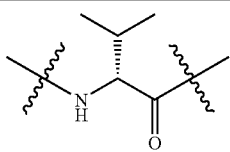 |
| NH | 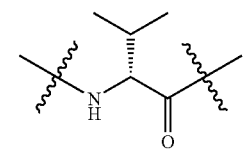 |
| NH | 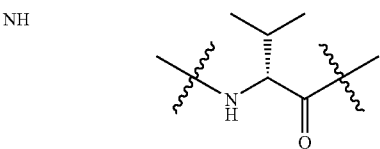 |
| NH | 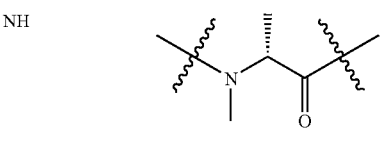 |
| NH | 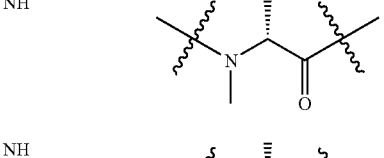 |
| NH | 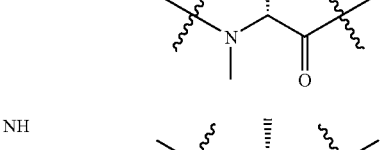 |
| NH | 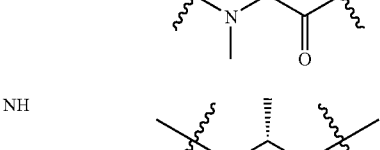 |
| NH | 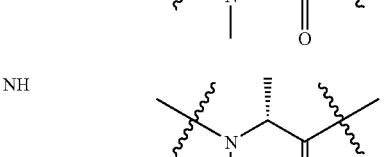 |
| NH | 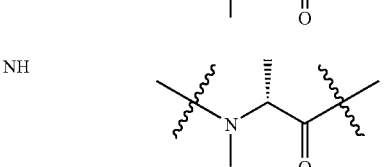 |
| NH | 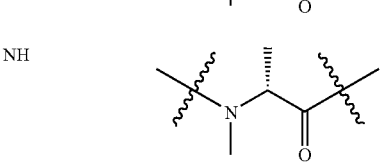 |

-continued
| | |
|---|---|
| NH | 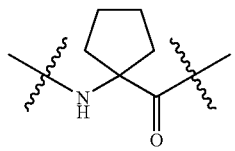 |
| NH | 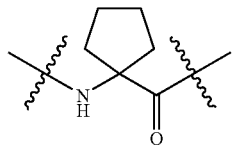 |
| NH | 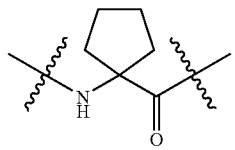 |
| NH | 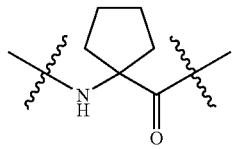 |
| NH | 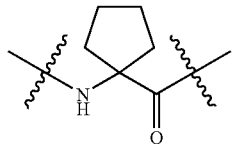 |
| W | A₃ |
|---|---|
| NH | 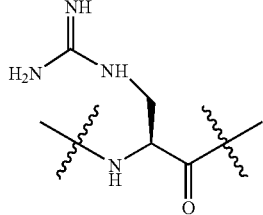 |
| NH | 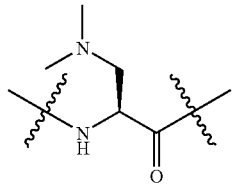 |
| NH | 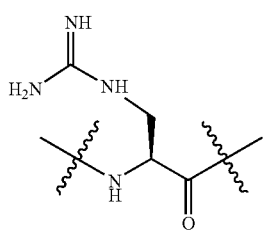 |
-continued
| | |
|---|---|
| NH | 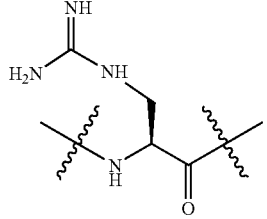 |
| NH | 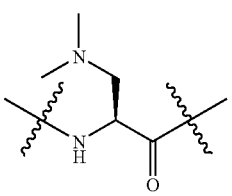 |
| NH | 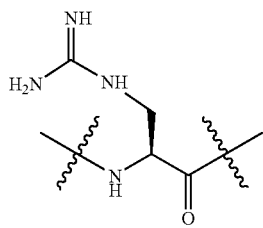 |
| NH | 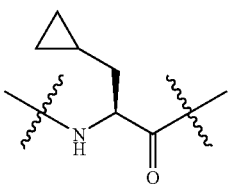 |
| NH | 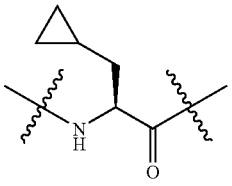 |
| NH | 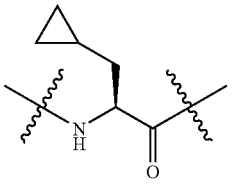 |
| NH | 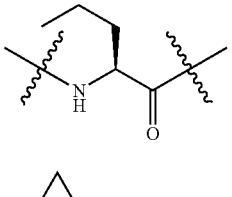 |
| NH | 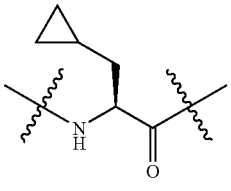 |

| | |
|---|---|
| NH | 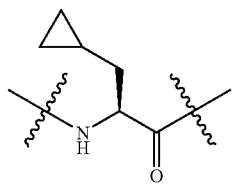 |
| NH | 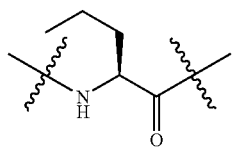 |
| NH | 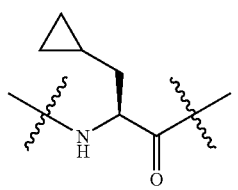 |
| NH | 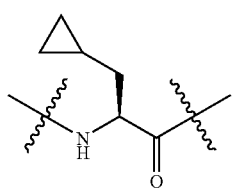 |
| NH | 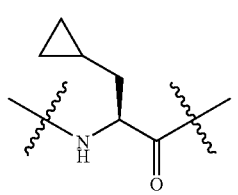 |
| NH | 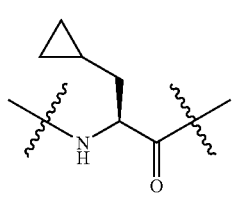 |
| NH | 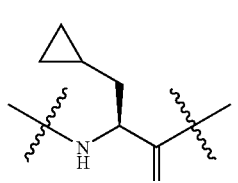 |
| NH | 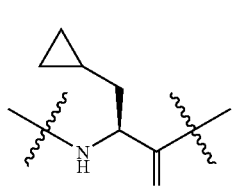 |
| | |
|---|---|
| NH | 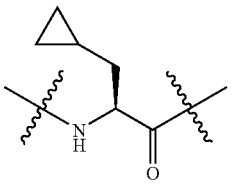 |
| NH | 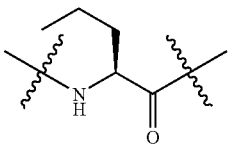 |
| NH | 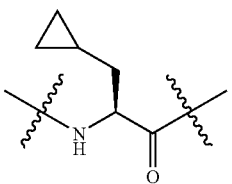 |
| NH | 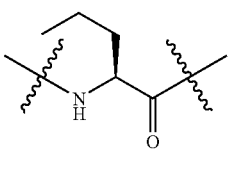 |
| NH | 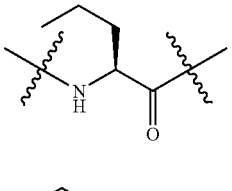 |
| NH | 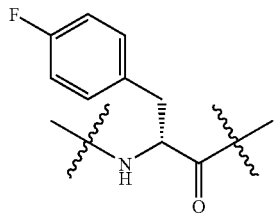 |
| NH | 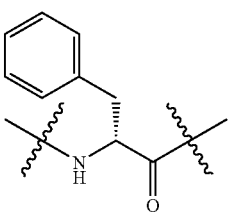 |
| NH | 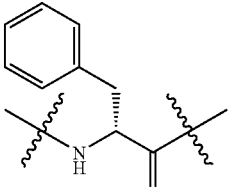 |

| | -continued | | | -continued | |
|---|---|---|---|---|---|
| NH | 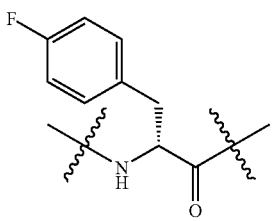 | | NH | 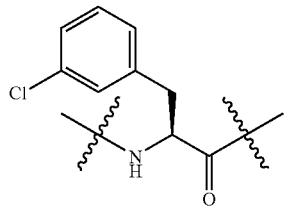 | |
| NH | 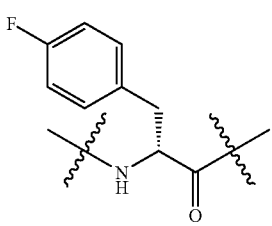 | | NH | 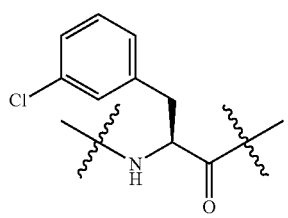 | |
| NH | 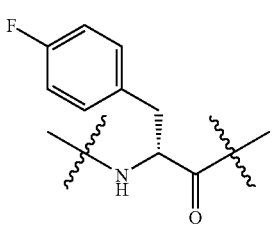 | | NH | 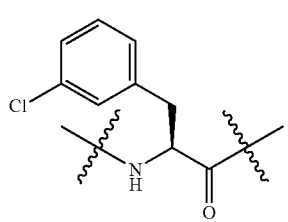 | |
| W | T |
|---|---|
| NH | 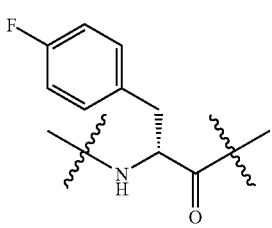 |
| NH | 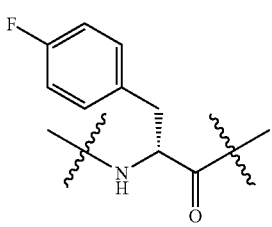 |
| NH | 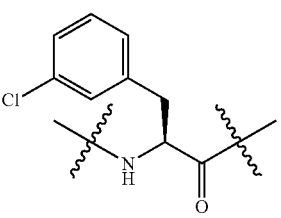 |
| NH | 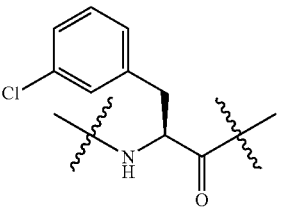 |
| W | T |
|---|---|
| NH | 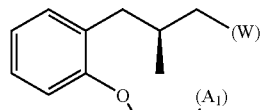 |
| NH | 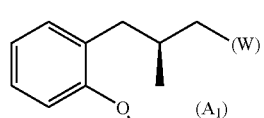 |
| NH | 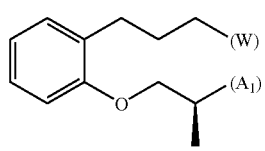 |
| NH | 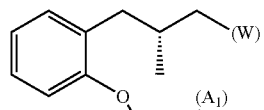 |
| NH | 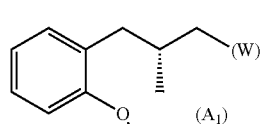 |
| NH | 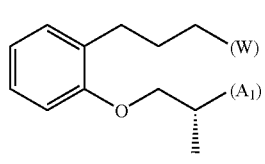 |

-continued
| | | |
|---|---|---|
| NH | 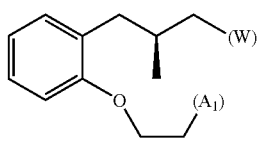 | |
| NH | 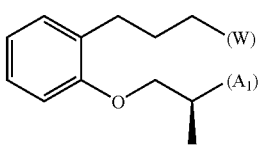 | |
| NH | 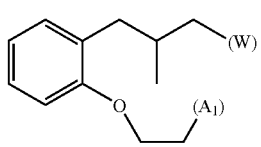 | |
| NH | 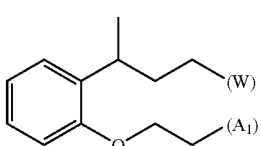 | |
| NH | 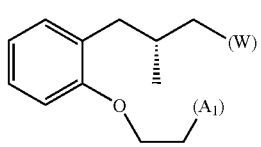 | |
| NH | 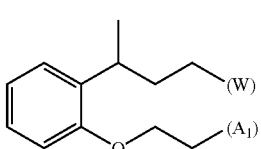 | |
| NH | 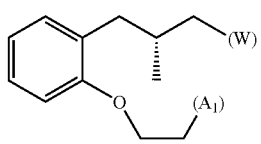 | |
| NH | 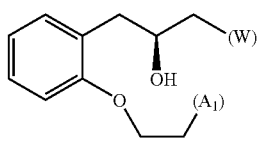 | |
| NH | 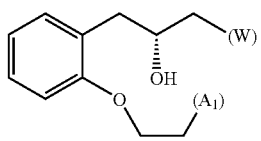 | |
-continued
| | | |
|---|---|---|
| NH | 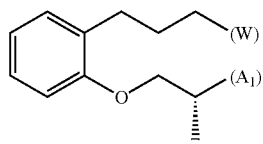 | |
| NH | 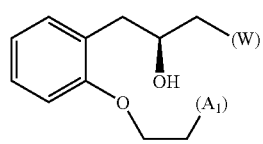 | |
| NH | 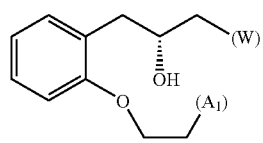 | |
| NH | 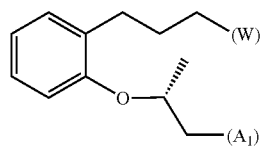 | |
| NH | 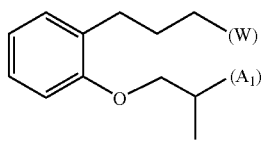 | |
| NH | 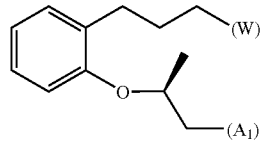 | |
| NH | 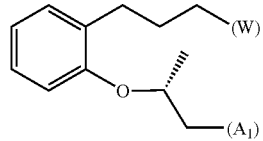 | |
| NH | 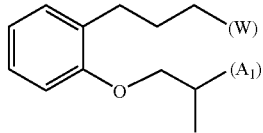 | |

2. An antagonist of a mammalian motilin receptor having the following structure:

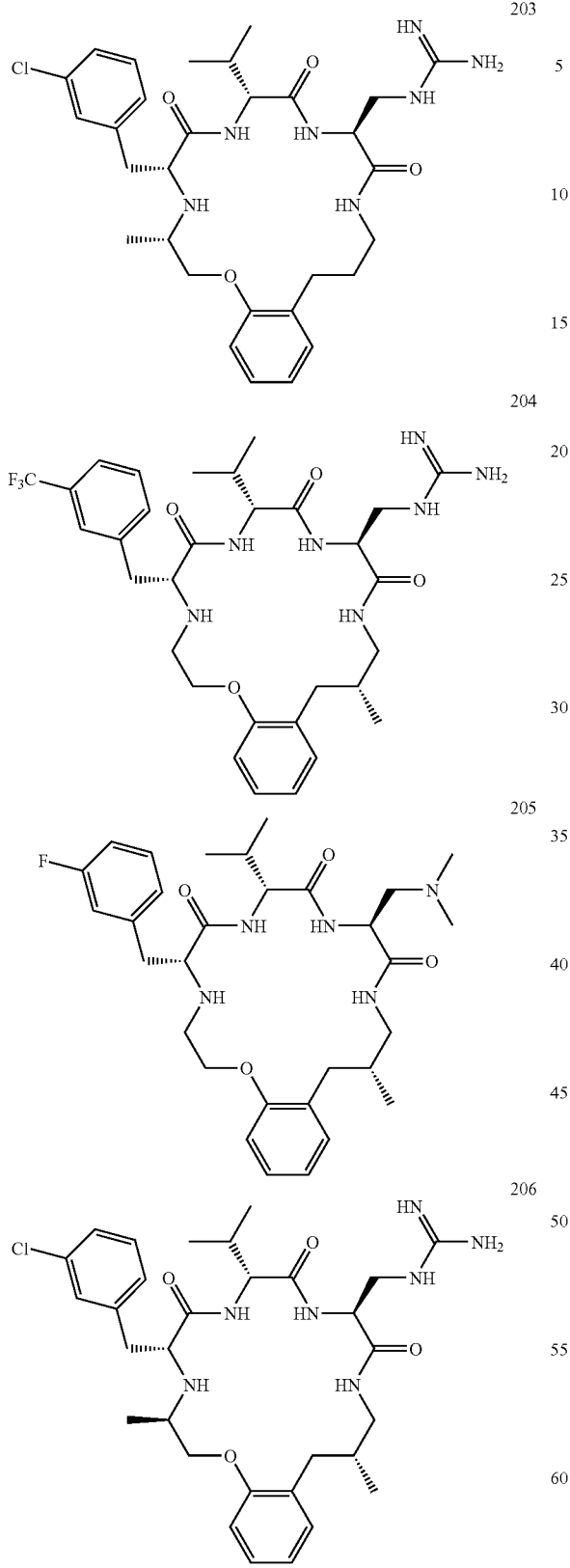

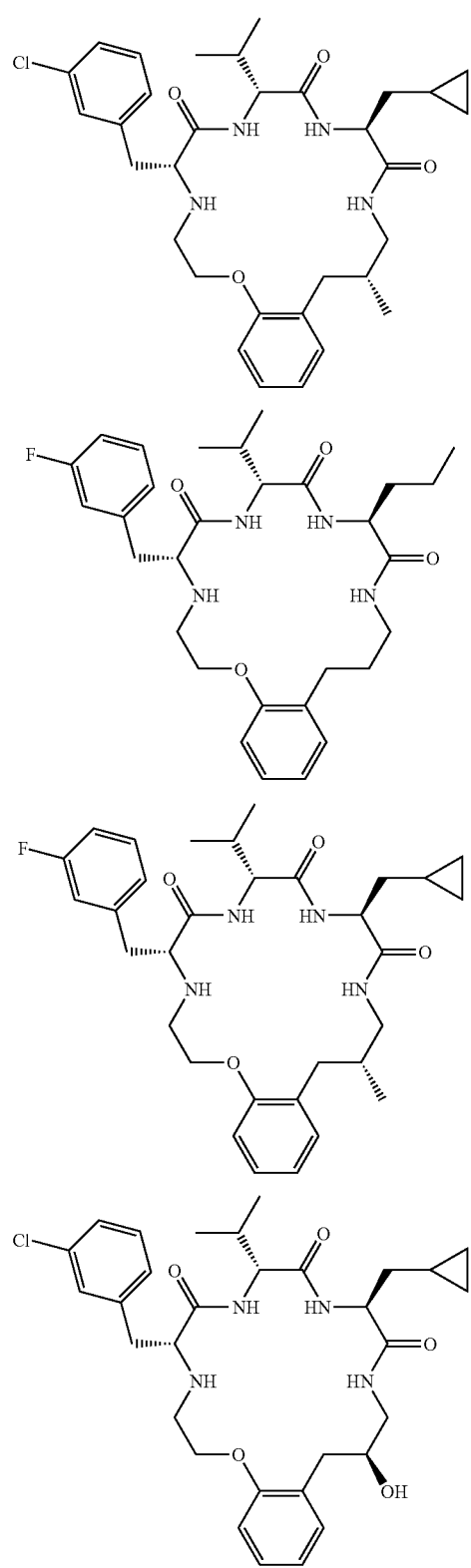
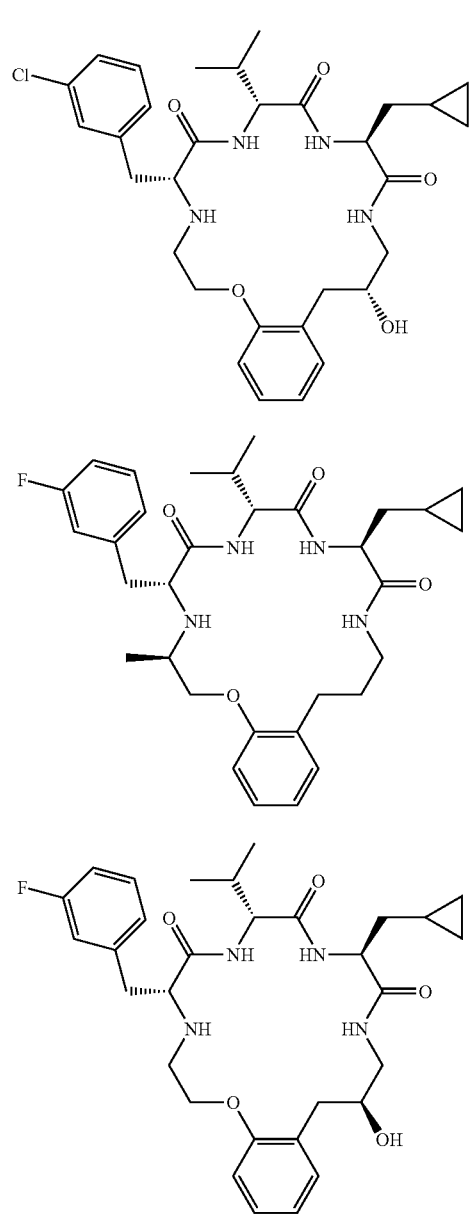

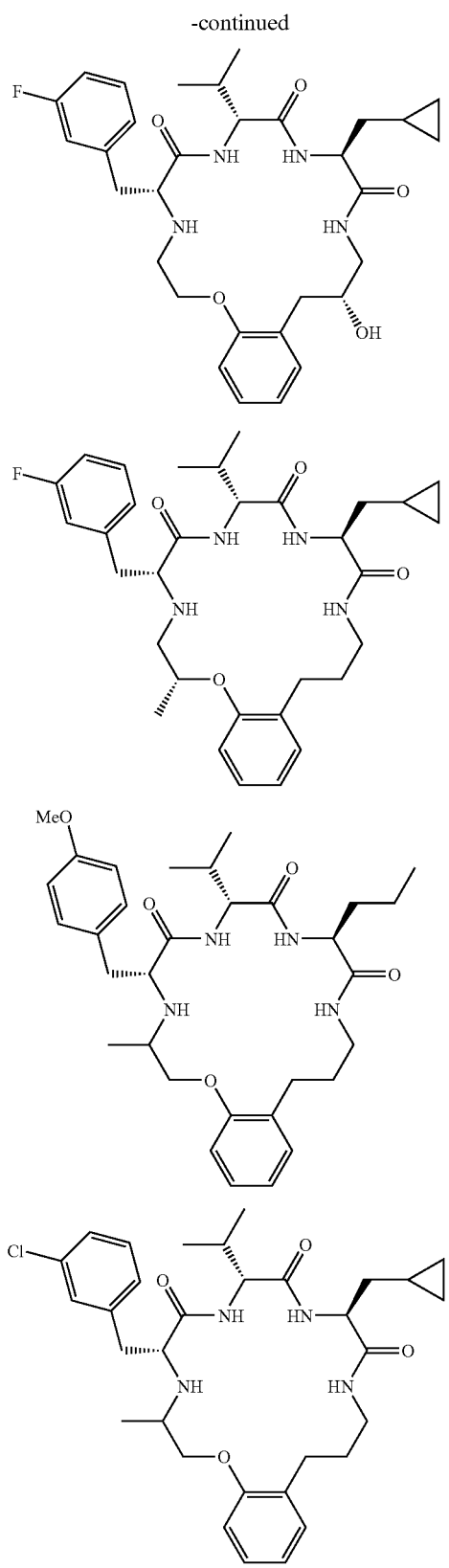
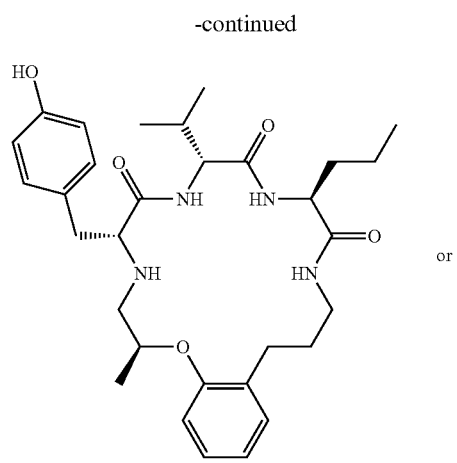
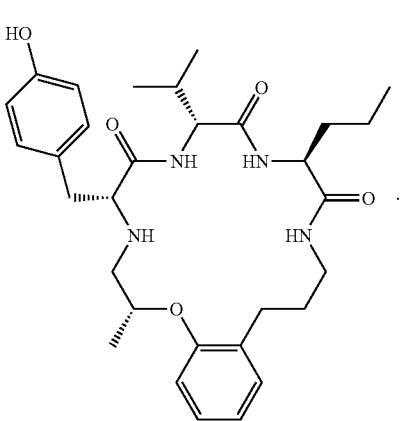
3. An agonist of a mammalian ghrelin receptor having the following structure:
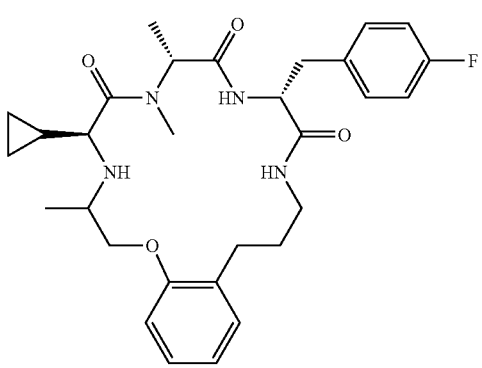

-continued
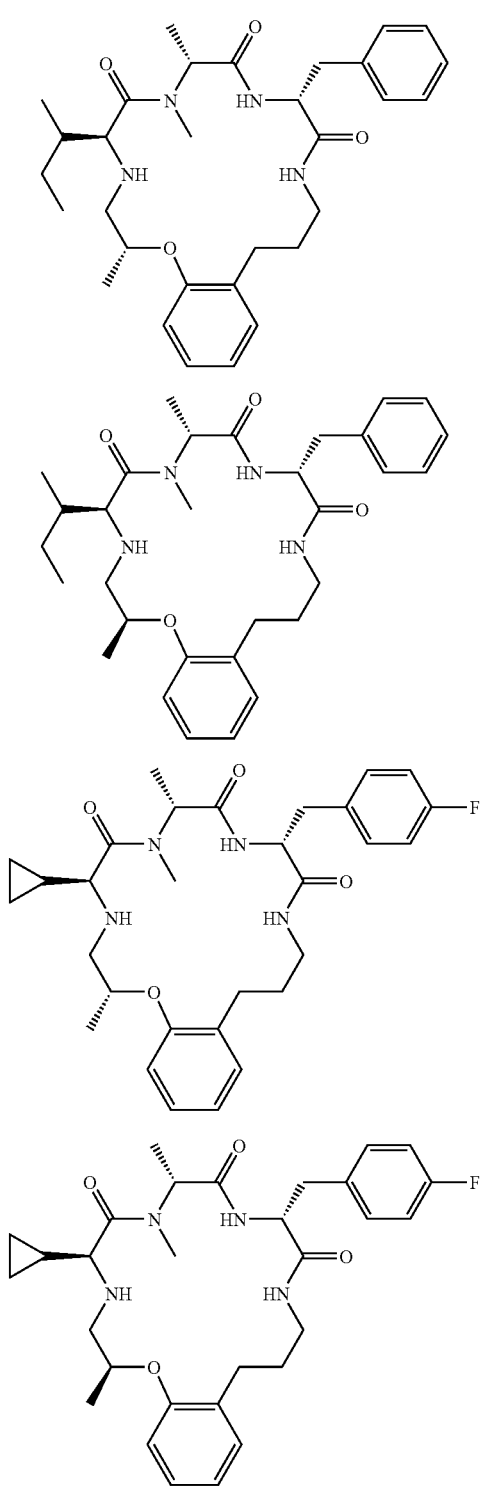
-continued
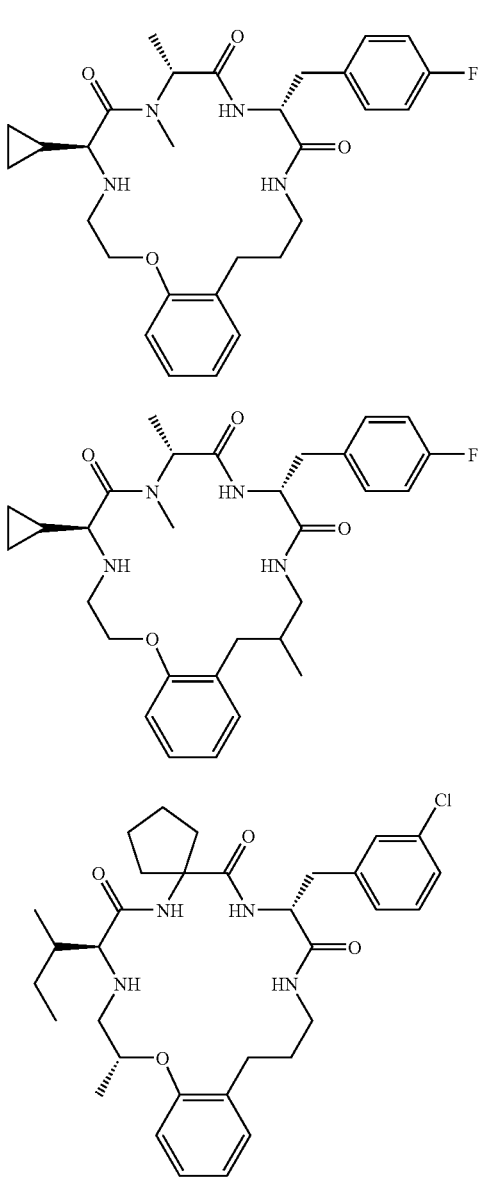

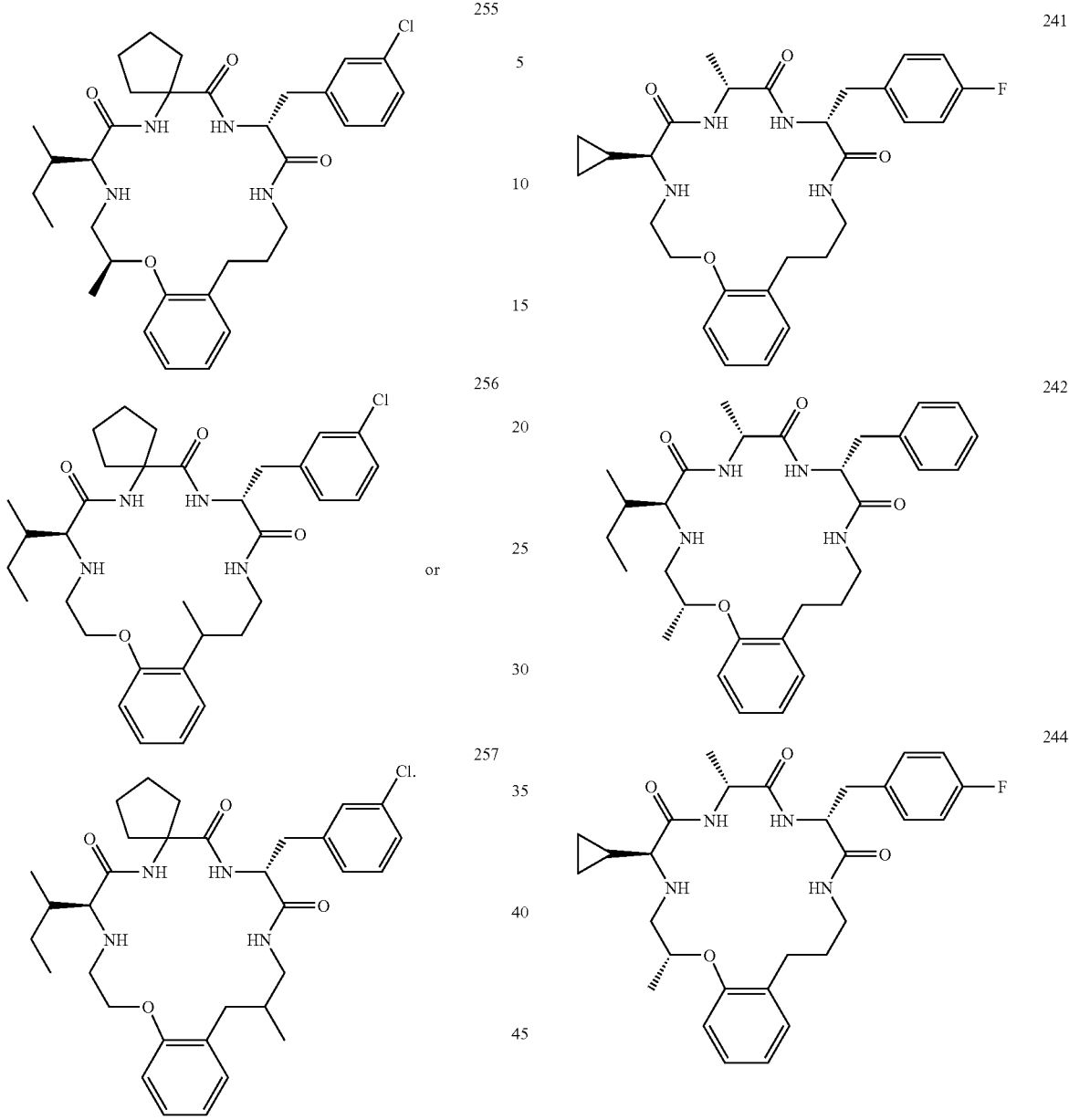
4. A compound having a structure selected from the following:

-continued
245
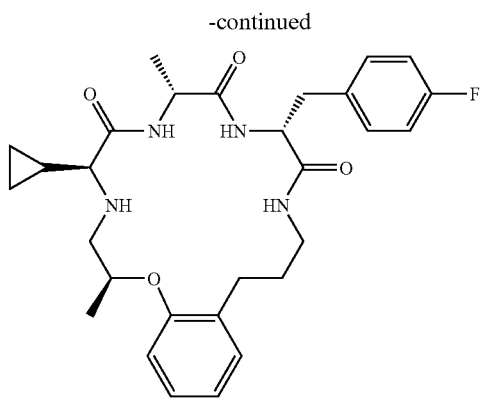
246
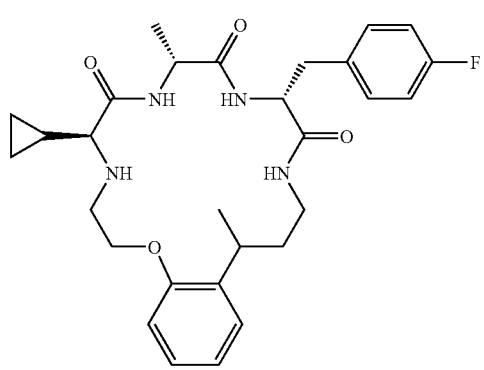
or
247
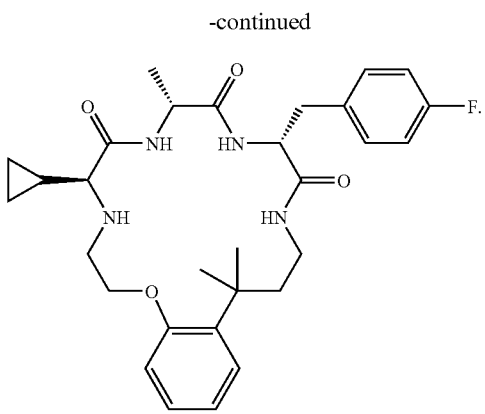
* * * * *

UNITED STATES PATENT AND TRADEMARK OFFICE
CERTIFICATE OF CORRECTION

PATENT NO. : 7,452,862 B2
APPLICATION NO. : 10/911221
DATED : November 18, 2008
INVENTOR(S) : Deslongchamps et al.

It is certified that error appears in the above-identified patent and that said Letters Patent is hereby corrected as shown below:

Column 12, Lines 17-18: Correct "Tiibinaen" to read --Tübingen--

Columns 29-30 at compound 235: Replace the structure

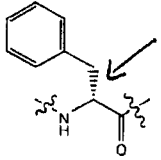

With the structure

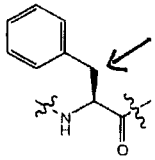

Columns 29-30 at compound 241: Replace the structure

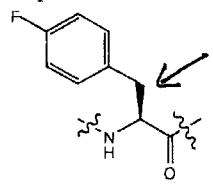

With the structure

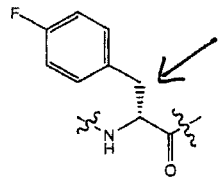

Signed and Sealed this

Twenty-first Day of December, 2010

David J. Kappos
*Director of the United States Patent and Trademark Office*

Columns 31-32 at compound 244: Replace the structure
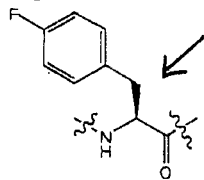
With the structure
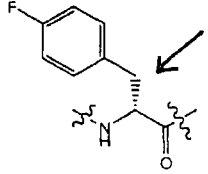
Columns 31-32 at compound 245: Replace the structure
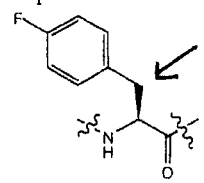
With the structure
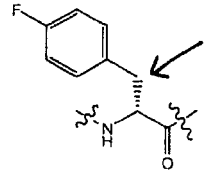
Columns 31-32 at compound 246: Replace the structure
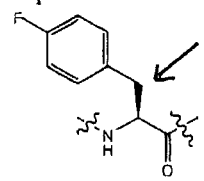
With the structure
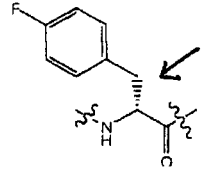

Columns 31-32 at compound 247: Replace the structure
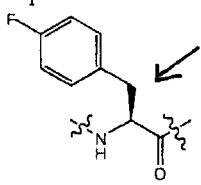
With the structure
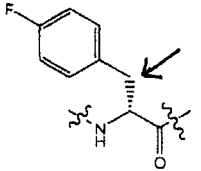
Columns 31-32 at compound 248: Replace the structure
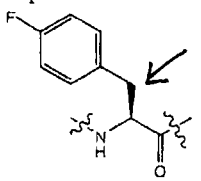
With the structure
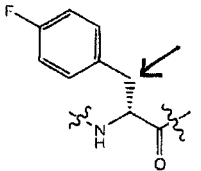
Columns 33-34 at compound 249: Replace the structure
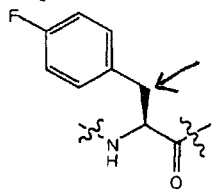
With the structure
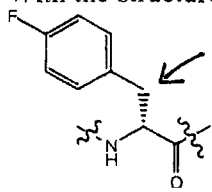

Columns 33-34 at compound 250: Replace the structure
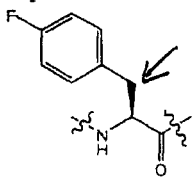
With the structure
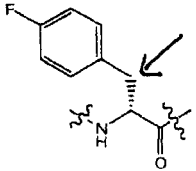
Column 40, Line 26: Correct "PerkinlElmer" to read --PerkinElmer--
Column 45, Line 49: Correct "A2" (two instances) to read --$A_2$--
Column 64, Line 40: Replace the structure
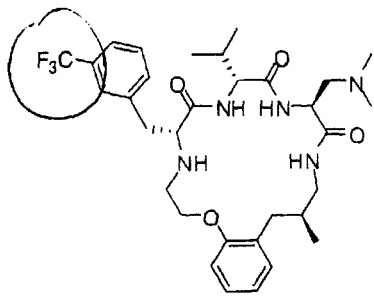
With the structure
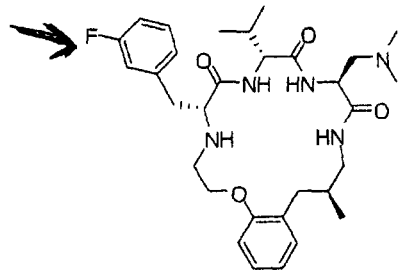

Column 65, Line 50: Replace the structure
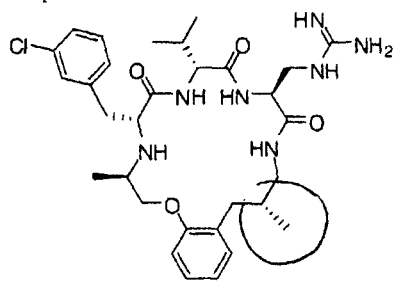
With the structure
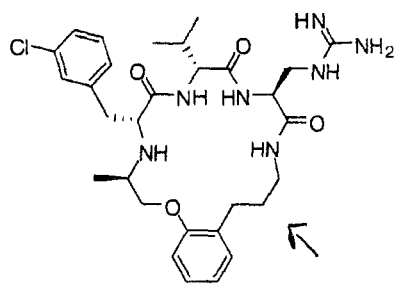
Column 66, Line 50: Replace the structure
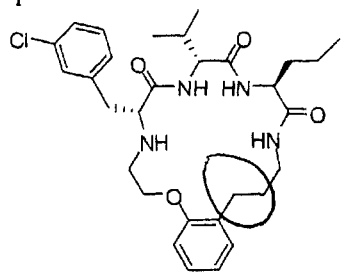
With the structure
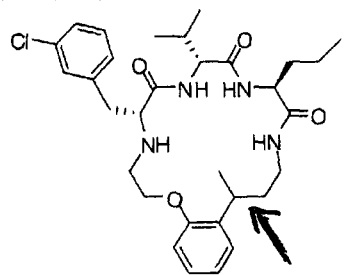

CERTIFICATE OF CORRECTION (continued)
U.S. Pat. No. 7,452,862 B2

Column 67, Line 20:    Replace the structure

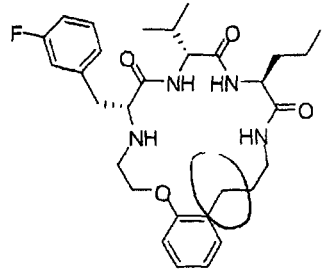

With the structure

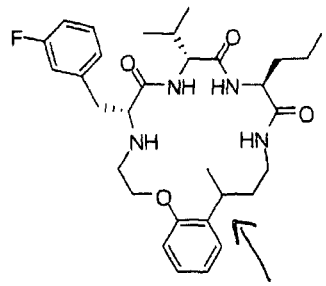

Column 72, Line 5:    Replace the structure

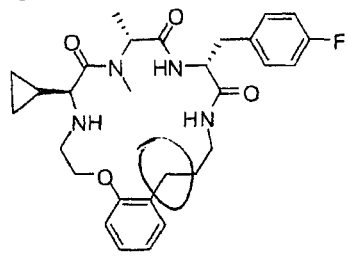

With the structure

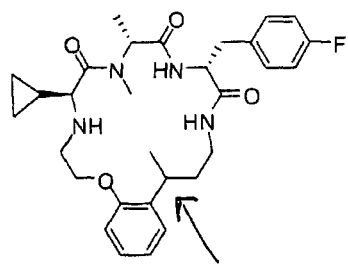

CERTIFICATE OF CORRECTION (continued)
U.S. Pat. No. 7,452,862 B2

Column 74, Line 5:  Replace the structure

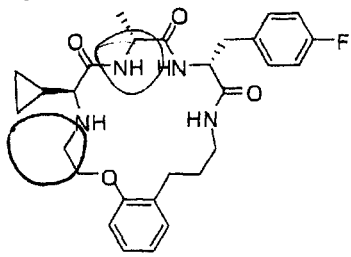

With the structure

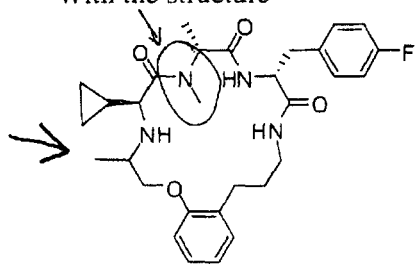

Column 74, Line 20:  Replace the structure

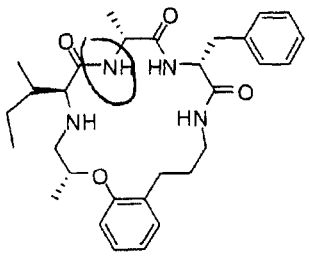

With the structure

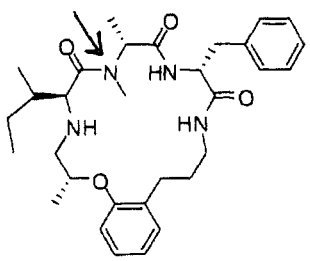

CERTIFICATE OF CORRECTION (continued)
U.S. Pat. No. 7,452,862 B2

Column 74, Line 35:     Replace the structure

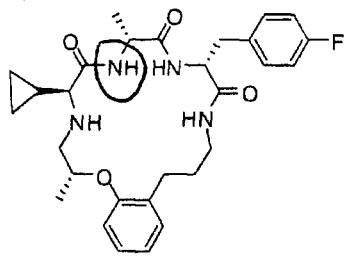

With the structure

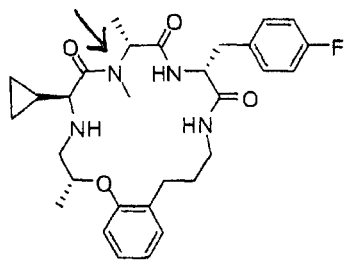

Column 75, Line 5:     Replace the structure

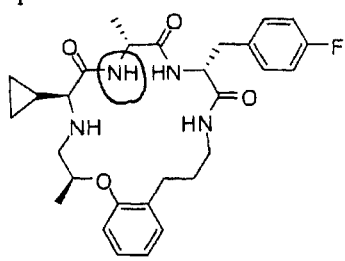

With the structure

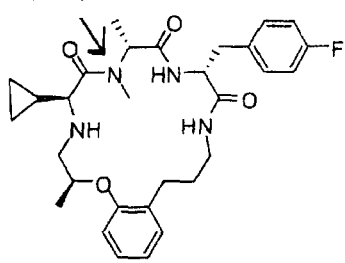

CERTIFICATE OF CORRECTION (continued)
U.S. Pat. No. 7,452,862 B2

Column 75, Line 20:       Replace the structure

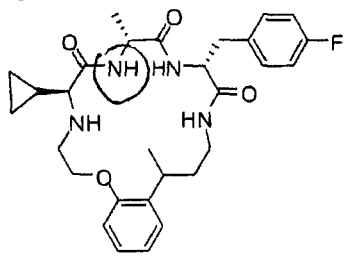

With the structure

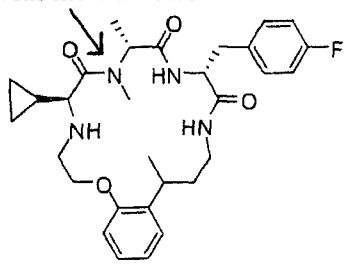

Column 76, Line 5:        Replace the structure

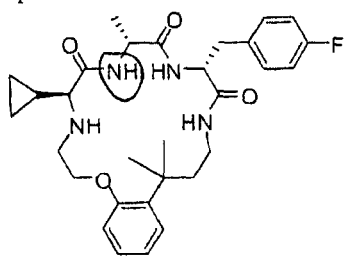

With the structure

```
                              SEQUENCE LISTING

<160> NUMBER OF SEQ ID NOS: 2

<210> SEQ ID NO 1
<211> LENGTH: 22
<212> TYPE: PRT
<213> ORGANISM: Homo sapiens

<400> SEQUENCE: 1

Phe Val Pro Ile Phe Thr Tyr Gly Glu Leu Gln Arg Met Gln Glu Lys
1               5                   10                  15

Glu Arg Asn Lys Gly Gln
            20

<210> SEQ ID NO 2
<211> LENGTH: 28
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: n-octanoyl modification site

<400> SEQUENCE: 2

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```